United States Patent [19]

Shenvi et al.

[11] Patent Number: 5,965,576
[45] Date of Patent: Oct. 12, 1999

[54] CYCLIC AMIDE DERIVATIVES FOR TREATING ASTHMA

[75] Inventors: Ashokkumar Bhikkappa Shenvi, 22 Carlton La., Wilmington, Del. 19808; Robert Toms Jacobs, 16 Marlborough Drive, Tytherington, Macclesfield, Cheshire, SK 10 2JX, United Kingdom; Scott Carson Miller, 2900 Crossfork Dr. , .Apartment 2C, Wilmington, Del. 19808; Cyrus John Ohnmacht, Jr., 3209 Drexel Dr., Wilmington, Del. 19810; Chris Allan Veale, 709 6th St., Green Valley, Newark, Del. 19711

[73] Assignee: Zeneca Limited, United Kingdom

[21] Appl. No.: 08/980,399

[22] Filed: Nov. 26, 1997

Related U.S. Application Data

[62] Division of application No. 08/717,999, Sep. 26, 1996, Pat. No. 5,705,505, which is a division of application No. 08/353,767, Dec. 12, 1994, Pat. No. 5,589,489.

[30] Foreign Application Priority Data

Dec. 15, 1993 [GB] United Kingdom .................... 9325654
Nov. 17, 1994 [GB] United Kingdom .................... 9423248

[51] Int. Cl.[6] ........................ A61K 31/445; C07D 401/14
[52] U.S. Cl. .......................... 514/323; 514/212; 514/218; 514/274; 514/316; 514/322; 514/326; 540/485; 540/492; 544/315; 546/193; 546/199; 546/200; 546/208

[58] Field of Search ..................................... 540/485, 492; 544/315; 546/193, 199, 208, 200; 514/212, 218, 274, 316, 326, 322, 323

[56] References Cited

U.S. PATENT DOCUMENTS 5,567,700  10/1996  Miller .................................. 514/226.8
5,677,317  10/1997  Miller .................................... 514/316

OTHER PUBLICATIONS

Maggi et al. "Tachykinin receptors and tachykinin receptor antagonists" J. Auton. Pharmc. v.13 pp. 23–93 (relevant pages only), 1993.

*Primary Examiner*—Celia Chang
*Attorney, Agent, or Firm*—Richard V. Person

[57] ABSTRACT

Compounds of formula I

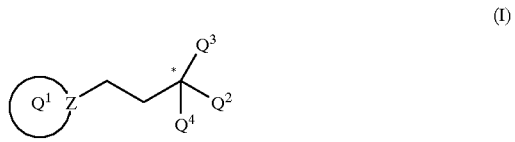

wherein $Q^1$, $Q^2$, $Q^3$, and $Q^4$ have any of the meanings given in the specification, their N-oxides, and their pharmaceutically acceptable salts are nonpeptide antagonists of neurokinin A and useful for the treatment of asthma, etc. Also disclosed are pharmaceutical compositions, processes for preparing the compounds of formula I and intermediates.

8 Claims, No Drawings

CYCLIC AMIDE DERIVATIVES FOR TREATING ASTHMA

This is a divisional of U.S. application Ser. No. 08/717,999 filed on Sep. 26, 1996 now U.S. Pat. No. 5,705,505, which is a divisional of U.S. application Ser. No. 08/353,767, filed on Dec. 12, 1994, now U.S. Pat. No. 5,589,489 issued on Dec. 31, 1996.

This invention concerns novel cyclic amide derivatives, and, more particularly, novel N-substituted benzo-fused lactams which antagonize the pharmacological actions of one of the endogenous neuropeptide tachykinins known as neurokinins, particularly at the neurokinin 2 (NK2) receptor. The novel cyclic amide derivatives are useful whenever such antagonism is desired. Thus, such compounds may be of value in the treatment of those diseases in which an NK2 receptor is implicated, for example, in the treatment of asthma and related conditions. The invention also provides pharmaceutical compositions containing the novel cyclic amide derivatives for use in such treatment, methods for their use, and processes and intermediates for the manufacture of the novel cyclic amide derivatives.

The mammalian neurokinins comprise a class of peptide neurotransmitters which are found in the peripheral and central nervous systems. The three principal neurokinins are Substance P (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, respectively, the receptors are classifed as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation and activation of mast cells. Thus, the tachykinins are implicated in the pathophysiology and the airway hyperresponsiveness observed in asthmatics; and blockade of the action of released tachykinins may be useful in the treatment of asthma and related conditions. Peptidic NK2 antagonists have been reported. For example, a cyclic hexapeptide known as L-659,877 has been reported as a selective NK2 antagonist. Nonpeptidic NK2 antagonists also have been reported, for example in European Patent Application, Publication Number (EPA) 428434, EPA 474561, EPA 512901, EPA 512902 and EPA 515240, as well as in EPA 559538. We have discovered a series of nonpeptidic NK2 antagonists, and this is the basis for our invention.

According to the invention, there is provided a Compound of the invention which is a compound of formula I (formula set out hereinbelow following the Examples, together with other formulae denoted by Roman numerals) wherein $Q^1$ is a radical (attached at Z) selected from the group of radicals of formulae Ia, Ib, Ic, Id, Ie, If, Ig, Ih, Ij and Ik wherein for a radical of formula Ia (in which Z denotes a nitrogen), $R^{aa}$ is Ar or Het; $R^{ab}$ is hydrogen and $R^{ac}$ is hydrogen or hydroxy or $R^{ac}$ together with $R^{ad}$ and the existing carbon to carbon bond forms a double bond, or $R^{ac}$ and $R^{ad}$ together form a diradical —$(CH_2)_j$— in which j is an integer from 1 to 5; or $R^{ab}$ and $R^{ac}$ together form a diradical —$(CH_2)_k$— in which k is an integer from 2 to 6, or $R^{ab}$ and $R^{ac}$ together are oxo or dialkylaminoalkyloxyimino of formula =N—O—$(CH_2)_q$—$NR^{ae}R^{af}$ in which q is the integer 2 or 3 and $R^{ae}$ and $R^{af}$ are independently hydrogen or (1–4C)alkyl, or the radical $NR^{ae}R^{af}$ is pyrrolidino, piperidino or morpholino; and $Z^a$ is nitrogen or a group $CR^{ad}$ in which $R^{ad}$ is hydrogen or $R^{ad}$ together with $R^{ac}$ and the existing carbon to carbon bond forms a double bond;

for a radical of formula Ib (in which Z denotes a nitrogen), $Z^b$ is a substituted imino group $R^{ba}N$ or $R^{ba}CH_2N$ in which $R^{ba}$ is (3–7C)cycloakyl, Ar or Het; or $Z^b$ is a disubstituted methylene group $R^{bb}(CH_2)_p$—C—$R^{bc}$ in which $R^{bb}$ is Ar or Het; p is the integer 0 or 1; and $R^{bc}$ is hydrogen, hydroxy, (1–4C)alkoxy, (1–4C)alkanoyloxy, $COOR^{bd}$ (wherein $R^{bd}$ is hydrogen or (1–3C)alkyl), cyano, $NR^{be}R^{bf}$ or $SR^{bg}$ in which $R^{be}$ and $R^{bf}$ are independently hydrogen, (1–4C)alkyl, (1–4C)hydroxyalkyl or (1–4C)alkanoyl, or the radical $NR^{be}R^{bf}$ is pyrrolidino, piperidino or morpholino; and $R^{bg}$ is hydrogen or (1–4C)alkyl; or $R^{bc}$ forms a double bond with the carbon atom to which it is bonded and with the adjacent carbon atom in the piperidine ring; or $Z^b$ is a disubstituted methylene group $R^{bh}CR^{bi}$ which forms a spirocyclic ring wherein $R^{bh}$ is phenyl which is joined by an ortho-substituent diradical $X^b$ to $R^{bi}$ in which the phenyl $R^{bh}$ may bear a further substituent selected from halo, (1–3C)alkyl, (1–3C)alkoxy, hydroxy, (1–3C)alkylthio, (1–3C)alkylsulfinyl and (1–3C)alkylsulfonyl; the diradical $X^b$ is methylene, carbonyl or sulfonyl; and $R^{bi}$ is oxy or imino of formula —$NR^{bj}$— in which $R^{bj}$ is hydrogen or (1–3C)alkyl;

for a radical of formula Ic (in which Z denotes a nitrogen), $R^{ca}$ is Ar or Het; and $Z^c$ is oxo, thio, sulfinyl, sulfonyl or imino of formula —$NR^{cb}$— in which $R^{cb}$ is (1–3C)alkyl or $R^{cc}R^{cd}N$—$(CH_2)_q$— in which q is the integer 2 or 3 and in which $R^{cc}$ and $R^{cd}$ are independently hydrogen or (1–3C)alkyl or the radical $R^{cc}R^{cd}N$ is pyrrolidino, piperidino or morpholino;

for a radical of formula Id (in which Z denotes a methine), $R^{da}$ is hydrogen, (1–6C)alkyl, Ar, Het, α-hydroxybenzyl, styryl, or $R^{db}$-(1–3C)alkyl in which $R^{db}$ is aryl, pyridyl, pyridylthio or 1-methyl-2-imidazolylthio in which an aromatic group or portion of $R^{da}$ may bear one or more halo, hydroxy, (1–4C)alkyl or (1–4C)alkoxy substituents; $X_d$ is oxy or —$CHR^{dc}$—; $R^{dc}$ is hydrogen, hydroxy, (1–3C)alkoxy, (1–4C)alkanoyloxy, $NR^{dd}R^{de}$ or (1–4C)alkanoylamino; $R^{dd}$ and $R^{de}$ are independently hydrogen or (1–4C)alkyl or the radical $NR^{dd}R^{de}$ is pyrrolidino, piperidino or morpholino; p is the integer 0 or 1; and $Z^d$ is a single bond (except when $R^{da}$ is hydrogen or p is 1), methylene or carbonyl;

for a radical of formula Ie (in which Z denotes a nitrogen), $J^e$ is oxygen, sulfur or $NR^{ea}$ in which $R^{ea}$ is hydrogen or (1–3C)alkyl; $R^{eb}$ is hydrogen, (1–6C)alkyl which may bear a hydroxy substituent and/or one to three fluoro substituents, (3–6C)alkenyl (in which a vinyl carbon is not bound to nitrogen), 2-hydroxyethyl, (3–7C)cyloalkyl, Ar or Het; $R^{ec}$ is hydrogen, (1–6C)alkyl which may bear a hydroxy substituent and/or one to three fluoro substituents, (3–6C)cycloalkyl, (1–5C)alkoxy (only when $J^e$ is oxygen), (3–6C)cycloalkoxy (only when $J^e$ is oxygen), or an amino group of formula $NR^{ed}R^{ee}$ containing zero to seven carbon atoms in which each of $R^{ed}$ and $R^{ee}$ is independently hydrogen, (1–5C)alkyl or (3–6C)cycloalkyl, or the radical $NR^{ed}R^{ee}$ is pyrrolidino, piperidino, morpholino, thiomorpholino (or its S-oxide) or piperazinyl (which piperazinyl group may bear a (1–3C)alkyl substituent at the 4-position);

for a radical of formula If (in which Z denotes a nitrogen), $J^f$ is oxygen, sulfur or $NR^{fa}$ in which $R^{fa}$ is hydrogen or (1–3C)alkyl; $L^f$ is a divalent hydrocarbon group in which the 1-position is bound to the carbon bearing the group $J^f$, the divalent group $L^f$ being selected from trimethylene, cis-propenylene, tetramethylene, cis-butenylene, cis-but-3-enylene, cis,cis-butadienylene, pentamethylene and cis-pentenylene which divalent group $L^f$ itself may bear one or two methyl substituents;

for a radical of formula Ig (in which Z denotes a nitrogen), $Z^g$ is (1–8C)alkyl or (3–8C)cycloalkyl which may bear one or more substituents selected from the group consisting of halo, (3–6C)cycloalkyl, cyano, nitro, hydroxy, (1–4C)alkoxy, (1–5C)alkanoyloxy, aroyl, heteroaroyl, oxo, imino (which may bear a (1–6C)alkyl, (3–6C)cycloalkyl, (1–5C)alkanoyl or aroyl substituent), hydroxyimino (which hydroxyimino may bear a (1–4C)alkyl or a phenyl substituent on the oxygen), an amino group of formula $NR^{ga}R^{gb}$, an amino group of formula $NR^{gc}R^{gd}$, an amidino group of formula $C(=NR^{gg})NR^{ge}R^{gf}$, and a carbamoyl group of formula $CON(OR^{gh})R^{gi}$, but excluding any radical wherein a hydroxy and an oxo substituent together form a carboxy group, wherein an amino group of formula $NR^{ga}R^{gb}$ contains zero to seven carbon atoms and each of $R^{ga}$ and $R^{gb}$ is independently hydrogen, (1–5C)alkyl or (3–6C)cycloalkyl, or the radical $NR^{ga}R^{gb}$ is pyrrolidino, piperidino, morpholino, thiomorpholino (or its S-oxide) or piperazinyl (which piperazinyl may bear a (1–3C)alkyl substituent group at the 4-position); and wherein $R^{gc}$ is hydrogen or (1–3C)alkyl and $R^{gd}$ is (1–5C)alkanoyl, aroyl or heteroaroyl; or $R^{gd}$ is a group of formula $C(=J^g)NR^{ge}R^{gf}$ in which $J^g$ is oxygen, sulfur, $NR^{gg}$ or $CHR^{gj}$; and wherein the amino group $NR^{ge}R^{gf}$ contains zero to seven carbon atoms and each of $R^{ge}$ and $R^{gf}$ is independently hydrogen, (1–5C) alkyl or (3–6C)cycloalkyl, or the radical $NR^{ge}R^{gf}$ is pyrrolidino, piperidino, morpholino, thiomorpholino (or its S-oxide) or piperazinyl (which piperazinyl may bear a (1–3C)alkyl substituent at the 4-position) or $R^{ge}$ is hydrogen or (1–4C)alkyl and $R^{gf}$ together with $R^{gg}$ forms an ethylene or trimethylene group; $R^{gg}$ is hydrogen, (1–4C)alkyl or together with $R^{gf}$ forms an ethylene or trimethylene group; $R^{gj}$ is cyano, nitro or $SO_2R^{gk}$ and $R^{gk}$ is (1–4C)alkyl or phenyl; $R^{gh}$ and $R^{gi}$ are independently (1–3C)alkyl; and in which a cyclic group which is a substituent on $Z^g$ or formed by substitution on $Z^g$ may bear one or more (1–3C)alkyl groups on carbon as further substituents; and in which any aryl or heteroaryl group which is a part of the group $Z^g$ may bear one or more halo, (1–4C)alkyl, (1–4C)alkoxy, cyano, trifluoromethyl or nitro substituents;

for a radical of formula Ih (in which Z denotes a nitrogen), $G^h$ denotes a single bond, a double bond or a divalent hydrocarbon radical; $J^h$ denotes a radical joined to the ring by a single bond if $G^h$ denotes a double bond or, otherwise, a radical joined by a double bond; $M^h$ denotes a heteroatom, a substituted heteroatom, or a single bond; and $L^h$ denotes a hydrocarbon radical in which the 1-position is attached to $M^h$; wherein the values of $G^h$, $J^h$, $M^h$ and $L^h$ are selected from (a) $G^h$ is a single bond; $J^h$ is oxo or thioxo; $M^h$ is oxy, thio or $NR^{ha}$; and $L^h$ is $L^{ha}$;

(b) $G^h$ is a single bond; $J^h$ is $NR^{hb}$; $M^h$ is $NR^{ha}$; and $L^h$ is $L^{ha}$;

(c) $G^h$ is a double bond, $J^h$ is $OR^{ha}$, $SR^{ha}$ or $NR^{hc}R^{hd}$; $M^h$ is nitrogen; and $L^h$ is $L^{ha}$;

(d) $G^h$ is methylene which may bear one or two methyl substituents; $J^h$ is oxo, thio or $NR^{he}$; $M^h$ is oxy, thio, sulfinyl, sulfonyl or $NR^{ha}$; and $L^h$ is $L^{hb}$;

(e) $G^h$ is a single bond; $J^h$ is oxo, thioxo or $NR^{he}$; $M^h$ is nitrogen; and $L^h$ is $L^{hc}$;

(f) $G^h$ is methine, which may bear a (1–3C)alkyl substituent; $J^h$ is oxo, thioxo or $NR^{he}$; $M^h$ is nitrogen; and $L^h$ is $L^{hd}$;

(g) $G^h$ is cis-vinylene, which may bear one or two methyl substituents; $J^h$ is oxo, thioxo, or $NR^{he}$; $M^h$ is nitrogen; and $L^h$ is $L^{he}$; and (h) $G^h$ is a single bond; $J^h$ is oxo or thioxo; $M^h$ is a single bond; and $L^h$ is $L^{hf}$; wherein $R^{ha}$ is hydrogen or (1–3C)alkyl; $R^{hb}$ is hydrogen, (1–3C) alkyl, cyano, (1–3C)alkylsulfonyl or nitro; $R^{hc}$ and $R^{hd}$ are independently hydrogen or (1–3C)alkyl or the radical $NR^{hc}R^{hd}$ is pyrrolidino, piperidino, morpholino, thiomorpholino (or its S-oxide) or piperazinyl (which piperazinyl may bear a (1–3C)alkyl substituent at the 4-position); $R^{he}$ is hydrogen or (1–3C)alkyl; $L^{ha}$ is ethylene, cis-vinylene, trimethylene or tetramethylene which radical $L^{ha}$ itself may bear one or two methyl substituents; $L^{hb}$ is ethylene or trimethylene which radical $L^{hb}$ itself may bear one or two methyl substituents; $L^{hc}$ is prop-2-en-1-yliden-3-yl, which radical $L^{hc}$ itself may bear one or two methyl substituents; $L^{hd}$ is cis-vinylene, which radical $L^{hd}$ itself may bear one or two methyl substituents; $L^{he}$ is methine, which radical $L^{he}$ itself may bear a (1–3C)alkyl substituent; and $L^{hf}$ is 4-oxabutan-1,4-diyl;

for a radical of formula Ij (in which Z denotes a nitrogen), $X^j$ is (1–6C)alkyl, $—CH_2OR^{ja}$, $—CH_2SR^{ja}$, $—CH_2S(O)R^{jg}$, $—CH_2S(O)_2R^{jg}$, $—COR^{ja}$, $—COOR^{ja}$, $—C(=J^{ja})NR^{jb}R^{jc}$, $—C(R^{ja})(OR^{jd})(OR^{je})$, $—CH_2N(R^{ja})C(=J^{ja})R^{jf}$, $—CH_2N(R^{ja})COOR^{jg}$ or $—CH_2N(R^{ja})C(=J^{ja})NR^{jb}R^{jc}$; $B^j$ is a direct bond and $L^j$ is a hydrocarbon chain in which the 1-position is bound to $B^j$ and $L^j$ is selected from trimethylene, tetramethylene, cis-1-butenylene and cis,cis-butadienylene; or $B^j$ is $N(R^{jh})$ and $L^j$ is a hydrocarbon chain selected from ethylene, trimethylene and cis-vinylene; or $B^j$ is N and $L^j$ is a hydrocarbon chain in which the 1-position is bound to $B^j$ and $L^j$ is cis,cis-prop-2-en-1-ylidin-3-yl; $J^j$ and $J^{ja}$ are independently oxygen or sulfur; $R^{ja}$, $R^{jf}$ and $R^{jh}$ are independently hydrogen or (1–6C)alkyl; $R^{jb}$ and $R^{jc}$ are independently hydrogen or (1–6C)alkyl; or the radical $NR^{jb}R^{jc}$ is pyrrolidino, piperidino, morpholino, thiomorpholino (or its S-oxide) or piperazinyl (which piperazinyl may bear a (1–3C)alkyl substituent at the 4-position); $R^{jd}$ and $R^{je}$ are independently (1–3C)alkyl or together form a divalent hydrocarbon chain selected from ethylene and trimethylene; $R^{jg}$ is (1–6C)alkyl; and for a radical of formula Ik (in which Z denotes a nitrogen), $Z^k$ is a nitrogen linked radical of formula II wherein $E^1$, $E^2$, $E^3$ and $E^4$ form a divalent four membered chain ($—E^1=E^2—E^3=E^4—$) in which each of $E^1$, $E^2$, $E^3$ and $E^4$ is methine; or in which one or two of $E^1$, $E^2$, $E^3$ and $E^4$ is nitrogen and the remaining $E^1$, $E^2$, $E^3$ and $E^4$ are methine; and further wherein one or more of $E^1$, $E^2$, $E^3$ and $E^4$ which is methine may bear a halo, (1–3C)alkyl, hydroxy, (1–3C) alkoxy, (1–3C)alkylthio, (1–3C)alkylsulfinyl or (1–3C) alkylsulfonyl substituent; and wherein the radicals $F^k$, $G^k$, and $I^k(X^k)$ are selected from (a) $G^k$ is a direct bond, $I^k(X^k)$ is a radical having the formula $=C(Z^k)—$ and $F^k$ is a radical selected from $—CH=$ and $—N=$;

(b) $G^k$ is a direct bond, $I^k(X^k)$ is a radical having the formula $—C(=J^k)—$ and $F^k$ is a radical selected from —N($R^{kf}$)—, —$CH_2$—$CH_2$—, —CH=CH—, —$CH_2$—N($R^{kf}$)— and —CH=N—;

(c) $G^k$ is a radical having the formula —$CH_2$—, $I^k(X^k)$ is a radical having formula —C(=$J^k$)— and $F^k$ is selected from —$CH_2$— and —N($R^{kf}$)—; and (d) $G^k$ is selected from —$CH_2$—, —$CH_2$—$CH_2$—, —CH=CH— and —N=CH—, $I^k(X^k)$ is a radical having the formula —C(=$J^k$)— and $F^k$ is a direct bond; wherein $J^k$ is oxygen or sulfur; $Z^k$ is —$OR^{ka}$, —$SR^{ka}$, —$COR^{ka}$, —$COOR^{ka}$, —C(=$J^{ka}$)$NR^{kb}R^{kc}$ or —C($R^{ka}$)($OR^{kd}$)($OR^{ke}$); $J^{ka}$ is oxygen or sulfur; $R^{ka}$ and $R^{kf}$ are independently hydrogen or (1–6C)alkyl; $R^{kb}$ and $R^{kc}$ are independently hydrogen or (1–6C)alkyl; or the radical $NR^{kb}R^{kc}$ is pyrrolidino, piperidino, morpholino, thiomorpholino (or its S-oxide) or piperazinyl (which piperazinyl may bear a (1–3C)alkyl substituent at the 4-position); $R^{kd}$ and $R^{ke}$ are independently (1–3C)alkyl or $R^{kd}$ and $R^{ke}$ together form ethylene or trimethylene; or $Z^k$ is an imido radical selected from phthalimido, succinimido, maleimido, glutarimido, and 3-oxa-, 3-thia- and 3-azaglutarimido, in which the imido radical may bear one or more (1–3C)alkyl substituents and, in addition, the aromatic portion of the phthalimido may bear one or more halo, hydroxy or (1–3C)alkoxy substituents; and wherein for a radical $Q^1$, Ar is a phenyl radical or an ortho-fused bicyclic carbocyclic radical of nine of ten ring atoms in which at least one ring is aromatic, which radical Ar may be unsubstituted or may bear one or more substituents selected from halo, cyano, trifluoromethyl, (1–4C)alkyl, (1–4C) alkoxy, methylenedioxy, hydroxy, mercapto, —S(O)$_n$$R^{xa}$, (1–5C)alkanoyl, (1–5C)alkanoyloxy, nitro, $NR^{xb}R^{xc}$, $NR^{xd}R^{xe}$, C(=$NR^{xf}$)$NR^{xg}R^{xh}$, $CONR^{xb}R^{xc}$ and $COOR^{xj}$ wherein n is the integer 0, 1, or 2; $R^{xa}$ is (1–6C)alkyl, (3–6C)cycloalkyl or phenyl (which phenyl may bear a halo, trifluoromethyl, (1–3C)alkyl or (1–3C)alkoxy substitutent); the radical $NR^{xb}R^{xc}$ contains zero to seven carbons and each of $R^{xb}$ and $R^{xc}$ is independently hydrogen, (1–5C)alkyl or (3–6C)cycloalkyl, or the radical $NR^{xb}R^{xc}$ is pyrrolidino, piperidino, morpholino, thiomorpholine (or its S-oxide) or piperazinyl (which piperazinyl may bear a (1–3C)alkyl substituent at the 4-position); and wherein $R^{xd}$ is hydrogen or (1–4C)alkyl and $R^{xe}$ is (1–5C)alkanoyl, benzoyl; or a group of formula C(=$J^x$)$NR^{xg}R^{xh}$ in which $J^x$ is oxygen, sulfur, $NR^{xf}$ or $CHR^{xi}$; $R^{xf}$ is hydrogen, (1–5C)alkyl or together with $R^{xg}$ forms an ethylene or trimethylene diradical, the radical $NR^{xg}R^{xh}$ contains zero to 7 carbons and each of $R^{xg}$ amd $R^{xh}$ is independently hydrogen, (1–5C)alkyl or (3–6C)cycloalkyl, or the radical $NR^{xg}R^{xh}$ is pyrrolidino, piperidino, morpholino, thiomorpholino (or its S-oxide) or piperazinyl (which piperazinyl may bear a (1–3C)alkyl substituent at the 4-position); or $R^{xg}$ together with $R^{xf}$ forms an ethylene or trimethylene diradical and $R^{xh}$ is hydrogen or (1–5C)alkyl; $R^{xi}$ is cyano, nitro, (1–5C)alkylsulfonyl or phenylsulfonyl; and $R^{xj}$ is hydrogen, (1–5C)alkyl or benzyl; and Het is a radical (or stable N-oxide thereof) attached via a ring carbon of a monocyclic aromatic ring containing five or six ring atoms consisting of carbon and one to four heteroatoms selected from oxygen, sulfur and nitrogen, or an ortho-fused bicyclic heterocycle derived therefrom by fusing a propenylene, trimethylene, tetramethylene or benz-diradical, which radical Het may be unsubstituted or may be substituted on carbon by one or more of the substituents defined above for Ar and may be substituted on nitrogen by (1–3C)alkyl;

$Q^2$ is a benzo-fused lactam radical selected from the group of radicals of formulae IIa, IIb, IIc, IId, IIe, IIf and IIg wherein J is oxygen or sulfur; $M^1$ is $CR^F$ or N; $M^2$ is methylene, ethylene, cis-vinylene, carbonyl or thiocarbonyl; $M^3$ is methylene, carbonyl, thiocarbonyl or sulfonyl; $M^4$ is carbonyl, thiocarbonyl or sulfonyl; and provided that one, and only one, of $M^3$ and $M^4$ in a radical of formula IIg is sulfonyl; $R^A$ is hydrogen or (1–3C)alkyl; the radicals $R^B$, $R^C$, $R^D$ and $R^E$ are each hydrogen; or one or more of $R^B$, $R^C$, $R^D$ and $R^E$ is a substituent independently selected from halo, trifluoromethyl, hydroxy, (1–3C)alkoxy, (1–3C)alkyl, (1–3C)alkylthio, (1–3C)alkylsulfinyl and (1–3C) alkylsulfonyl, and the others of $R^B$, $R^C$, $R^D$ and $R^E$ are each hydrogen; or two adjacent radicals of $R^B$, $R^C$, $R^D$ and $R^E$ form a methylenedioxy substitutent and the others of $R^B$, $R^C$, $R^D$ and $R^E$ are hydrogen; $R^F$ is hydrogen, hydroxy, (1–3C)alkoxy or (1–3C)alkyl $Q^3$ is hydrogen or (1–3C)alkyl; and $Q^4$ is phenyl which may bear one or two substituents independently selected from halo, trifluoromethyl, hydroxy, (1–3C)alkoxy, (1–3C)alkyl, methylenedioxy (1–3C) alkoxycarbonyl and (1–3C)alkylthio; or $Q^4$ is thienyl, imidazolyl, benzo[b]thiophenyl or naphthyl any of which may bear a halo substituent; or $Q^4$ is biphenylyl; or $Q^4$ is carbon-linked indolyl which may bear a benzyl substituent at the 1-position;

or (except when $Z^d$ is carbonyl) the N-oxide of a piperidino nitrogen indicated by Δ (or of either basic piperazinyl nitrogen of $Q^1$ when $Z^a$ is nitrogen);

or a pharmaceutically acceptable salt thereof;

or (except when $Z^d$ is carbonyl) a quaternary ammonium salt thereof in which the piperidino nitrogen indicated by Δ (or either basic piperazinyl nitrogen of $Q^1$ when $Z^a$ is nitrogen) is a quadricovalent ammonium nitrogen wherein the fourth radical on the nitrogen $R^1$ is (1–4C)alkyl or benzyl and the associated counterion A is a pharmaceutically acceptable anion.

A subgroup of the invention is a compound of formula III, or a pharmaceutically acceptable salt thereof, wherein $Q^{1a}$ is a radical of formula $Q^1$ defined above for a compound of formula I in which Z denotes a nitrogen and $Q^{2a}$ is a radical of formula IIa or IIb defined above for a compound of formula I.

Another subgroup of the invention is a compound of formula I wherein $Q^4$ is phenyl which may bear one or two substituents independently selected from halo, trifluoromethyl, hydroxy, (1–3C)alkoxy, (1–3C)alkyl and methylenedioxy; or $Q^4$ is thienyl, imidazolyl, benzo[b] thiophenyl or naphthyl any of which may bear a halo substituent; or $Q^4$ is biphenylyl; or $Q^4$ is carbon-linked indolyl which may bear a benzyl substituent at the 1-position; or (except when $Z^d$ is carbonyl) the N-oxide of a piperidino nitrogen indicated by Δ (or of either basic piperazinyl nitrogen of $Q^1$ when $Z^a$ is nitrogen); or a pharmaceutically acceptable salt thereof; or (except when $Z^d$ is carbonyl) a quaternary ammonium salt thereof in which the piperidino nitrogen indicated by A (or either basic piperazinyl nitrogen of $Q^1$ when $Z^a$ is nitrogen) is a quadricovalent ammonium nitrogen wherein the fourth radical on the nitrogen $R^1$ is (1–4C)alkyl or benzyl and the associated counterion A is a pharmaceutically acceptable anion.

It will be appreciated that a compound of formula I (or III) contains one or more asymmetrically substituted carbon atoms such that such a compound may be isolated in optically active, racemic and/or diastereomeric forms. A compound may exhibit tautomerization. A compound may exhibit polymorphism. It is to be understood that the present invention encompasses any racemic, optically-active, diastereomeric, tautomeric, polymorphic or stereoisomeric form, or mixture thereof, which form possesses NK2 antagonist properties, it being well known in the art how to prepare optically-active forms (for example, by resolution of the racemic form or by synthesis from optically-active starting materials) and how to determine the NK2 antagonist properties by the standard tests described hereinafter. It may be preferred to use the compound of formula I (or III) in an optically pure form which is characterized as containing, for example, at least 95%, 98% or 99% enantiomeric excess of a particular form. For example, it may be preferred to use the compound of formula I (or III), or a particular diastereomer thereof, in a form which is characterized as containing at least 95%, 98% or 99% enantiomeric excess of the form with the (R)- or the (S)-configuration at the center indicated by * in the formulae.

In this specification $R^{aa}$, $R^{ab}$, $R^A$, $R^B$, $R^1$, $R^2$, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl (except where more specifically defined) denotes a phenyl radical or an ortho-fused bicyclic carbocyclic radical having about nine to ten ring atoms in which at least one ring is aromatic. Heteroaryl (except where more specifically defined) encompasses a radical attached via a ring carbon of a monocyclic aromatic ring containing five ring atoms consisting of carbon and one to four heteroatoms selected from oxygen, sulfur and nitrogen or containing six ring atoms consisting of carbon and one or two nitrogens, as well as a radical of an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof. Aroyl is arylcarbonyl; heteroaroyl is heteroarylcarbonyl.

A pharmaceutically acceptable salt is one made with an acid which provides a physiologically acceptable anion.

Particular values are listed below for radicals or portions thereof (for example, particular values for (1–3C)alkyl provide particular values for the alkyl portion of (1–3C)alkoxy or (1–3C)alkylsulfinyl), substituents and ranges for a compound of formula I or formula III as described above for illustration only and they do not exclude other defined values or other values within defined ranges for the radicals and substituents.

A particular value for Ar is phenyl which may be unsubstituted or may bear a chloro, methyl, methoxy, hydroxy or methylsulfinyl substituent. A particular value for Het is furyl, thienyl, 2-imidazolyl, 1,3,4-oxadiazol-2-yl, pyridyl or pyrimidinyl which ring may be unsubstituted or may bear a chloro, methyl, methoxy, hydroxy, methylsulfinyl, methoxycarbonyl or ethoxycarbonyl substituent. A particular value for aryl is phenyl. A particular value for heteroaryl is furyl, pyridyl or pyrimidinyl. A particular value for halo is chloro or bromo. A particular value for (1–3C)alkyl is methyl, ethyl, propyl or isopropyl; for (1–4C)alkyl is methyl, ethyl, propyl, isopropyl, butyl, isobutyl or t-butyl; for (1–5C)alkyl is methyl, ethyl, propyl, isopropyl, butyl, isobutyl, t-butyl, pentyl or isopentyl; for (1–6C)alkyl is methyl, ethyl, propyl, isopropyl, butyl, isobutyl, t-butyl, pentyl, isopentyl, hexyl or isohexyl; and for (1–8C)alkyl is methyl, ethyl, propyl, isopropyl, isopentyl, 1-ethylpropyl, hexyl, isohexyl, 1-propylbutyl, or octyl. A particular value for (3–6C)cylcoalkyl is cyclopropyl, cyclopentyl or cyclohexyl; for (3–7C)cycloalkyl is cyclopropyl, cyclopentyl, cyclohexyl or cycloheptyl; and for (3–8C)cycloalkyl is cyclopropyl, cyclopentyl, cyclohexyl, cycloheptyl or cyclooctyl. A particular value for (3–6C)alkenyl is allyl, 2-butenyl or 3-methyl-2-butenyl. A particular value for (1–4C)alkanoyl is formyl, acetyl, propionyl, butyryl or isobutyryl; and for (1–5C)alkanoyl is formyl, acetyl, propionyl, butyryl, isobutyryl, valeryl, isovaleryl or pivaloyl.

A more particular value for Ar is phenyl which may be unsubstituted or may bear a methoxy, hydroxy or methylsulfinyl substituent. A more particular value for Het is pyridyl or pyrimidinyl which ring may be unsubstituted or may bear a methoxy, hydroxy or methylsulfinyl substituent. A more particular value for heteroaryl is pyridyl. A more particular value for halo is chloro. A more particular value for (1–3C)alkyl is methyl; for (1–4C)alkyl is methyl or ethyl; for (1–5C)alkyl is methyl, ethyl, propyl or isopropyl; for (1–6C)alkyl is methyl, ethyl, propyl, isopropyl, butyl, isobutyl or t-butyl; and for (1–8C)alkyl is methyl, ethyl, propyl, isopropyl, 1-ethylpropyl or 1-propylbutyl. A more particular value for (3–6C)cylcoalkyl is cyclopropyl or cyclopentyl; for (3–7C)cycloalkyl is cyclopropyl or cyclopentyl; and for (3–8C)cycloalkyl is cyclopropyl, cyclopentyl, cyclohexyl or cycloheptyl. A more particular value for (3–6C)alkenyl is allyl. A more particular value for (1–4C)alkanoyl is formyl or acetyl; and for (1–5C)alkanoyl is formyl, acetyl, propionyl, butyryl or isobutyryl.

A particular group of compounds is one in which $J^e$, $J^f$, $J^g$, $J^i$, $J^{ja}$, $J^k$ and $J^{ka}$ are oxygen and $J^h$ is oxo; $M^1$ is CH or N; $M^2$ is methylene or carbonyl; $M^3$ is methylene, carbonyl or sulfonyl; $M^4$ is carbonyl or sulfonyl; $R^A$ is hydrogen methyl or ethyl; $R^B$, $R^C$, $R^D$ and $R^E$ are each hydrogen, or one of $R^B$, $R^C$, $R^D$ and $R^E$ is methoxy, hydrogen, methylthio, methylsulfinyl or methylsulfonyl and the others of $R^B$, $R^C$, $R^D$ and $R^E$ are hydrogen; $Q^3$ is hydrogen and $Q^4$ is phenyl which may bear one or two substituents selected from halo, trifluoromethyl and methylenedioxy.

A particular value for $Q^1$ is 4-benzylpiperidino, 4-(3-methoxyphenyl)piperidino, 4-(2-methylsulfinylphenyl)piperidino, 4-(2-pyridyl)piperidino, 4-(3-pyridyl)piperidino, 4-(2-methylsulfinylpyrid-3-ylpiperidino, 4-hydroxy-4-phenylpiperidino, 4-acetamido-4-phenylpiperidino, 4-(N-phenylacetamido)piperidino, 4-(2-hydroxyethyl)piperidino, 4-(1-hydroxy-1-propylbutyl)piperidino, 4-(2-oxopyrrolidin-1-yl)piperidino, 4-(2-oxopiperidino)piperidino, 4-(2-thioxopiperidino)piperidino, 4-(2-oxoperhydropyrimidin-1-yl)piperidino, 4-ethoxycarbonyl-4-(2-oxopiperidino)piperidino, 4-methoxycarbonyl-4-(2-oxoperhydropyrimidin-1-yl)piperidino, 4-(1-oxoisoindolin-2-yl)piperidino, 4-(2-oxo-2,3-dihydrobenzimidazol-1-yl)piperidino or 4-(2-oxo-1,2,3,4-tetrahydroquinazolin-3-yl)piperidino.

A more particular value for $Q^1$ is 4-(2-methylsulfinylphenyl)piperidino.

A particular value for $Q^2$ is, for example, a radical of formula IIa, and IIb, IIc or IIg, and more particularly wherein J is oxygen and $M^4$ is carbonyl. A more particular value for $Q^2$ is a radical of formula IIa or IIb, and more particularly wherein J is oxygen, $M^1$ is CH or N, and $R^A$ is methyl.

A particular value for $Q^3$ is hydrogen.

A particular value for $Q^4$ is, for example, 3,4-dichlorophenyl or 3,4-methylenedioxyphenyl.

A particular value for $R^1$ is methyl or benzyl and for A is, for example, chloride, bromide or methanesulfonate.

A particular group of compounds of formula III is one in which $Q^{1a}$ is a radical of formula If, Ih or Ig and wherein J is oxygen and $M^1$ is CH or N, in which the radicals and substituents may have any of the values, particular values or more particular values defined above; or a pharmaceutically acceptable salt thereof.

A further particular group of compounds of formula I or formula III is one in which $Q^1$ (or $Q^{1a}$) is selected from the values listed above as a particular value for $Q^1$;

$Q^2$ is formula IIa wherein J is oxygen; $M^1$ is CH; $R^A$ is (1–3C)alkyl; $R^B$, $R^C$, $R^D$ and $R^E$ are each hydrogen or $R^C$ is methoxy and $R^B$, $R^C$ and $R^D$ are hydrogen;

Q3 is hydrogen; and $Q^4$ is 3,4-dichlorophenyl;

or a pharmaceutically acceptable salt thereof.

Within that group of compounds it is preferred that the center indicated by * in formula I and formula III be of the (S)-configuration and that the adjacent carbon (the 3-carbon of the 2,3-dihydroisoindol-1-one moiety) be of the (R)-configuration.

In general, for a compound of formula I or formula III, it is preferred that the sterochemistry correspond to that identified above, although the designation of an asymmetric center as (R)- or (S)- may vary with the particular molecule owing to the sequence rules for nomenclature.

Specific compounds of formula I (and of formula III) are described in the accompanying Examples.

Pharmaceutically acceptable salts of a compound of formula I (or of formula III) include those made with a strong inorganic or organic acid which affords a physiologically acceptable anion, such as, for example, hydrochloric, sulfuric, phosphoric, methanesulfonic, or para-toluenesulfonic acid.

A compound of formula I (or of formula III) may be made by processes which include processes known in the chemical art for the production of structurally analogous heterocyclic compounds. Such processes and intermediates for the manufacture of a compound of formula I (or of formula III) as defined above are provided as further features of the invention and are illustrated by the following procedures in which the meanings of generic radicals are as defined above unless otherwise indicated:

(a) For a compound of formula I in which Z denotes a nitrogen (or for a compound of formula III), alkylating a piperidine of formula IIIa (wherein $Q^{1a}$ is a radical of formula $Q^1$ defined above for a compound of formula I in which Z denotes a nitrogen) with an aldehyde of formula IV (or of formula IVa), by reductive alkylation. The alkylation is preferably carried out by a conventional reductive alkylation, for example as described in Example 1, by the in situ, acid-catalyzed formation of an imminum salt, followed by reduction with sodium cyanoborohydride in alcoholic solvent.

(b) Alkylating a piperidine of formula IIIa with an alkylating agent of formula V (or of formula Va) in which Y is a leaving group. Typical values for Y include for example, iodide, bromide, methanesulfonate, p-toluenesulfonate, trifluoromethane-sulfonate, and the like. The reaction may be carried out under standard conditions, for example in a suitable solvent at a temperature in the range of −20 to 100° C., preferably in the range of 0 to 50° C.

(c) For an N-oxide of the piperidino nitrogen indicated by Δ of a compound of formula I (or of formula III), oxidizing the piperidino nitrogen indicated by Δ of a compound of formula I using a conventional procedure, such as, for example, using hydrogen peroxide in methanol, peracetic acid, 3-chloroperoxybenzoic acid in an inert solvent (such as dichloromethane) or dioxirane in acetone.

(d) For a quaternary ammonium salt of the piperidino nitrogen indicated by Δ of a compound of formula I (or of formula III), alkylating the piperidino nitrogen indicated by Δ of the compound of formula I (or of formula III) with an alkylating agent of formula $R^1Y$ or alkylating a piperidine of formula IIIb with an alkylating agent of formula V, wherein Y is a leaving group, followed, if required, by exchanging the counterion Y for a different counterion A by a conventional method. Typical values for Y include those listed above. Exchange of counterions may conveniently be carried out using a basic ion exchange resin in the "A" form.

(e) For a compound of formula I in which $Q^1$ is of formula Id, reducing the double bond of a corresponding starting material of formula VI using a conventional method.

(f) For a compound of formula I in which $Q^1$ is of formula Id, substituting the nitrogen of a compound of formula VIa with a radical of formula $R^{da}$—$(X^d)p$—$Z^d$— using a conventional method.

(g) For a compound of formula I (or of formula III) which bears a sulfinyl group, oxidizing the sulfur of a corresponding compound of formula I (or of formula III) which bears a sulfide group using a conventional method.

(h) For a compound of formula I (or of formula III) which bears a sulfonyl group, oxidizing a sulfide or sulfinyl group of a corresponding compound of formula I (or of formula III) using a conventional method.

(i) For a compound of formula I (or of formula III) which bears an aromatic hydroxy group, cleaving the ether of a corresponding compound of formula I (or of formula III) which bears an aromatic alkoxy group using a conventional method.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. Such reactions and modifications include, for example, introduction of nitro or halogeno and reduction of nitro. The reagents and reaction conditions for such procedures are well known in the chemical art.

If not commercially available, the necessary starting materials for the above procedures may be made by procedures which are selected from standard techniques of heterocyclic chemistry, techniques which are analogous to the synthesis of known, structurally similar compounds (particularly those described in the above noted EPA publications and their counterparts), and techniques which are analogous to the above described procedures or the procedures described in the Examples. The starting materials and the procedures for their preparation are additional aspects of the invention.

In Schemes I and II are outlined general synthetic routes for the preparation of starting materials of formulae IV and V (or corresponding compounds of formulae IVa and Va). Thus, an arylacetic acid of formula X in which $R^2$ is hydroxy, a corresponding ester of formula X in which $R^2$ is, for example, methoxy or ethoxy, or an amide of formula X (such as the chiral amide in which $R^2$ is (R)- or (S)-4-benzyl-2-oxopyrrolidin-1-yl) may be alkylated with a compound of formula $R^3CH_2Y$ in which $R^3$ is a protected or latent hydroxymethyl or formyl radical, for example tetrahydropyran-2-yloxymethyl, vinyl, or dimethoxymethyl (or other acetal), and Y is a leaving group, as described above, to afford a substituted acid derivative of formula XI (or a substituted derivative of formula XII wherein $Q^3$ is hydrogen). For a compound of formula XII in which $Q^3$ is not hydrogen, an acid derivative of formula XI may be alkylated further with an alkylating agent of formula $Q^3Y$. Alternatively, a compound of formula X first may be alkylated with an alkylating agent of formula $Q^3Y$ to afford a substituted drivative of formula XIII, followed by alkylation with a compound of formula $R^3CH_2Y$ to afford a substituted ester derivative of formula XII. It may be convenient or preferred to prepare an intermediate compound of formula XII in an optically pure form at the center indicated by * using a conventional method, such as resolving an acid of formula XII in which $R^2$ is hydroxy or by alkylating the amide of a chiral amine, such as the one described above.

The radical —$COR^2$ of a compound of formula XII then may be converted into a benzo-fused lactam radical $Q^2$. For a compound in which $Q^2$ is a carbon-linked radical, the carbonyl carbon of formula XII conveniently becomes the carbon of $Q^2$ bonded to the carbon indicated by * in the structure formulae. For example, for a ring system of formula IIa or IIb in which J is oxygen and $M^1$ is CH, an ester of formula XII or the corresponding N-methoxy-N-methyl amide of formula XII may be condensed with a dimetallated benzamide or o-toluamide, such as the lithium derivatives described in Examples 1–7 or the corresponding dichlorocerium or dichlorolanthanum derivatives, and further elaborated to form the ring $Q^2$. It may be preferred to use zinc iodide and sodium cyanoborohydride in the reduction described in Example 2.c to obtain a single diasteromer. (It will be recognized that the ketone initially formed in Example 2.b may reversibly cyclize to afford an isomeric 3-hydroxy-2-methyl-2,3-dihydroisoindole-1-one.) For a compound in which $Q^2$ is a nitrogen-linked radical, an acid derivative of formula XII may be converted into the corresponding amine of formula XVI and the nitrogen of the amine then incorporated into the radical $Q^2$ (An amine of formula XVI also may be prepared by alkylation of a nitro compound of formula $Q^4CH_2NO_2$, followed by reduction of the nitro group.) Alternatively, particularly when $Q^3$ is hydrogen, a compound of formula XVII wherein Y is a leaving group, as described above, may be used to alkylate the anion derived from the deprotonation of a compound of formula $Q^2$—H (or formed by a different method) to directly afford a compound of formula XIV.

An intermediate of formula XIV may be converted into a starting material aldehyde of formula IV (or formula IVa) by conversion of the group $R^3$ into a formyl group, for example by the oxidative cleavage of a compound in which $R^3$ is vinyl or hydrolysis of the acetal when $R^3$ is dimethoxymethyl. Alternatively, for a compound of formula XIV in which $R^3$ is a protected hydroxymethyl, deprotection of the alcohol affords an alcohol of formula XV. The alcohol of formula XV may be oxidized to afford an aldehyde of formula IV (or formula IVa), or the hydroxy group may be converted into a leaving group Y by using a conventional method to afford a starting material of formula V (or formula Va). An alcohol of formula XV may be oxidized to the aldehyde of formula IV (or formula IVa), for example using oxalyl chloride, dimethyl sulfoxide and triethylamine as described in Example 1.f or using Dess-Martin periodinane (1,1,1-triacetoxy-1,1-dihydro-1,2-benziodoxol-3(1H)-one).

For the preparation of a starting material piperidine of formula IIIa, a 1-protected 4-piperidone or a 1-protected 4-aminopiperidine is typically a convenient starting material for elaboration into the requisite substituted piperidine using a conventional method, followed by deprotection of the piperidino nitrogen. When a compound of formula IIIa containing a thiocarbonyl group is required, it conveniently may be obtained from a corresponding 1-protected piperidine intermediate containing a carbonyl group oxygen by treatment with phosphorous pentasulfide or with Lawesson's reagent, 2,4-bis(4-methoxyphenyl)-1,3-dithia-2,4-diphosphetane-2,4-disulfide, followed by deprotection of the piperidino nitrogen.

A starting material piperidine of formula IIIb may be obtained from a piperidine of formula IIIa by reductive alkylation to introduce the substutient $R^1$, or the compound may be prepared in a manner analogous to the preparation of a piperidine of formula IIIa.

A starting material of formula VI may be prepared from a corresponding ketone of formula VIb by a conventional method, for example by condensation with a a compound of formula VIc in which $R^{dx}$ and $R^{dy}$ together form a triphenylphosphoranylidene radical or with the anion obtained by deprotonation of a compound of formula VIc wherein $R^{dx}$ is a dimethylphosphono radical and $R^{dy}$ is hydrogen. A compound of formula VIc may be obtained from a compound of formula V using a conventional method. A starting material of formula VIa may be prepared analogously from a 1-protected 4-pyridone, followed by reduction and deprotection.

As will be clear to one skilled in the art, a variety of sequences is available for preparation of the starting materials, and the sequences leading to the starting materials and products of the invention may be altered if appropriate considerations regarding the synthetic methods and radicals present are followed.

The utility of a compound of the invention or a pharmaceutically acceptable salt thereof (hereinafter, collectively referred to as a "Compound") may be demonstrated by standard tests and clinical studies, including those disclosed in the EPA publications noted above, such as EPA 428434 or EPA 474561 (or U.S. Pat. No. 5,236,921), and those described below.

Neurokinin A (NKA) Receptor-binding Assay (Test A)

The ability of a Compound of the invention to antagonize the binding of NKA at the NK2 receptor may be demonstrated using an assay using the human NK2 receptor expressed in Mouse Erythroleukemia (MEL) cells, as described in: Aharony, D., Little, J., Thomas, C., Powell, S., Berry, D. and Graham, A. Isolation and Pharmacological Characterization of a Hampster Neurokinin A Receptor cDNA, *Molecular Pharmacology,* 1994, 45, 9–19. In an initial use of this assay, the $IC_{50}$ measured for the standard compound L-659,877 was found to be 30 nM versus $^3$H-NKA binding to MEL.

The selectivity of a Compound for binding at the NK2 receptor may be shown by determining its binding at other receptors using standard assays, for example, one using a tritiated derivative of SP in a tissue preparation selective for NK1 receptors or one using a tritiated derivative of NKB in a tissue preparation selective for NK3 receptors.

Guinea Pig Assay (Test B)

The ability of a Compound of the invention to antagonize the action of an agonist, either NKA or [β-ala$^8$]-NKA(4–10), in a pulmonary tissue may be demonstrated using a functional assay in guinea pig trachea, which is carried out as follows. The chosen agonist is refered to as AG throughout the description.

Male guinea pigs are killed by a sharp blow to the back of the head. The trachea are removed, trimmed of excess tissue and divided into two segments. Each segment is suspended as a ring between stainless steel stirrups in water-jacketed (37.5° C.) tissue baths containing a physiological salt solution of the following composition (mM): NaCl, 119; KCl 4.6; CaCl$_2$, 1.8; MgCl$_2$, 0.5; NaH$_2$PO$_4$, 1; NaHCO$_3$, 25; glucose, 11; thiorphan, 0.001; and indomethacin, 0.005; gassed continuously with 95% $O_2$–%5 $CO_2$. Initial tension placed on each tissue is 1 g, which is maintained throughout a 0.5 to 1.5 hour equilibration period before addition of other drugs. Contractile responses are measured on a Grass polygraph via Grass FT-03 force transducers.

Tissues are challenged repetitively with a single concentration of AG (10 nM) with intervening 30 min periods with washing to allow the tension to return to baseline levels. The magnitude of the contractions to AG reaches a constant level after two challenges, and each Compound is tested for inhibition of responses to AG by addition to the tissue bath 15 minute before the third or subsequent exposure to the agonist. The contractile response to AG in the presence of Compound is compared to that obtained with the second AG challenge (in the absence of Compound). Percent inhibition is determined when a Compound produces a statistically significant ($p<0.05$) reduction of the contraction and is calculated using the second contractile response as 100%.

Potencies of selected Compounds are evaluated by calculating apparent dissociation constants ($K_B$) for each concentration tested using the standard equation:

$$K_B = [\text{antagonist}]/(\text{dose ratio}-1)$$

where dose ratio=antilog[(AG —log molar EC$_{50}$ without Compound)—(AG —log molar EC$_{50}$ with Compound)]. The $K_B$ values may be converted to the negative logarithms and expressed as —log molar $K_B$ (i.e. p$K_B$). For this evaluation, complete concentration-response curves for AG are obtained in the absence and presence of Compound (30 min incubation period) using paired tracheal rings. The potency of AG is determined at 50% of its own maximum response level in each curve. The EC$_{50}$ values are converted to the negative logarithms and expressed as —log molar EC$_{50}$. Maximum contractile responses to AG are determined by expressing the maximum response to AG as a percentage of the contraction caused by carbachol (30 μM), added after the initial equilibration period. When a statistically significant ($p<0.05$) reduction of the maximum response to AG is produced by a compound, the percent inhibition is calculated relative to the percentage of carbachol contraction in the untreated, paired tissue used as 100%.

Guinea Pig Labored Abdominal Breathing (Dyspnea) Assay (Test C)

Activity of a Compound of the invention as an antagonist of NKA at the NK2 receptor also may be demonstrated in vivo in laboratory animals, for example by adapting a routine guinea pig aerosol test described for evaluation of leukotriene antagonists by Snyder, et al. (Snyder, D. W., Liberati, N. J. and McCarthy, M. M., Conscious guinea-pig aerosol model for evaluation of peptide leukotriene antagonists. *J. Pharmacol. Meth.* (1988) 19, 219). Using the clear plastic chamber described previously by Snyder et al. to secure guinea pigs for a head-only aerosol exposure to bronchoconstrictor agonists, agonist is administered by aerosol to six conscious guinea pigs simultaneously during each maneuver. The tachykinin NK2-selective agonist, [β-ala$^8$]—NKA(4–10), $3\times10^{-5}$ M, is aerosolized from a Devilbiss Model 25 ultrasonic nebulizer into an air stream entering the chamber at a rate of 2 L/minute.

Guinea pigs (275–400 g) are fasted for approximately 16 hours prior to experimentation. Compounds to be evaluated for blockade of effects of [β-ala$^8$]—NKA(4–10) or their vehicle (10% PEG400 in saline) are administered p.o. or i.v. at various times before aerosol agonist challenge. All animals are pretreated with atropine (10 mg/kg, i.p., 45 minutes pretreatment) indomethacin (10 mg/kg, i.p., 30 minutes pretreatment), propranolol (5 mg/kg, i.p., 30 minutes pretreatment), and thiorphan (1 mg/ml aerosol for 5 minutes, 15 minutes pretreatment).

Aerosol challenge with the agonist produces an initial increase in respiratory rate followed by a decrease with early signs of minor involvement of the abdominal muscles. The respiratory rate decreases further and the breathing becomes more labored with greater involvement of the abdominal muscles as exposure continues. The distinctly recognizable end point is the point where the breathing pattern of the guinea pig is consistently slow, deep, and deliberate, showing marked involvement of the abdominal muscles. Time, in seconds, from the onset of aerosol challenge to this end point is determined for each animal by using a stopwatch. The animals generally collapse after reaching the end point and donot recover from the agonist-induced respiratory distress. Antagonists result in an increase in the time to reach the end point. Animals receive the aerosol administration of agonist for a maximum time of 780 seconds.

Differences between drug treated groups and corresponding vehicle treated control groups are compared using Student's t-test for unpaired observations.

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, FEV$_1$ (forced expiratory volume in one second) and FVC (forced vital capacity), analyzed by standard methods of statistical analysis.

It will be appreciated that the implications of a Compound's activity in Test A or Test B is not limited to asthma, but rather, that the test provides evidence of general antagonism of NKA. In general, the Compounds of the invention which were tested demonstrated statistically significant activity in Test A with a $K_i$ of 1 μM or much less. For example, the compound described in Example 4 was typically found to have a $K_i$ of 3.5 nM. In Test B, a p$K_B$ of 5 or greater was typically measured for a Compound of the invention. For example, a p$K_B$ of 7.7 was measured for the compound described in Example 4. It should be noted that there may not always be a direct correlation between the activities of Compounds measured as $K_i$ values in Test A and the values measured in other assays, such as the p$K_B$ measured in Test B.

As discussed above, a compound of formula I or a pharmaceutically acceptable salt thereof possesses NKA antagonist properties. Accordingly, it antagonizes at least one of the actions of NKA which are known to include bronchoconstriction, increased microvascular permeability, vasodilation and activation of mast cells. Accordingly, one feature of the invention is the use of a compound of formula I or a pharmaceutically acceptable salt thereof in the treatment of a disease in a human or other mammal in need thereof in which NKA is implicated and antagonism of its action is desired, such as for example the treatment of asthma or a related disorder. In addition, another feature of the invention is provided by the use of a compound of formula I or a salt thereof as a pharmacological standard for the development and standardization of new disease models or assays for use in developing new therapeutic agents for treating the diseases in which NKA is implicated or for assays for their diagnosis.

When used in the treatment of such a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (°C.); operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; reversed phase chromatography means chromatography over octadecylsilane (ODS) coated support having a particle diameter of 32–74 $\mu$, known as "PREP-40-ODS" (Art 731740-100 from Bodman Chemicals, Aston, Pa., USA); thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; for AB spectra the directly observed shifts are reported; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the electron impact (EI) mode using a direct exposure probe; where indicated ionization was effected by chemical ionization (CI) or fast atom bombardment (FAB); values for m/z are given; generally, only ions which indicate the parent mass are reported.

EXAMPLE 1

3-[1-(3,4-Dichlorophenyl)-3-(4-hydroxy-4-phenylpiperidino)propyl]-2-methyl-2,3-dihydroisoindol-1-one hydrochloride A solution of 3-(3,4-dichlorophenyl)-3-(2-methyl-3-oxo-2,3-dihydro-1H-isoindol-1-yl)propionaldehyde (0.112 g) in methanol (5 mL) was treated with 4-hydroxy-4-phenylpiperidine (0.057 g) and the pH was adjusted to 6 by adding acetic acid. After treating with sodium cyanoborohydride (0.030 g), the reaction mixture was stirred at ambient temperature for 16 hours, diluted with a saturated solution of sodium bicarbonate, and extracted with dichloromethane. The organic layers were dried and evaporated to obtain 3-[1-(3,4-dichlorophenyl)-3-(4-hydroxy-4-phenylpiperidino)propyl]-2-methyl-2,3-dihydroiso-indol-1-one as a foam (0.104 g). This material was transformed into the hydrochloride salt as follows. The above product was dissolved in dry dichloromethane (2 mL) and treated with HCl in ether (2 mL). The resulting solution was diluted with anhydrous ether, stirred for 2 hours and the resulting precipitate was collected to afford the title compound (0.075 g); mp 160° C. (dec); MS: m/z=509(M+1); NMR: 1.79 (broad, 2), 3.32 (s,3), 3.75 (broad,1), 4.88 (m,1), 5.44 (s,1), 6.80–7.95 (m,12). Analysis for $C_{29}H_{30}Cl_2N_2O_2 \cdot HCl \cdot 0.5 H_2O$: Calculated: C, 62.76; H, 5.81; N, 5.13; Found: C, 62.79; H, 5.89; N, 4.89.

The intermediate 3-(3,4-dichlorophenyl)-3-(2-methyl-3-oxo-2,3-dihydro-1H-isoindol-1-yl)propionaldehyde was synthesized as follows:

a. Ethyl 3,4-dichlorophenylacetate. A solution of 3,4-dichlorophenylacetic acid (39 g) in ethanol (300 mL) was treated with concentrated sulfuric acid (15 mL) and refluxed for 16 hours. The reaction mixture was cooled to the room temperature, diluted with water and ether. The organic layer was washed (water and saturated sodium bicarbonate solution), dried and evaporated to afford the ester (44.27 g); MS: m/z=233(M+1); NMR: 1.2 (t,3, J=4), 3.76 (s,2), 4.09 (q,2, J=4), 7.28 (dd,1, J=5, 1) 7.57 (m,2).

b. 2-(3,4-Dichlorophenyl)-4-(tetrahydropyran-2-yloxy) butyric acid ethyl ester. A solution of ethyl 3,4-dichlorophenylacetate (23.3 g) in tetrahydrofuran (50 mL) was treated with sodium hydride (4.0 g of 60% dispersion in oil) and the suspension was stirred at room temperature for 1.5 hours. The reaction mixture was cooled to 0° C. and treated with a solution of 1-bromo-2-(tetrahydropyran-2-yloxy)ethane (20.9 g) in tetrahydrofuran (50 mL). Upon stirring at ambient temperature for 16 hours, the reaction mixture was treated with saturated ammonium chloride solution, ether, sodium chloride solution and sodium bicarbonate solution. The organic layer was separated and the aqueous layer was extracted with ether. The combined organic extracts were washed with sodium bicarbonate solution, dried and evaporated to obtain an oil. Chromatography, eluting with dichloromethane, afforded the ether (5.87 g); MS: m/z=277(M-84); NMR: 1.14 (t,3, J=7), 1.94 (m,1), 2.27 (m,1), 3.62 (m,2), 3.80 (m,1), 4.08 (m,2), 4.48 (m,1), 7.31 (m,1), 7.59 (m,2).

c. 2-[2-(3,4-Dichlorophenyl)-4-(tetrahydropyran-2-yloxy)-butyryl]-N-methylbenzamide. A solution of N-methylbenzamide (0.406 g) in tetrahydrofuran (10 mL) was cooled to 0° C. and treated with n-butyl lithium (2.4 mL of 2.5M solution) and the resulting yellow solution was stirred at 0° C. for 30 minutes. At the end of this period, this yellow solution was transferred, under nitrogen, using a cannula, to a solution of 2-(3,4-dichlorophenyl)-4-(tetrahydropyran-2-yloxy)butyric acid ethyl ester (1.08 g) in tetrahydrofuran (10 mL) at −78° C. The resulting reaction mixture was allowed to warm to the room temperature slowly. After 30 minutes, the reaction mixture was treated with saturated ammonium chloride solution, extracted with ether. The organic layer was dried and evaporated to obtain an oil. Chromatography, eluting with hexane and isopropanol (20:1, 9:1), afforded the amide (0.12 g); MS: m/z=366(M-84); NMR: 3.00 (s,3), 3.345 (s,3), 4.4 (m,1), 6.65 (s,1), 7.12 (m,2), 7.33 (m,1), 7.34–7.55 (m,4).

d. (1R*,3'R*)-3'-(3,4-Dichlorophenyl)-2-methyl-2,3-dihydro-1H-isoindole-1-spiro-2'-(tetrahydrofuran)-3-one. A solution of 2-[2-(3,4-dichlorophenyl)-4-tetrahydropyran-2-yloxy)butyryl]-N-methylbenzamide (0.913 g) in methanol (50 mL) was treated with a strong acid ion exchange resin (0.25 g), and the resulting suspension was heated to 60° C. for 16 hours. The reaction mixture was cooled to room temperature, filtered through diatomaceous earth, and evaporated. Chromatography, eluting with hexane:ethyl acetate (2:1) afforded two products. The faster moving component (0.199 g) and the slower moving component (0.215 g) were studied by NMR by using proton-proton coupling experiments and assigned structures. The slower moving isomer (1R*,3'R*)-3'-(3,4-dichlorophenyl)-2-methyl-2,3-dihydro-1H-isoindole-1-spiro-2'-(tetrahydrofuran)-3-one was used in the next step without further characterization.

e. 3-[1-(3,4-Dichlorophenyl)-3-hydroxypropyl]-2-methyl-2,3-dihydroisoindol-1-one. A solution of (1R*,3'R*) 3'-(3,4-dichloro-phenyl)-2-methyl-2,3-dihydro-1H-isoindole-1-spiro-2'-(tetrahydro-furan)-3-one (0.619 g) in methanol (50 mL) was treated with 10% palladium on carbon (0.1 g) and hydrogenated at atmospheric pressure for 3 hours. The reaction mixture was filtered through diatomaceous earth and evaporated. Chromatography, eluting with ethyl acetate, gave the alcohol (0.192 g); MS: m/z=350(M+1); NMR (CDCl$_3$): 2.23 (m,2), 3.31 (s,3), 3.5 (m,1), 3.63 (m,2), 4.65 (d,1, J=4), 6.50–7.79 (m,7).

f. 3-(3,4-Dichlorophenyl)-3-(2-methyl-3-oxo-2,3-dihydro-1H-isoindol-1-yl)propionaldehyde. A solution of oxalyl chloride (0.095 g) in dichloromethane (10 mL) was cooled to −78° C. and treated with dimethyl sulfoxide (0.117 g). After the reaction mixture was stirred at −78° C. for 2 minutes, a solution of 3-[1-(3,4-dichlorophenyl)-3-hydroxypropyl]-2-methyl-2,3-dihydroisoindol-1-one (0.175 g) in dichloromethane (2 mL) was added; and the stirring was continued for 30 minutes. Diisopropylethylamine (0.388 g) was added and the reaction mixture was allowed to warm to the room temperature. Upon stirring for 2 hours at the room temperature, the reaction mixture was diluted with water and extracted with dichloromethane. The organic layer was passed through activated magnesium silicate (Florisil) and evaporated to afford the aldehyde as an oil (0.112 g); MS: m/z=348(M+1).

The intermediate 1-bromo-2-(tetrahydropyran-2-yloxy) ethane was prepared as follows.

g. A mixture of freshly distilled 2-bromoethanol (94.04 g) in hexane (200 mL) was cooled in ice and treated slowly with dihydropyran (75.85 g). After the addition of dihydropyran was completed, the reaction mixture was allowed to warm to the room temperature while stirring over a period of 30 minutes and then stirred for additional 1 hour. The reaction mixture was concentrated by distilling off the hexane at the atmospheric pressure and the residual liquid was distilled under reduced pressure to obtain a liquid (122 g); bp 55–85° C./13.3 Pa.; MS: m/z=209(M+1); NMR (CDCl$_3$): 1.65 (m,6), 3.5 (m,4), 3.72–4.66 (m,4), 4.68 (t,1, J=8).

EXAMPLE 2

(3R*)-3-[(1R*)-1-(3,4-Dichlorophenyl)-3-(4-hydroxy-4-phenylpiperidino)propyl]-2-methyl-2,3-dihydroisoindol-1-one hydrochloride (3R*)-3-(3,4-Dichlorophenyl)-3-((1R*)-2-methyl-3-oxo-2,3-dihydro-1H-isoindol-1-yl)propionaldehyde (0.265 g) was coupled to 4-hydroxy-4-phenylpiperidine (0.135 g) using a procedure similar to that described in Example 1. After aqueous work up, the product was purified by chromatography. Eluting with dichloromethane:methanol (20:1) afforded the free amine (0.186 g) which was transformed to the corresponding hydrochloride salt as described in Example 1 to afford the title compound (0.16 g); MS: m/z=509(M+1); NMR: 1.78 (broad,2), 2.09 (broad,2), 3.25 (s,3), 3.77 (broad,1), 4.90 (m,1), 5.43 (s,1), 7.14–7.57 (m,12). Analysis for $C_{29}H_{30}Cl_2N_2O_2 \cdot HCl \cdot H_2O$: Calculated: C, 61.76; H, 5.89; N, 4.96; Found: C, 62.18; H, 5.71; N, 4.91.

The intermediate (3R*)-3-(3,4-dichlorophenyl)-3-[(1R*)-2-methyl-3-oxo-2,3-dihydro-1H-isoindol-1-yl]propionaldehyde was synthesized as follows:

a. 2-(3,4-Dichlorophenyl)pent-4-enoic acid ethyl ester. To a suspension of sodium hydride (4.0 g of 60% dispersion in oil) in tetrahydrofuran (25 mL) at 0° C. was added a solution of the ethyl 3,4-dichlorophenylacetate (23.3 g) and the suspension was stirred at room temperature for 2 hours. The reaction mixture was cooled to −15° C. and treated with allyl bromide (12.1 g). Upon stirring at ambient temperature for 16 hours, the reaction mixture was quenched with saturated ammonium chloride solution and diluted with ether. The aqueous layer was extracted with ether and the combined organic layers were washed with brine. Drying and evaporation of the organic layer gave the alkene (20.2 g); MS: m/z=273(M+1); NMR (CDCl$_3$): 1.19 (t,3, J=7), 2.7 (m,2), 3.57 (m,1), 4.11 (m,2), 5.0 (m,2), 5.7 (m,1), 7.15–7.42 (m,2).

b. 2-[2-(3,4-Dichlorophenyl)pent-4-enoyl]-N-methylbenzamide. A solution of N-methylbenzamide (6.75 g) in tetrahydrofuran (300 mL) was cooled to −15° C. and treated with tert-butyl lithium (59 mL of 1.7 M solution). The resulting bright red solution was stirred for 1 hour at −15° C., cooled to −78° C. and treated slowly with a solution of 2-(3,4-dichlorophenyl)pent-4-enoic acid ethyl ester (13.65 g) in tetrahydrofuran (50 mL). Upon warming to the room temperature and stirring for 1 hour, the reaction mixture was quenched with saturated ammonium chloride solution, diluted with ether, and the aqueous layer was extracted with ether. The organic layers were washed with saturated sodium chloride solution, dried and evaporated. Chromatography, eluting with hexane:ethyl acetate (1:1), afforded the amide (1.3 g); MS: m/z=362(M+1); NMR (CDCl$_3$): 1.88 (broad,1), 2.08 (broad,1), 2.94 (s,3), 3.39 (m,1), 4.85 (m,2), 5.43 (m,1), 6.84–7.6 (m,7).

c. (3R*)-3-[(1R*)-1-(3,4-Dichlorophenyl)but-3-enyl]-2-methyl-2,3-dihydroisoindol-1-one. A solution of 2-[2-(3,4-dichlorophenyl)-pent-4-enoyl]-N-methylbenzamide (3.91 g) in trifluoroacetic acid (100 mL) was stirred at the room temperature until it completely dissolved and then treated with triethylsilane (50 mL). This reaction mixture was refluxed for 16 hours and then cooled to the room temperature. After evaporation, the residue was treated successively with 100 mL of toluene and methanol and the low boiling material was distilled off under reduced pressure. The remaining residue was dissolved in ethyl acetate and treated with sodium bicarbonate solution. The aqueous layer was extracted with ethyl acetate; and the combined organic layers were washed (sodium bicarbonate solution, 1N sodium hydroxide solution, sodium bicarbonate solution, brine), dried and evaporated. Chromatography, eluting with hexane:isopropanol (9:1) afforded two compounds. The faster moving component was the (R*,R*)-isomer of the subsituted isoindolone (0.33 g); MS: m/z=346(M+1); NMR (CDCl$_3$): 2.1 (m,2), 3.26 (s,3), 4.63 (d,1, J=3.5), 4.95 (m,2), 5.56 (m,1), 6.77 (m,1), 7.07 (m,1), 7.32–7.46 (m,4), 7.81 (m,1).

d. (3R*)-3-(3,4-Dichlorophenyl)-3-((1R*)-2-methyl-3-oxo-2,3-dihydro-1H-isoindol-1-yl)propionaldehyde. A solution of (3R*)-3-[(1R*)-1-(3,4-dichlorophenyl)but-3-enyl]-2-methyl-2,3-dihydroiso-indol-1-one (0.27 g) in tetrahydrofuran (9 mL) was treated with osmium tetroxide solution (0.3 mL of 0.128M in water) followed by a solution of sodium periodate (0.314 g in 5 mL of water) in 1 mL portions over a period of 20 minutes. At the end of the final addition the reaction mixture was stirred for additional 10 minutes, diluted with water and extracted with ethyl acetate. The organic layer was washed with brine, dried and evaporated to afford the aldehyde (0.268 g); MS: m/z=348 (M+1). This material was used in the step described above without further purification.

EXAMPLE 3

(3R*)-3-[(1S*)-1-(3,4-Dichlorophenyl)-3-(4-hydroxy-4-phenylpiperidino)propyl]-2-methyl-2,3-dihydroisoindol-1-one hydrochloride The aldehyde (3R*)-3-(3,4-dichlorophenyl)-3-((1S*)-2-methyl-3-oxo-2,3-dihydro-1H-isoindol-1-yl) propionaldehyde (0.304 g) was coupled to 4-hydroxy-4-phenylpiperidine (0.156 g) as described in Example 1. After aqueous work up, the product was purified by chromatography. Eluting with dichloromethane:methanol (20:1) afforded (3R*)-3-[(1S*)-1-(3,4-dichlorophenyl)-3-(4-hydroxy-4-phenylpiperidin-1-yl)propyl]-2-methyl-2,3-dihydroisoindol-1-one (0.31 g) which was transformed to the hydrochloride salt using a procedure similar to that described in Example 1 (0.3 g); MS: m/z=509(M+1); NMR: 1.82 (broad,2), 2.9 (m,1), 3.08 (s,3), 3.51 (broad,2), 3.7 (broad,1), 4.90 (m,1), 5.47 (s,1), 6.79–7.96 (m,12). Analysis for $C_{29}H_{30}Cl_2N_2O_2$·HCl·0.5 $H_2O$: Calculated: C, 62.77; H, 5.81; N, 5.04; Found: C, 62.57; H, 5.58; N, 4.80.

The intermediate (3R*)-3-(3,4-dichlorophenyl)-3-((1S*)-2-methyl-3-oxo-2,3-dihydro-1H-isoindol-1-yl) propionaldehyde was synthesized as follows:

a. (3R*)-3-[(1S*)-1-(3,4-Dichlorophenyl)but-3-enyl]-2-methyl-2,3-dihydroisoindol-1-one. The slower moving isomer described in Example 2.c. was isolated from the chromatographic separation to give (3R*)-3-[(1S*)-1-(3,4-dichlorophenyl)but-3-enyl]-2-methyl-2,3-dihydroisoindol-1-one (0.549 g); MS: m/z=346(M+1); NMR (CDl$_3$): 2.73 (m,2), 3.11 (s,3), 3.43 (m,1), 4.67 (d,1, J=4), 5.1 (m,2), 5.75 (m,1), 6.55 (dd,1, J=2, 8), 6.80 (d,1, J=2), 7.10–7.73 (m,5).

b. (3R*)-3-(3,4-Dichlorophenyl)-3-((1S*)-2-methyl-3-oxo-2,3-dihydro-1H-isoindol-1-yl)propionaldehyde. Treatment of (3R*)-3-[(1S*)-1-(3,4-dichlorophenyl) but-3-eneyl]-2-methyl-2,3-dihydroisoindol-1-one (0.5 g) with osmium tetroxide (0.55 mL of 0.128 M in water) and sodium periodate (0.65 g) using a procedure similar to that of Example 2.d. afforded crude material which was purified by chromatography, with ethyl acetate as the eluent, to give the (R*,S*)-aldehyde (0.304 g); MS: m/z=348(M+1).

EXAMPLE 4

(−)-(3R/3S)-3-[(1S/1R)-1-(3,4-dichlorophenyl)-3-(4-hydroxy-4-phenylpiperidino)propyl]-2-methyl-2,3-dihydroisoindol-1-one hydrochloride Racemic (3R*)-3-[(1S*)-1-(3,4-dichlorophenyl)-3-(4-hydroxy-4-phenylpiperidino)propyl]-2-methyl-2,3-dihydro-isoindol-1-one (1.2 g) was suspended in dichloromethane (200 mL) and treated with 1N NaOH (3 mL). After stirring, the pH was 9.0, at which time anhydrous sodium sulfate (35 g) was added. Upon filtering and evaporation the free base (1.04 g) was obtained. This material was chromatographed with a cellulose OD column using hexane:ethanol:acetonitrile (60:40:2). The faster moving peak was isolated to afford an oil which was converted to the hydrochloride salt by a procedure similar to the one described in Example 1 to give the title compound as a white solid (0.35 g), mp 185° C. (dec); [ ]$_D$=−20° (c=1.0, MeOH); MS: m/z=509(M+1); NMR: 1.95 (d,2, J=14), 2.71 (broad,2), 3.0 (broad,3), 3.13 (s,3), 3.64 (broad,1), 4.71 (s,1), 6.66 (d,1, J=7), 6.83 (s,1), 7.17–7.75 (m,10). Analysis for $C_{29}H_{30}Cl_2N_2O_2 \cdot HCl \cdot 0.66 H_2O$: Calculated: C, 62.44; H, 5.84; N, 5.02; Found: C, 62.21; H, 5.72; N, 4.97.

EXAMPLE 5

(+)-(3R/3S)-3-[(1S/1R)-1-(3,4-Dichlorophenyl)-3-(4-hydroxy-4-phenylpiperidino)propyl]-2-methyl-2,3-dihydroisoindol-1-one hydrochloride The slower moving peak in the chromatographic separation of (3R*)-3-[(1S*)-1-(3,4-dichlorophenyl)-3-(4-hydroxy-4-phenylpiperidino)propyl]-2-methyl-2,3-dihydroisoindol-1-one was isolated to afford the (+)-isomer as an oil. This material was transformed to the corresponding hydrochloride salt by a procedure similar to the one described in Example 1 to give the title compound (0.345 g); mp 185° C. (dec); [ ]$_D$=+22° (c=1.0, MeOH); MS: m/z=509(M+1); NMR (CDCl$_3$): 1.93 (d,2, J=12), 2.69 (broad,2), 3.10 (broad,3), 3.63 (broad,1), 4.69 (s,1), 6.65 (broad,1), 6.83 (s,1), 7.15–7.71 (m,10). Analysis for $C_{29}H_{30}Cl_2N_2O_2 \cdot HCl \cdot 0.66 H_2O$: Calculated: C, 62.44; H, 5.84; N, 5.02; Found: C, 62.49; H, 5.85; N, 4.91.

EXAMPLE 6

3-[1-(3,4-Dichlorophenyl)-3-(4-hydroxy-4-phenyl-piperidino)propyl]-2-methyl-2H-isoquinolin-1-one 3-[1-(3,4-Dichlorophenyl)-3-oxopropyl]-2-methyl-2H-isoquinolin-1-one (0.303 g) was coupled to 4-hydroxy-4-phenyl-piperidine (0.15 g) by method similar to that described in Example 1. After aqueous work up, the product was purified by column chromatography. Eluting with ethyl acetate, followed by dichloromethane:methanol, (9:1) afforded the title compound as a solid; mp 100–102° C.; MS: m/z=521(M+1); NMR: 1.55 (t,2, J=12), 1.89 (m,2), 2.10 (m,1), 2.28 (m,5), 3.35 (s,3), 4.46 (broad,1), 6.90 (s,1), 7.17–7.71 (m,11), 8.18 (d,1, J=8). Analysis for $C_{30}H_{30}Cl_2N_2O_2 \cdot 0.5 H_2O$: Calculated: C, 67.92; H, 5.89; N, 5.28; Found: C, 68.22; H, 5.86; N, 5.16.

The intermediate 3-[1-(3,4-dichlorophenyl)-3-oxopropyl]-2-methyl-2H-isoquinolin-1-one was synthesized as follows:

a. 2-[3-(3,4-Dichlorophenyl)-2-oxo-5-(tetrahydropyran-2-yloxy)pentyl]-N-methylbenzamide. A solution of N-methyl-o-toluamide (1.49 g) in tetrahydrofuran (50 mL) at −15° C. was treated with tert-butyl lithium (14 mL of 1.7 M solution). The reaction mixture was stirred for 1 hour and the resulting bright red solution was cooled to −78° C. A solution of 2-(3,4-dichlorophenyl)-4-(tetrahydropyran-2-yloxy)butyric acid ethyl ester (3.61 g) in tetrahydrofuran (10 mL) was added to the reaction mixture, and the resulting colorless solution was allowed to warm to the room temperature over a period of 1 hour. The reaction was quenched with saturated ammonium chloride solution and then diluted with ether. The aqueous layer was extracted with ether and the organic layers were washed with brine, dried and evaporated to afford the ketone (5.2 g) which was used in the next step without further purification.

b. 3-[1-(3,4-Dichlorophenyl)-3-hydroxypropyl]-2-methyl-2H-isoquinolin-1-one. A solution of 2-[3-(3,4-dichlorophenyl)-2-oxo-5-(tetrahydropyran-2-yloxy)pentyl]-N-methylbenzamide in 200 mL of methanol was treated with a strong acid ion exchange resin (0.5 g) and heated to reflux for 16 hours. The reaction mixture was allowed to cool to room temperature, filtered through diatomaceous earth and evaporated to afford the crude product. Chromatography, eluting with hexane:ethyl acetate (1:1), afforded the alcohol (1.65 g); MS: m/z=361(M+1); NMR (CDCl$_3$): 2.08 (m,1), 2.37 (m,1), 3.47 (s,3), 3.77 (m,1), 3.80 (m,1), 4.39 (m,1), 6.58 (s,1), 7.11 (dd,1, J=2, 8), 7.33–7.69 (m,5), 8.41 (dd$_1$, J=1, 8).

c. 3-[1-(3,4-Dichlorophenyl)-3-oxopropyl]-2-methyl-2H-isoquinolin-1-one. 3-[1-(3,4-Dichlorophenyl)-3-hydroxypropyl]-2-methyl-2H-isoquinolin-1-one (0.36 g) was oxidized using a method similar to the one described in Example 1.f. to give the aldehyde (0.33 g) as an oil; MS: m/z=360(M+1). This material was used in the reaction described above without further purification.

EXAMPLE 7

3-[1-(3,4-Dichlorophenyl)-3-(4-hydroxy-4-phenylpiperidino)propyl]-2,3-dihydroisoindol-1-one hydrochloride 3-(3,4-dichlorophenyl)-3-(3-oxo-2,3-dihydro-1H-isoindol-1-yl)propionaldehyde (0.75 g) was coupled to 4-hydroxy-4-phenyl-piperidine (0.34 g) as described in Example 1. After chromatography, using dichloromethane:methanol (20:1) as eluent, the free amine was converted to the hydrochloride salt, to give the title compound as a white solid (0.4 g); mp 190° C.(dec); MS: m/z=495(M+1); NMR (CDCl$_3$): 2.02 (broad,4), 2.70 (broad, 4), 4.92 (broad,1), 6.95–7.73 (m,12). Analysis for $C_{28}H_{28}Cl_2N_2O_2 \cdot HCl \cdot 0.5 H_2O$: Calculated: C, 62.17; H, 5.59; N, 5.18; Found: C, 62.01; H, 5.54; N, 4.98.

The intermediate 3-(3,4-dichlorophenyl)-3-(3-oxo-2,3-dihydro-1H-isoindol-1-yl)-propionaldehyde was prepared as follows:

a. N-tert-Butylbenzamide. A solution of benzoyl chloride (14.0 g) in dichloromethane (100 mL) at 0° C. was slowly treated with tert-butylamine (14.6 g). After the addition was completed, the reaction mixture was warmed to the room temperature over a period of 1 hour and diluted with dichloromethane. Washing with sodium bicarbonate solution, drying and evaporation of the organic layer afforded the amide, which was crystallized from hot ethyl acetate (50 mL) to obtain a solid (11.7 g); MS: m/z=178(M+1); NMR (CDCl$_3$): 1.48 (s,9), 5.94 (broad,1), 7.44 (m,3), 7.73 (m,2).

b. 2-[2-(3,4-Dichlorophenyl)pent-4-enoyl]-N-tert-butyl-benzamide. A solution of N-tert-butylbenzamide (5.31 g) in tetrahydrofuran (200 mL) at −78° C. was treated with tert-butyl lithium (35.3 mL of 1.7 M solution) and the resulting orange solution was stirred for 15 minutes at −78° C., warmed to 0° C. and stirred for 30 minutes, and finally warmed to the room temperature. The resulting yellow solution was transferred through a cannula to a solution of 2-(3,4-dichlorophenyl)pent-4-enoic acid ethyl ester (8.19 g) in tetrahydrofuran (100 mL) at −78° C. The resulting reaction mixture was transferred back to the vessel in which the lithiation was carried out, warmed to the room temperature and quenched with saturated ammonium chloride solution. The reaction mixture was then diluted with ether and the aqueous layer was extracted with additional ether. The combined organic layers were washed with brine, dried and evaporated to afford a semi solid; MS: m/z=404 (M+1). This material was used in the next step without further purification.

c. 3-[1-(3,4-Dichlorophenyl)but-3-enylidine]-2,3-dihydro-isoindol-1-one. A solution of 2-[2-(3,4-dichlorophenyl)pent-4-enoyl]-N-tert-butylbenzamide (5.12 g) in trifluoroacetic acid (50 mL) was refluxed for 16 hours and then evaporated. The residue was suspended in sodium bicarbonate solution and extracted with ethyl acetate. The combined organic layers were dried and evaporated to afford the crude product. Chromatography, eluting with hexane:ethyl acetate (4:1, 1:1) two fractions containing a mixture of E- and Z-isomers of the alkene. The material was used in the next step without further purification.

d. 3-[1-(3,4-Dichlorophenyl)but-3-enyl]-2,3-dihydroisoindol-1-one. A solution of the mixture of (E)- and (Z)-3-[1-(3,4-dichlorophenyl)but-3-eneylidine]-2,3-dihydroisoindol-1-one (1.69 g, described in Example 7.c.) in trifluoroacetic acid (30 mL) was treated with triethylsilane (15 mL) and heated to reflux for 20 hours. At the end of this period the reaction mixture was evaporated, and the residue was dissolved in ethyl acetate. The organic layer was washed with sodium bicarbonate, dried, and evaporated. Chromatography, eluting with hexane:ethyl acetate (1:1), afforded 3-[1-(3,4-dichlorophenyl)-but-3-eneyl]-2,3-dihydroisoindol-1-one (0.64 g); MS: m/z=332(M+1); NMR (CDCl$_3$): 2.4–2.8 (m,2), 3.1–3.3 (m,1), 4.9 (m,2), 5.1 (m,1), 5.6 (m,1), 6.9–8.05 (m,8).

e. 3-(3,4-Dichlorophenyl)-3-(3-oxo-2,3-dihydro-1H-isoindol-1-yl)propionaldehyde. 3-[1-(3,4-dichlorophenyl)but-3-eneyl]-2,-dihydroisoindol-1-one (0.64 g) was oxidized to the corresponding aldehyde using a method similar to that described in Example 2.d. to give a brown oil (0.75 g); MS: m/z=334(M+1). This aldehyde was used in the next step described above without further purification.

EXAMPLE 8

(3R)-3-[(1S)-1-(3,4-Dichlorophenyl)-3-(4-(2-methylsulfinylphenyl)-piperidino)propyl]-2-methyl-2,3-dihydroisoindol-1-one hydrochloride A solution of (3S)-3-(3,4-dichlorophenyl)-3-[(1R)-2-methyl-3-oxo-2,3-dihydro-1H-isoindol-1-yl] propionaldehyde (0.54 g) in methanol (10 mL) was treated with 4-(2-methylsulfinylphenyl)piperidine (0.61 g) and the pH was adjusted to 3 with acetic acid and triethylamine. After treating with sodium cyanoborohydride (189 g) the reaction mixture was stirred at ambient temperature for 16 hours, acidified with 10% hydrochloric acid, stirred for 15 minutes and then diluted with a saturated solution of sodium bicarbonate. Upon extraction with dichloromethane, the organic layer was dried and evaporated to obtain the crude product. This material was purified by chromatography, with 20:1 dichloromethane:methanol as the eluent to give the desired 3-[1-(3,4-dichlorophenyl)-3-(4-(2-methylsulfinylphenyl)piperidino)propyl]-2-methyl-2,3-dihydroisoindol-l-one (0.414 g). This material was transformed into the hydrochloride salt as follows. The material was dissolved in dichloromethane (2 mL) and treated with hydrochloric acid in ether (2 mL). The resulting solution was diluted with anhydrous ether (80 mL), stirred for 4 hours, and the resulting precipitate was collected to afford the title compound (0.35 g); mp 180–188° C.; MS: m/z=555(M+1); NMR(CD$_3$SOCD$_3$): 2.0 (broad,2), 2.3 (broad,2), 2.7 (s,3), 3.1 (s,3), 3.6 (t,2, J=15), 3.76 (m,1), 4.9 (d,1, J=2.4), 6.8 (d,1, J=7.8), 7.0 (s,1), 7.3–7.98 (m,9). Analysis for C$_{30}$H$_{32}$C.HClH$_2$O: Calculated: C, 59.07; H, 5.78; N, 4.59; Found: C, 59.06; H, 5.72; N, 4.45.

The intermediate (3S)-3-(3,4-dichlorophenyl)-3-[(1R)-2-methyl-3-oxo-2,3-dihydro-1H-isoindol-1-yl] propionaldehyde was prepared as described in Example 57 sub-parts a.–c.

The intermediate 4-(2-methylsulfinylphenyl)piperidine was prepared as described in Example 66 sub-parts d.–h.

EXAMPLE 9

3-[1-(3,4-Dichlorophenyl)-3-(4-(2-hydroxyethyl)-piperidino)propyl]-2-methyl-2,3-dihydroisoindol-1-one hydrochloride 3-(3,4-dichlorophenyl)-3-(2-methyl-3-oxo-2,3-dihydro-1H-isoindol-1-yl)propionaldehyde (0.387g) was coupled to 4-(2-hydroxy-ethyl)piperidine (0.13g) by a method similar to that described in Example 8. The reaction product was not purified by chromatography but converted to the corresponding hydrochloride salt as described in the Example 8 to afford the title compound (0.178 g); mp 119–125° C. (d); MS: m/z=461(M+1); NMR(CDCl$_3$): 2.5–2.4(m,15), 3.1 (s,3), 3.56 (broad,2), 3.7 (broad,2), 4.7 (s,1), 6.6 (d,1, J=7.5), 6.8 (s,1), 7.13 (d,1, J=8), 7.4–7.7 (m,4). Analysis for C$_{25}$H$_{30}$Cl$_2$N$_2$O$_2$.HCl: Calculated: C, 56.19; H, 6.03; N, 5.24; Found: C, 56.01; H, 5.77; N, 5.06.

EXAMPLE 10

3-[1-(3,4-Dichlorophenyl)-3-(4-(3-methoxyphenyl) piperidino)propyl]-2-methyl-2,3-dihydroisoindol-1-one hydrochloride 3-(3,4-Dichlorophenyl)-3-(2-methyl-3-oxo-2,3-dihydro-1H-isoindol-1-yl)propionaldehyde (0.52 g) was coupled to 4-(3-methoxyphenyl)piperidine (0.41 g) by a method similar to that described in Example 8. The reaction product was purified by chromatography and converted to the corresponding hydrochloride salt as described in Example 8 to afford the title compound (0.16 g); mp 210–220° C.; MS: m/z=523(M+1); NMR(CD$_3$SOCD$_3$): 1.98–2.1 (m,4), 2.79 (m,2), 3.06 (s,3), 3.7 (s,3), 4.87 (d,1, J=3.2), 6.8 (m,4), 6.98 (s,1), 7.23–7.35 (m,2), 7.5 (s,2), 7.65 (m,1), 7.95 (d,1, J=7.5). Analysis for C$_{30}$H$_{32}$Cl$_2$N$_2$O$_2$.1.5 HCl: Calculated: C, 62.32; H, 5.84; N, 4.85; Found: C, 62.51; H, 5.77; N, 4.76.

The intermediate 4-(3-methoxyphenyl)piperidine was prepared as follows:

a. 1-Benzyloxycarbonyl-4-hydroxy-4-(3-methoxyphenyl) piperidine. Using a method similar to that described in Example 13 sub-part b., except that the reaction was not warmed above −78° C. and 3-bromoanisole was used instead of anisole, the alcohol was prepared. The product was contaminated with the starting piperidone (2:1 as indicated by NMR); NMR (CDCl$_3$): 1.72–1.77 (broad,2), 2.04 (broad,2), 3.25 (broad,2), 3.8 (s,3), 4.0–4.25 (broad,2), 5.1 (s,2), 6.83 (m,2), 7.02–7.4 (m,2), 7.26–7.39 (m,6); MS: m/z=324(M+18). This material was used in the next step without further purification.

b. 1-Benzyloxycarbonyl-4-(3-methoxyphenyl)piperidine. 1-Benzyloxycarbonyl-4-hydroxy-4-(3- methoxyphenyl)piperidine (1.79 g) was subjected to a procedure similar to that described in Example 13 sub-part c. The crude product was chromatographed, with hexane:ethyl acetate (2:1) as the eluent, to give the des-hydroxy compound (1.29 g); MS: m/z=326(M+1); NMR of this material was complex. This material was used in the next step without any further purification.

c. 4-(3-Methoxyphenyl)piperidine. A solution of 1-Benzyloxycarbonyl-4-(3-methoxyphenyl)piperidine (0.42 g) in ethanol (5 mL) was treated with 10% palladium on carbon (0.04 g) and hydrogenated for 16 hours at atmospheric pressure. The reaction mixture was filtered through diatomaceous earth and evaporated to afford 4-(3-methoxyphenyl)piperidine as a pale yellow oil (0.19 g); NMR (CDCl$_3$): 1.64–1.77 (m,2), 1.85 (broad,2), 2.74 (m,2), 3.21–3.25 (broad,2), 3.80 (s,3), 6.73–6.83 (m,3), 7.21–7.26 (t,1, J=8); MS: m/z= 192(M+1). This material was used in the next step without further purification.

EXAMPLE 11

3-[1-(3,4-Dichlorophenyl)-3-(4-acetamido-4-phenyl-piperidino)propyl]-2-methyl-2,3-dihydroisoindol-1-one hydrochloride 3-(3,4-Dichlorophenyl)-3-(2-methyl-3-oxo-2,3-dihydro-1H-isoindol-1-yl)propionaldehyde (0.375 g) was coupled to 4-acetamido-4-phenylpiperidine (0.28 g) by a method similar to that described in Example 8. The reaction product was purified by chromatography and converted to the corresponding hydrochloride salt as described in Example 8 to afford the title compound (0.263 g); mp 185–192° C.; MS: m/z=550(M+1); NMR(CD$_3$SOCD$_3$): 1.91 (s,3), 2.3 (m,2), 3.06 (s,3), 3.15 (m,2), 4.87 (d,1, J=3.5), 6.8 (d,1, J=8), 7.0 (d,1, J=1.8), 7.23 (m,1), 7.34 (m,5), 7.48 (m,2), 7.65 (m,1), 7.90 (d,1, J=7.6), 8.1 (s,1). Analysis for C$_{31}$H$_{33}$Cl$_2$N$_3$O.1.5 HCl: Calculated: C, 60.64; H, 6.07; N, 6.84; Found: C, 60.98; H, 5.91; N, 6.75.

EXAMPLE 12

3-[1-(3,4-Dichlorophenyl)-3-(4-(4-hydroxyphenyl)-piperidino)propyl]-2-methyl-2,3-dihydroisoindol-1-one hydrochloride 3-(3,4-Dichlorophenyl)-3-(2-methyl-3-oxo-2,3-dihydro-1H-isoindol-1-yl)propionaldehyde (0.378 g) was coupled to 4-(4-hydroxy-phenyl)piperidine (0.191 g) by a method similar to that described in Example 8. The reaction product was not purified by chromatography but converted to the corresponding hydrochloride salt as described in Example 8 to afford the title compound (0.414 g); mp 150–160° C.; MS: m/z=508(M+1); NMR(CD$_3$SOCD$_3$): 1.93–2.06 (m,4), 2.65–2.73 (m,3), 3.06 (s,3), 3.35 (m,4), 3.6–3.7 (m,3), 4.87 (d,1, J=3.5), 6.7–6.8 (m,3), 6.9–7.0 (m,3), 7.32 (d,1, J=8.3), 7.50 (s,2), 7.64 (m,1), 7.95 (d,1, J=7.7). Analysis for C$_{29}$H$_{30}$Cl$_2$N$_2$O$_2$.1.0 HCl1.0 H$_2$O: Calculated: C, 61.87; H, 5.73; Found: C, 62.13; H, 5.94.

The intermediate 4-(4-hydroxyphenyl)piperidine was prepared as follows:

a. 4-Benzyloxybromobenzene. A solution of 4-bromophenol (17.3 g) in dimethylformamide (200 mL) was treated with potassium carbonate (15.2 g) followed by benzyl bromide (17.1 g 11.9 mL). After stirring for 16 hours at ambient temperature, the reaction mixture was diluted with water and hexane. The aqueous layer was extracted with hexane:ether (5:1). The organic extracts were washed (water, 1 N sodium hydroxide, brine), dried and evaporated to give the bromobenzene as a white solid (23.4 g); NMR (CDCl$_3$): 5.03 (s,2), 6.85 (dd,2, J$_1$=5, J$_2$=2), 7.3–7.4 (m,7); MS: m/z=263(M+1). This material was used in the next step without further purification.

b. 1-Benzyloxycarbonyl-4-hydroxy-4-(4-benzyloxyphenyl)-piperidine. A solution of 4-benzyloxybromobenzene (6.6 g) in tetrahydrofuran (125 mL) was cooled to –78° C. and treated with n-butyl lithium (10 mL of a 2.5M solution in hexane). After stirring for 20 minutes at –78° C., a solution of 1-benzyloxycarbonyl-4-piperidone (5.85 g) in tetrahydrofuran (5 mL) was added; and the reaction mixture was stirred at –78° C. for 1 hour followed by 2 hours at 0° C. The resulting solution was treated with water (10 mL) and extracted with ethyl acetate. The organic layer was washed with brine, dried and evaporated to afford a crude product which was chromatographed, with hexane:isopropanol (9:1) as the eluent, to give two fractions (1.91 and 4.05 g each). The first fraction was a 1:1 mixture of the alcohol and the starting ketone as indicated by NMR, while the second fraction was the alcohol (39% yield); NMR (CDCl$_3$): 1.74 (d,2, J=13), 2.04 (broad,1), 3.32 (m,2), 4.09 (broad,2), 5.05 (s,2), 5.14 (s,2), 6.96 (m,2), 7.29–7.49 (m,12); MS: m/z=450 (M+18).

c. 1-Benzyloxycarbonyl-4-(4-benzyloxyphenyl) piperidine. 1-Benzyloxycarbonyl-4-hydroxy-4-(4-benzyloxyphenyl)piperidine was subjected to a procedure similar to that described in Example 13 sub-part c. The resulting product was chromatographed, with hexane:ethyl acetate (2:1) as the eluent, to give the des-hydroxy compound contaminated with the corresponding alkene (3.48 g); MS: m/z=402(M+1); NMR of this material was complex. This material was used in the next step without any further purification.

d. 4-(4-Hydroxyphenyl)piperidine. 1-Benzyloxycarbonyl-4-(4-benzyloxyphenyl) piperidine (0.65 g) was subjected to a procedure similar to that described in Example 10 sub-part c. to give 4-(4-hydroxyphenyl)piperidine as a brown solid (0.28 g); NMR (CDCl$_3$): 1.3–1.5 (m,2), 1.6 (broad,2), 2.9–3.0 (broad,2), 6.66 (d, J=8 ), 6.99 (d,2, J=8); MS: m/z=178(M+1). This material was used in the next step without further purification.

EXAMPLE 13

3-[1-(3,4-Dichlorophenyl)-3-(4-(2-methoxyphenyl) piperidino)propyl]-2-methyl-2,3-dihydroisoindol-1-one hydrochloride 3-(3,4-Dichlorophenyl)-3-(2-methyl-3-oxo-2,3-dihydro-1H-isoindol-1-yl)propionaldehyde (0.368 g) was coupled to 4-(2-methoxyphenyl)piperidine (0.203 g) by a method similar to that described in Example 8. The reaction product was not purified by chromatography but converted to the corresponding hydrochloride salt as described in Example 8 to afford the desired title compound (0.469 g); mp 175–182° C.; MS: m/z=523(M+1); NMR(CD$_3$SOCD$_3$): 1.83–1.90 (m,3), 2.05–2.13 (m,2), 2.80 m(1), 3.07 (s,3), 3.57 (m,2), 3.8 (s,3), 4.89 (d,1, J=3.7), 6.7 (dd,1, J=8.4, 2), 7.0 (m,3), 7.12–7.6 (m,6), 7.94 (d,1, J=7.5). Analysis for C$_{30}$H$_{32}$Cl$_2$N$_2$O$_2$.1.0 HCl.1.5 H$_2$O; Calculated: C, 61.39; H, 6.18, N, 4.77; Found: C, 61.33; H, 6.12; N, 4.99.

The intermediate 4-(2-methoxyphenyl)piperidine was prepared as follows:

a. 1-Benzyloxycarbonyl-4-piperidone. A suspension of 4-piperidone hydrochloride (11.96 g) in tetrahydrofuran (150 mL) was cooled to 0° C. and treated with benzyl chloroformate (14.3 mL). The reaction mixture was treated, dropwise, with 67 mL of an aqueous solution of sodium hydroxide (7.84 g in 76 mL of water) and allowed to stir for 2 hours. The reaction mixture was extracted with ethyl acetate, the organic layer was washed with water, dried and evaporated to afford the piperidone as a pale yellow oil (20.58 g); NMR (CDCl$_3$): 2.45 (t,4, J=6), 3.79 (t,4, J=6), 5.18 (s,2), 7.32–7.38 (m,5); MS: m/z=234(M+1). This material was used in the next step without further purification.

b. 1-Benzyloxycarbonyl-4-hydroxy-4-(2-methoxyphenyl) piperidine. A solution of anisole (2.19 g) in tetrahydrofuran (50 mL) was cooled to –78° C. and treated with tert-butyl lithium (12 mL of a 1.7 M solution in pentane). The resulting reaction mixture was warmed to –15° C. and stirred for 45 minutes. The reaction mixture was cooled back to –78° C. and treated with a solution of 1-benzyloxycarbonyl-4-piperidone (4.67 g) in tetrahydrofuran (5 mL). The reaction mixture was warmed to –15° C. and stirred for 1 hour before it was allowed to reach ambient temperature and stirred for 72 hours. The reaction mixture was diluted with water, and extracted several times with ethyl acetate. The combined organic layers were dried and evaporated to afford the crude product. Chromatography, with hexane:ethyl acetate (2:1) as the eluent, gave a mixture of the alcohol and starting material (2.98 g); NMR (CDCl$_3$): 1.95–2.04 (m,4), 2.9 (broad,2), 3.90 (s,3), 5.15 (s,2), 6.93–6.99 (m,2), 7.21–7.36 (m,7); MS: m/z=342(M+1). This material was used in the next step without further purification.

c. 1-Benzyloxycarbonyl-4-(2-methoxyphenyl)piperidine. A solution of 1-benzyloxycarbonyl-4-hydroxy-4-(2-methoxyphenyl)-piperidine (2.59 g) in dichloromethane (45 mL) was treated with trifluoroacetic acid (8.6 g) followed by triethylsilane (17.5 g). The resulting brown reaction mixture was stirred for 5 minutes and then poured into a saturated solution of sodium bicarbonate. The bicarbonate solution was extracted with dichloromethane. The dichloromethane solution was dried and evaporated to give the des-hydroxy compound (2.1 g); NMR (CDCl$_3$): 1.55–1.66 (m,2), 1.78–1.82 (br,2), 2.91, (m,2), 3.11 (m,1), 3.8 and 3.82 (s,3), 4.32 (br,2), 5.12–5.28 (m,2), 6.84 (d,4, J=9), 6.87–6.95 (m,1), 7.11–7.25 (m,2), 7.29–7.38 (m,5); MS: m/z=326(M+1). This material was used in the next step without further purification.

d. 4-(2-Methoxyphenyl)piperidine. A solution of 1-benzyloxycarbonyl-4-(2-methoxyphenyl)piperidine (0.67 g) in ethanol (10 mL) was treated with cyclohexene (4.2 mL) followed by 10% palladium on carbon (0.13 g). After heating to reflux for 2 hours, the reaction mixture was cooled to room temperature, diluted with ether and extracted with 1 N hydrochloric acid. The aqueous layer was made basic with sodium bicarbonate and extracted with dichloromethane. The organic layers were dried over anhydrous sodium sulfate and evaporated to afford the piperidine (0.2 g); NMR (CDCl$_3$): 1.60 (d of q,2, J$_1$=12, J$_2$=4), 1.73–1.82 (broad,2), 2.74–2.83 (d of t,2, J$_1$=12, J$_2$=2), 3.02–3.2 (m,3), 3.82 (s,3), 6.85 (d,1,J=8), 6.9 (m,1), 7.15–7.26 (m,2); MS: m/z=192(M+1). This material was used in the next step without further purification.

EXAMPLE 14

3-[1-(3,4-Dichlorophenyl)-3-(4-(2-hydroxyphenyl) piperidino)propyl]-2-methyl-2,3-dihydroisoindol-1-one hydrochloride 3-(3,4-Dichlorophenyl)-3-(2-methyl-3-oxo-2,3-dihydro-1H-isoindol-1-yl)propionaldehyde (0.368 g) was coupled to 4-(2-methoxyphenyl)piperidine (0.177 g) by a method similar to that described in Example 8. The reaction product was not purified by chromatography but converted to the corresponding hydrochloride salt as described in the Example 8 to afford the title compound (0.424 g); mp 150–160° C.; MS: m/z=508(M+1); NMR(CD$_3$SOCD$_3$): 1.93–2.08 (m,4), 2.75 (m,1), 3.07 (s,3), 3.39 (m,5), 3.67–3.71 (m,32), 4.87 (d,1, J=3.7), 6.77–6.80 (m,3), 6.97–7.07 (m,3), 7.31 (m,1), 7.50 (m,2), 7.67 (m,1), 7.94 (d,1, J=7.7). Analysis for C$_{29}$H$_{29}$Cl$_2$N$_2$O$_2$. 1.5 HCl.0.5 H$_2$O: Calculated: C, 60.88; H, 5.55, N, 4.90; Found: C, 61.09; H, 5.64; N, 4.73.

The intermediate 4-(2-hydroxyphenyl)piperidine was prepared as follows:

a. 2-Benzyloxybromobenzene. A solution of 2-bromophenol (17.3 g) in dimethylformamide (200 mL) was treated with potassium carbonate (15.2 g) followed by benzyl bromide (17.1 g, 11.9 mL). After stirring for 3 hours at the room temperature, the reaction mixture was diluted water and hexane. The aqueous layer was extracted with hexane; and the organic layers were washed (water, 1 N sodium hydroxide, brine), dried and evaporated to give the product as a colorless oil (22.94 g). This material was fractionally distilled under reduced pressure to afford the bromobenzene (16.52 g); bp 110–145° C. (1333 Pa); NMR (CDCl$_3$): 5.17 (s,2), 6.65 (d of t,1, J=8, J=1), 6.92–6.96 (d of d,1, J=8, J=1), 7.19–7.26 (m,1), 7.33–7.42 (m,3), 7.46–7.50 (m,2), 7.55 (d of d,1, J=9, J=2). This material was used in the next step without further purification.

b. 1-Benzyloxycarbonyl-4-hydroxy-4-(2-benzyloxyphenyl)-piperidine. Using a procedure similar to that described in Example 12 sub-part b., except using 2-benzyloxybromobenzene, the crude hydroxy compound was prepared. The resulting product was chromatographed, with hexane:isopropanol (9:1) as the eluent, to give the hydroxy compound (2.86 g); NMR (CDCl$_3$): 2.04 (m,4), 3.4 (broad,2), 4.0–4.1 (broad,3), 5.13–5.16 (m,4), 6.96–7.02 (m,2), 7.22–7.27 (m,3), 7.30–7.41 (m,9); MS: m/z=418(m+1).

c. 1-Benzyloxycarbonyl-4-(2-benzyloxyphenyl) piperidine. 1-Benzyloxycarbonyl-4-hydroxy-4-(2-benzyloxyphenyl)piperidine was subjected to a procedure similar to that described in Example 13 sub-part c. The resulting product was chromatographed, with hexane:ethyl acetate (3:1) as the eluent, to give the piperidine (1.67 g, contaminated with an impurity); NMR (CDCl$_3$): 1.60–1.64 (m,2), 1.84 (broad,2), 2.89 (broad, 2), 3.15–3.2 (m,1), 4.31 (s,2), 5.09 (d,2, J=7), 5.17 (d,2), 6.91–7.15 (m,2), 7.17–7.21 (m,2), 7.25–7.41 (m,10); MS: m/z=402(M+1). This material was used in the next step without any further purification.

d. 4-(2-Hydroxyphenyl)piperidine. 1-Benzyloxycarbonyl-4-(2-benzyloxyphenyl) piperidine was subjected to a procedure similar to that described in Example 10 sub-part c. to give 4-(2-hydroxyphenyl)-piperidine as a brown solid (0.36 g); NMR (CDCl$_3$): 1.7–1.9 (m,4), 2.77–2.86 (m,2), 2.99–3.04 (m,1), 3.23 (d,2, J=12), 4.17 (s,2), 6.72 (d,1, J=8), 6.84 (t,1, J=7), 7.05 (m,1); MS: m/z=178(M+1). This material was used in the next step without further purification.

EXAMPLE 15

3-[1-(3,4-Dichlorophenyl)-3-(4-(2-oxoperhydropyrimidine-1-yl)piperidino)propyl]-2-methyl-2,3-dihydroisoindol-1-one hydrochloride 3-(3,4-Dichlorophenyl)-3-(2-methyl-3-oxo-2,3-dihydro-1H-isoindol-1-yl)propionaldehyde (0.333 g) was coupled to 4-(2-oxoperhydropyrimidine-1-yl)piperidine (0.183 g) by a method similar to that described in Example 8. The reaction product was purified by chromatography and converted to the corresponding hydrochloride salt as described in Example 8 to afford the title compound (0.424 g); mp 160–185° C.; MS: m/z=514(M+1); NMR(CD$_3$SOCD$_3$): 1.65 (d,2, J=13), 1.78 (s,1), 2.18 (m,2), 3.06 (s,3) 4.39 (m,1), 4.87 (d,1, J=3.5), 6.77 (d,1, J=8.4), 6.96 (s,1), 7.33 (d,1, J=8.3), 7.50 (m,2), 7.67 (m,1), 7.94 (d,1, J=7.6). Analysis for C$_{27}$H$_{32}$Cl$_2$N$_4$O$_2$.2.0 HCl .0.5 H$_2$O: Calculated: C, 54.28; H, 5.90, N, 9.37; Found: C, 54.36; H, 5.86; N, 9.10.

The intermediate 4-(2-oxoperhydropyrimidine-1-yl) piperidine was prepared as described in Example 16 sub-parts e.–h.

EXAMPLE 16

3-[1-(3,4-Dichlorophenyl)-3-(4-(2-oxoperhydropyrimidine-1-yl)piperidino)propyl]-6-methoxy-2-methyl-2,3-dihydroisoindol-1-one hydrochloride 3-(3,4-Dichlorophenyl)-3-(5-methoxy-2-methyl-3-oxo-2,3-dihydro-1H-isoindol-1-yl)propionaldehyde (0.378 g) was coupled to 4-(2-oxoperhydropyrimidine-1-yl)piperidine (0.22 g) by a method similar to that described in Example 8, to give the title compound (0.420 g); mp 165–175° C. (d); MS: m/z=545(M+1); NMR(CD$_3$SOCD$_3$): 1.65 (d,2, J=12), 1.78 (s,2), 2.18 (m,2), 3.08 (s,3), 3.8 (s,3), 4.78 (d,1, J=3.5), 6.77 (d,1, J=8.5), 7.01 (s,2), 7.18 (dd,1, J=8.3, 2.4), 7.35 (d,1, J=8.2), 7.8 (d,1, J=8.4). Analysis for C$_{28}$H$_{34}$Cl$_2$N$_4$O$_3$.1.5 HCl.1.5 H$_2$O: Calculated: C, 53.61; H, 6.18, N, 8.93; Found: C, 53.56; H, 6.01; N, 8.33.

The intermediate 3-(3,4-Dichlorophenyl)-3-(5-methoxy-2-methyl-3-oxo-2,3-dihydro-1H-isoindol-1-yl) propionaldehyde was synthesized as follows.

a. N-methyl-2-bromo-5-methoxybenzamide. A solution of 2-bromo-5-methoxybenzoic acid (50 g) in dichloromethane (500 mL) was cooled in ice and treated with dimethylformamide (1 mL) followed by oxalylchloride (29 mL). Upon stirring for 1 hour the ice bath was removed and the reaction mixture was stirred for additional 3 hours and the volatile material was removed by evaporation. The residue was dissolved in dichloromethane (500 mL), cooled in ice and treated with a 40% aqueous solution of methylamine. Upon stirring at room temperature for 16 hours, the reaction mixture was diluted with ethyl acetate and acidified with hydrochloric acid. The aqueous layer was extracted with ethyl acetate and the organic layers were washed with sodium bicarbonate solution. The combined organics were dried and evaporated to give N-methyl-2-bromo-5-methoxybenzamide as a white crystalline solid (47.54 g); mp 154–157° C.

b. 3-[1-(3,4-Dichlorophenyl)but-3-enyl]-3-hydroxy-6-methoxy-2-methyl-2,3-dihydroisoindol-1-one. A solution of N-methyl-2-bromo-5-methoxybenzamide (4.88 g) in tetrahydrofuran (100 mL) was cooled to −76° C. and treated with n-butyl lithium (16 mL of 2.5 M solution) slowly such that the temperature of the reaction mixture remained below −72° C. Upon stirring the resulting yellow solution at −76° C. for 1 hour, a solution of 2-(3,4-dichloropheny)pent-4-enoic acid ethyl ester (5.46 g) in tetrahydrofuran was added. The reaction mixture was stirred at −76° C. for 15 minutes and allowed to warm to 0° C. and stirred at that temperature for 30 minutes. At the end of this period 10% aqueous hydrochloric acid was added (100 mL) and the reaction mixture was extracted with ethyl acetate. The aqueous layer was extracted with additional 300 mL of ethyl acetate and the organic layers were washed with sodium bicarbonate solution, dried, and evaporated. The resulting material was refluxed with ethyl acetate (50 mL) and filtered to obtain 3-[1-(3,4-dichlorophenyl)-but-3-enyl]-3-hydroxy-6-methoxy-2-methyl-2,3-dihydroisoindol-1-one as a white solid (1.27 g); MS: m/z=392(M+1); NMR (CDCl$_3$): 2.54 (m,1), 2.90 (s,3), 3.15 (m,1), 3.34 (dd,1, J=12, 3), 3.85 (s,3), 4.91 (m,2), 5.50 (m,1), 6.37 (dd, J=6, 2), 6.65 (d,1, J=2), 7.08–7.18 (m,3), 7.65 (d,1, J=8).

c. 3-[1-(3,4-Dichlorophenyl)but-3-enyl]-6-methoxy-2-methyl-2,3-dihydroisoindol-1-one. A solution of 3-[1-(3,4-dichlorophenyl)-but-3-enyl)-3-hydroxy-6-methoxy-2-methyl-2,3-dihydroisoindol-1-one (1.0 g) in dichloroethane (100 mL) was treated with sodium cyanoborohydride (1.28 g) and zinc iodide (1.22 g). After stirring at room temperature for 16 hours, the reaction mixture was treated with 10% aqueous hydrochloric acid and stirred for 1 hour. The reaction mixture was extracted with ethyl acetate and the organic layer was washed (aqueous sodium sulfite), dried and evaporated to afford the crude product. This material was purified by chromatography, with hexane:isopropanol (9:1) as the eluent to give 3-[1-(3,4-dichloro-phenyl) but-3-enyl]-6-methoxy-2-methyl-2,3-dihydroisoindol-1-one (0.486 g); MS: m/z=376; NMR(CDCl$_3$): 2.74 (t, J=7, 2), 3.10 (s,3), 3.38 (m,1), 4.62 (d,1, J=3.8), 5.10 (m,2), 5.71 (m,1), 6.53 (dd,1, J=8, 2), 6.82 (d,1, J=2), 7.11–7.26 (m,3), 7.48 (d,1, J=8.4).

d. 3-(3,4-Dichlorophenyl)-3-(5-methoxy-2-methyl-3-oxo-2,3-dihydro-1H-isoindol-1-yl)propionaldehyde. The aldehyde was prepared from 3-[1-(3,4-dichlorophenyl)but-3-enyl]-6-methoxy-2-methyl-2,3-dihydroisoindol-1-one (7.44 g) using a procedure similar to that described in Example 2 sub-part d. Purification by chromatography gave the desired aldehyde (4.52 g); MS: m/z=378(M+1); NMR (CDCl$_3$): 3.06 (s,3), 3.84 (s,3), 4.60 (d,1, J=3.6), 6.65 (dd,1, J=8, 2), 6.93 (m,1), 7.12–7.49 (m,5), 9.76 (s,1).

The intermediate 4-(2-oxoperhydropyrimidine-1-yl) piperidine was prepared as follows.

e. N-Benzyloxycarbonyl-4-piperidone. A solution of 4-piperidone hydrochloride (70 g) in 1.4 L of saturated sodium bicarbonate solution was treated dropwise with a solution of benzyloxycarbonylchoride (75 mL) in 40 mL of dioxane. The reaction mixture was stirred over night and extracted with three portions of ethyl acetate. The organic layers were washed (1N hydrochloric acid, water, and brine) dried and evaporated to give an oil (96.62 g).

f. 1-Benzyloxycarbonyl-4-(3-aminopropylamino) piperidine. N-benzyloxycarbonyl-4-piperidone and 1,3-diaminopropane were reductively coupled using a procedure similar to that described in Example 1. The reaction mixture was evaporated, and the residue was dissolved in 1 N hydrochloric acid. Concentrated hydrochloric acid was added dropwise and stirring was continued until the evolution of gas ceased. The acidic aqueous mixture was washed with dichloromethane, made basic to pH 10 with 10 N sodium hydroxide, and extracted with dichloromethane. The dichloromethane extracts were dried and evaporated to give 1-benzyloxycarbonyl-4-(3-aminopropyl-amino) piperidine as a viscous oil; MS: m/z=292(M+1); NMR (CD$_3$OD): 7.34 (m,5), 5.10 (s,2), 4.13 (m,2), 2.86 (m,2), 2.65 (m,5), 1.90 (m,2), 1.65 (m,2), 1.23 (m,2).

g. 1-Benzyloxycarbonyl-4-(2-oxoperhydropyrimidin-1-yl)-piperidine. A stirred solution of 1-benzyloxycarbonyl-4-(3-aminopropylamino) piperidine (10.1 g) and 1,1'-carbonyldiimidazole (6.2 g) in chloroform (250 mL) was heated at reflux for 2 hours. The mixture was washed with water, and the separated organic phase was dried, evaporated, and chromatographed, with dichloromethane/methanol (90:10) as eluent, to give the urea as a white solid (7.4 g); MS: m/z=318(M+1); NMR (CDCl$_3$): 7.35 (m,5), 5.12 (s,2), 4.75 (m,1), 4.50 (m,1), 4.26 (m,2), 3.27 (m,2), 3.13 (m,2), 1.89 (m,2), 1.63 (m,4).

h. 4-(2-Oxoperhydropyrimidine-1-yl)piperidine. 1-Benzyloxycarbonyl-4-(2-oxoperhydropyrimidin-1-yl)piperidine was treated with trifluoroacetic acid using a procedure similar to that described in Example 66 sub-part h. The reaction product was purified by chromatography to give the piperidine.

EXAMPLE 17

3-[1-(3,4-Dichlorophenyl)-3-(4-(3-pyridyl) piperidino)-propyl]-6-methoxy-2-methyl-2,3-dihydroisoindol-1-one hydrochloride 3-(3,4-Dichlorophenyl)-3-(5-methoxy-2-methyl-3-oxo-2,3-dihydroy-1H-isoindol-1-yl)propionaldehyde (0.378 g) was coupled to 4-(3-pyridyl)piperidine (0.162 g) by a method similar to that described in Example 8. The reaction product was not purified by chromatography but converted to the corresponding hydrochloride salt as described in the Example 8 to afford the title compound (0.447 g); mp 165–220° C. (d)z; MS: m/z=524(M+1); NMR(CD$_3$SOCD$_3$): 2.12 (m,5), 3.06 (s,3), 3.8 (s,3), 4.8 (m,1), 6.77 (m,1), 7.04 (m,2), 7.06 (m,1), 7.18 (m,1), 7.32 (m,1), 7.86 (m,1), 8.00 (m,1), 8.39 (m,1), 8.82 (m,2). Analysis for C$_{29}$H$_{31}$Cl$_2$N$_3$O$_2$.2.0 HCl.2.5 H$_2$O: Calculated: C, 54.35; H, 5.94, N, 6.56; Found: C, 54.36; H, 5.75; N, 6.01.

EXAMPLE 18

3-[1-(3,4-Dichlorophenyl)-3-(4-(2-methylsulfinylphenyl)-piperidino)propyl]-6-methoxy-2-methyl-2,3-dihydroisoindol-1-one hydrochloride 3-(3,4-Dichlorophenyl)-3-(2-methyl-3-oxo-2,3-dihydro-5-methoxy-1H-isoindol-1-yl)propionaldehyde (0.38 g) was coupled to 4-(2-methylsulfinylphenyl)piperidine (0.29 g) by a method similar to that described in Example 8. The reaction product was purified by chromatography and converted to the corresponding hydrochloride salt as described in Example 8 to afford the title compound (0.447 g); mp 155–178° C. (d); MS: m/z=585(M+1); NMR(CD$_3$OD): 2.0–2.3 (m,4), 2.6 (m,2), 2.8–3.0 (m,3), 3.0–3.3 (m,7), 3.5–3.8 (m,4), 3.85 (s,3) 4.8 (d,1, J=4), 6.7–7.3 (m,5), 7.5–8.0 (m,5). Analysis for C$_{31}$H$_{34}$Cl$_2$N$_2$O$_3$S.HCl.1.5 H$_2$O: Calculated: C, 59.86; H, 5.67, N, 4.50; Found: C, 57.05; H, 5.64; N, 4.19.

The intermediate 3-(3,4-dichlorophenyl)-3-(5-methoxy-2-methyl-3-oxo-2,3-dihydro-1H-isoindol-1-yl) propionaldehyde was synthesized as described in Example 16 subparts a.–d.

The intermediate 4-(2-methylsulfinylphenyl)piperidine was prepared as described in Example 66 sub-parts d.–h.

EXAMPLE 19

3-[1-(3,4-Dichlorophenyl)-3-(4-(5-methoxy-2-methylsufonylphenyl)-piperidino)propyl]-2-methyl-2,3-dihydroisoindol-1-one hydrochloride 3-(3,4-Dichlorophenyl)-3-(5-methoxy-2-methyl-3-oxo-2,3-dihydro-1H-isoindol-1-yl)propionaldehyde (0.38 g) was coupled to 4-(2-methylsufonylphenyl)piperidine (0.29 g) by a method similar to that described in Example 8. The reaction product was purified by chromatography and converted to the corresponding hydrochloride salt as described in the Example 8 to afford the title compound (0.447 g); mp 155–178° C. (d); MS: m/z=601(M+1); NMR(CD$_3$OD): 2.1–2.2 (m,4), 2.6 (m,2), 2.9–3.0 (m,1), 3.1–3.3 (m,9), 3.6–3.8 (m,7), 4.8 (d,1, J=4), 7.1 (d,1, J=2.4), 7.2 (d,1, J=2.8), 7.3 (d,1, J=2.8), 7.4–8.1 (m,5). Analysis for C$_{31}$H$_{34}$Cl$_2$N$_2$O$_4$S.HCl.0.5 H$_2$O: Calculated: C, 58.36; H, 5.53, N, 4.39; Found: C, 57.22; H, 5.57; N, 3.99.

EXAMPLE 20

3-[1-(3,4-Dichlorophenyl)-3-(4-(2-fluoro-3-pyridyl)-piperidino)propyl]-6-methoxy-2-methyl-2,3-dihydroisoindol-1-one hydrochloride 3-(3,4-Dichlorophenyl)-3-(5-methoxy-2-methyl-3-oxo-2,3-dihydro-1H-isoindol-1-yl)propionaldehyde (0.38 g) was coupled to 4-(2-fluoro-3-pyridyl)piperidine (0.47 g) by a method similar to that described in Example 8. The reaction product was purified by chromatography and converted to the corresponding hydrochloride salt as described in the Example 8 to afford the title compound (0.25 g); mp 99–148° C. (d); MS: m/z=542(M+1); NMR(CD$_3$OD): 2.1 (m,4), 2.5–2.6 (m,2), 2.9 (m,1), 3.1–3.2 (m,5), 3.6–3.8 (m,6), 4.8 (d,1, J=4), 6.7–7.5 (m,6), 7.8–8.1 (m,3). Analysis for C28H30Cl$_2$N$_3$O$_2$F.HCl.H$_2$O: Calculated: C, 58.35; H, 5.57, N, 7.04; Found: C, 57.99; H, 5.47; N, 7.18.

EXAMPLE 21

3-[1-(3,4-Dichlorophenyl)-3-(4-acetamido-4-phenylpiperidino)propyl]-6-methoxy-2-methyl-2,3-dihydroisoindol-1-one hydrochloride 3-(3,4-Dichlorophenyl)-3-(5-methoxy-2-methyl-3-oxo-2,3-dihydro-1H-isoindol-1-yl)propionaldehyde (0.38 g) was coupled to 4-acetamido-4-phenylpiperidine (0.29 g) by a method similar to that described in Example 8. The reaction product was purified by chromatography and converted to the corresponding hydrochloride salt as described in the Example 8 to afford the title compound (0.7 g); mp 182–210° C. (d); MS: m/z=580(M+1); NMR(CD$_3$OD): 2.1 (s,3), 2.3 (m,2), 2.9 (m,1), 2.6 (m,2), 2.7–3.0 (m,3), 3.1–3.3 (m,7), 3.6–3.7 (m,3), 3.95 (s,3), 4.9 (m,1), 6.7 (dd,1, J=8, 2), 6.9 (d,1, J=2), 7.2 (d,1, J=2), 7.2–7.4 (m,8), 7.8 (d,1, J=8), 7.8–8.1 (m,3). Analysis for C32H $_{34}$Cl$_2$N$_3$O$_3$.HCl.H$_2$O: Calculated: C, 60.53; H, 6.03, N, 6.62; Found: C, 60.47; H, 5.93; N, 6.43.

The intermediate 3-(3,4-dichlorophenyl)-3-(5-methoxy-2-methyl-3-oxo-2,3-dihydro-1H-isoindol-1-yl) propionaldehyde was synthesized as described previously for Example 16 above.

EXAMPLE 22

3-[1-(3,4-Dichlorophenyl)-3-(4-(2-methoxy-3-pyridyl)-piperidino)propyl]-6-methoxy-2-methyl-2,3-dihydroisoindol-1-one hydrochloride 3-(3,4-Dichlorophenyl)-3-(5-methoxy-2-methyl-3-oxo-2,3-dihydro-1H-isoindol-1-yl)propionaldehyde (0.38 g) was coupled to 4-(2-methoxy-3-pyridyl)piperidine (0.60 g) by a method similar to that described in Example 8. The reaction product was purified by chromatography and converted to the corresponding hydrochloride salt as described in the Example 8 to afford the desired title compound (0.26 g); mp 135–194° C. (d); MS: m/z=554(M+1); NMR(CD$_3$OD): 1.9–2.1 (m,4), 2.6 (m,2), 2.9–3.1 (m,8), 3.6–3.8 (m,4), 3.8 (s,3), 4.0 (s,3), 4.8 (d,1, J=4), 6.7–8.1 (m,9). Analysis for C$_{30}$H$_{33}$Cl$_2$N$_3$O$_3$.1.5 HCl-0.5 H$_2$O: Calculated: C, 58.29; H, 5.79, N, 6.80; Found: C, 58.25; H, 5.71; N, 6.68.

The intermediate 3-(3,4-dichlorophenyl)-3-(5-methoxy-2-methyl-3-oxo-2,3-dihydro-1H-isoindol-1-yl)propionaldehyde was synthesized as described previously for Example 16 above.

EXAMPLE 23

3-[1-(3,4-Dichlorophenyl)-3-(4-(6-methoxy-2-methylthio-3-pyridyl)-piperidino)propyl]-2-methyl-2,3-dihydroisoindol-1-one hydrochloride 3-(3,4-Dichlorophenyl)-3-(5-methoxy-2-methyl-3-oxo-2,3-dihydro-1H-isoindol-1-yl)propionaldehyde (0.38 g) was coupled to 4-(2-methylthio-3-pyridyl)piperidine (0.23 g) by a method similar to that described in Example 8. The reaction product was purified by chromatography and converted to the corresponding hydrochloride salt as described in the Example 8 to afford the title compound (0.38 g); mp 122–158° C. (d); MS: m/z=570(M+1); NMR(CD$_3$OD): 2.0–2.2 (m,4), 2.5–2.7 (m,2), 2.7–2.9 (m,4), 3.1–3.3 (m,4), –3.8 (m,5), 4.8 (d,1, J=4, 3), 6.7–7.2 (m,5), 7.5–8.5 (m,4). Analysis for C$_{30}$H$_{33}$Cl$_2$N$_3$O$_2$S.2.0 HCl.1.0 H2O: Calculated: C, 54.47; H, 5.64, N, 6.35; Found: C, 54.22; H, 5.52; N, 6.27.

EXAMPLE 24

3-[1-(3,4-Dichlorophenyl)-3-(4-(2-methylsulfinyl-3-pyridyl)piperidino)propyl]-6-methoxy-2-methyl-2,3-dihydroisoindol-1-one hydrochloride 3-(3,4-Dichlorophenyl)-3-(5-methoxy-2-methyl-3-oxo-2,3-dihydro-1H-isoindol-1-yl)propionaldehyde (0.33 g) was coupled to 4-(2-methylsulfinyl-3-pyridyl)piperidine(0.423 g) by a method similar to that described in Example 8. The reaction product was purified by chromatography and converted to the corresponding hydrochloride salt as described in the Example 8 to afford the title compound (0.26 g); mp 120–182° C. (d); MS: m/z=586(M+1); NMR(CD$_3$OD): 2.0–2.3 (m,4), 2.6 (m,2), 2.9 (m,5), 3.2–3.3 (m,4), 3.6–3.9 (m,8), 4.8 (m,1), 6.7–7.3 (m,5), 7.5–8.1 (m,3), 8.7 (broad,1). Analysis for C$_{30}$H$_{33}$Cl$_2$N$_3$O$_3$S.2.0 HCl.1.0 H$_2$O: Calculated: C, 53.18; H, 5.50, N, 6.20; Found: C, 53.39; H, 4.49; N, 6.53.

The intermediate 3-(3,4-dichlorophenyl)-3-(5-methoxy-2-methyl-3-oxo-2,3-dihydro-1H-isoindol-1-yl)propionaldehyde was synthesized as described previously for Example 16 above.

EXAMPLE 25

3-[1-(3,4-Dichlorophenyl)-3-(4-hydroxy-4-phenylpiperidino)propyl]-6-methoxy-2-methyl-2,3-dihydroisoindol-1-one hydrochloride 3-(3,4-Dichlorophenyl)-3-(5-methoxy-2-methyl-3-oxo-2,3-dihydro-1H-isoindol-1-yl)propionaldehyde (0.59 g) was coupled to 4-hydroxy-4-phenylpiperidine (0.27 g) by a method similar to that described in Example 8. The reaction product was purified by chromatography and converted to the corresponding hydrochloride salt as described in the Example 8 to afford the title compound (0.26 g); mp 154–180° C. (d); MS: m/z=539(M+1); NMR(CD$_3$SOCD$_3$): 1.73–1.77 (m,2), 2.0 (m,1), 3.79 (two peaks,3), 5.46 (d,1, J=9.5), 6.98 (d,1, J=8), 7.03 (m,2), 7.17–7.58 (m,7), 7.82 (d,1, J=8). Analysis for C$_{30}$H$_{32}$Cl$_2$N$_2$O$_3$.2.0 HCl: Calculated: C, 58.83; H, 5.59, N, 4.57; Found: C, 58.39; H, 5.60; N, 4.66.

EXAMPLE 26

3-1-(3,4-Dichlorophenyl)-3-(4-methylaminocarbonyl)-4-(2-oxopiperidino)piperidino)propyl]-2-methyl-2,3-dihydro-6-methoxyisoindol-1-one hydrochloride 3-(3,4-Dichlorophenyl)-3-(5-methoxy-2-methyl-3-oxo-2,3-dihydro-1H-isoindol-1-yl)propionaldehyde (0.767 g) was coupled to 4-(methylaminocarbonyl)-4-(2-oxopiperidino) piperidine (0.485 g) by a method similar to that described in Example 8. The reaction product was not purified by chromatography but converted to the corresponding hydrochloride salt as described in the Example 8 to afford the title compound (0.714 g); mp 180–185° C. (d); MS: m/z=601 (M+1); NMR(CD$_3$SOCD$_3$): 1.64–1.79 (m,4), 2.80 (m,1), 3.04 (s,3), 3.35 (s,3), 3.79 (s,3), 4.77 (d,1, J=3), 6.76 (d,1, J=8), 7.0 (s,1), 7.17 (d,1, J=6.7), 7.34 (m,1), 7.54 (m,1), 7.82 (m,1). Analysis for C$_{31}$H$_{38}$Cl$_2$N$_4$O$_4$.1.5 HCl.0.5 H$_2$O: Calculated: C, 55.97; H, 6.14, N, 8.02; Found: C, 55.62; H, 6.11; N, 7.81.

The intermediate 4-(methylaminocarbonyl)-4-(2-oxopiperidino)piperidine was prepared as follows.

a. 8-Benzyl-1,3,8-triazaspiro[4.5]decane-2,4-dione. 1-Benzyl-4-piperidone (100 g) was added in a single portion to a mechanically stirred suspension of ammonium carbonate (488.5 g) and sodium cyanide (70.0 g) in water (700 mL) and ethanol (700 mL). The reaction mixture was stirred at 60° C. for 12 hours. The inorganic salts dissolve gradually in the solution and spirohydantoin crystals formed. Upon cooling to room temperature, the solids were collected by filtration, washed with warm water (2 L), recrystallized from 80% ethanol (2 L), washed with ethanol, and dried in a vacuum oven at 50° C. to give the hydantoin (122 g) as a white solid; MS: m/z=260(M+1); NMR (DMSO-d$_6$): 10.64 (bs,1), 8.45 (broad s,1), 7.29 (m,5), 3.48 (s,2), 2.69 (m,2), 2.28 (m,2), 1.81 (m,2), 1.51 (m,2).

b. 4-Amino-1-benzyl-4-carboxypiperidine. A stirred solution of the hydantoin (40.0 g) and lithium hydroxide monohydrate (32.4 g) in water (500 mL) was heated at reflux for 40 hours. The mixture was cooled to room temperature, filtered to remove the white precipitate, and the filtrate evaporated. The pH of the concentrate was adjusted from 12 to 5 with concentrated hydrochloric acid and the solution was evaporated to dryness. The residue was suspended in methanol to provide a white precipitate that was filtered, washed with methanol, and air-dried to give the amine (32.7 g) as a white solid; MS: m/z=235(M+1); NMR (DMSO-d$_6$): 7.40 (m,5), 3.89 (m,2), 2.92 (m,4), 2.12 (m,2), 1.84 (m,2).

c. 4-Amino-1-benzyl-4-ethoxycarbonylpiperidine. Thionyl chloride (43.0 mL) was added dropwise to a suspension of the amino-acid (23.0 g) in ethanol (400 mL)

at 0° C. to give a clear solution. The reaction mixture was warmed to room temperature, refluxed for 5 hours, and stirred overnight at room temperature. The mixture was evaporated and stripped twice from toluene. The resulting oil was dissolved in water, adjusted to pH 3 with 1 N sodium hydroxide, neutralized with saturated aqueous sodium bicarbonate, and extracted with dichloromethane. The organic extracts were dried and evaporated to give the ester (21.5 g) as an oil; MS: m/z=263(M+1); NMR: 7.28 (m,5), 4.17 (q,2, J=7.1), 3.52 (s,2), 2.50 (m,4), 2.13 (m,2), 1.54 (m,4), 1.27 (t,3, J=7.1).

d. 1-Benzyl-4-(5-chlorovaleramido)-4-ethoxycarbonylpiperidine. 5-Chlorovaleryl chloride (13.2 g) in dichloromethane (50 mL) was added dropwise to a solution of the above amino-ester (20.3 g) and pyridine (13.1 mL) in dichloromethane (250 mL) at 0° C., resulting in the formation of a thick slurry within 20 minutes. After being warmed to room temperature overnight, the slurry was diluted with aqueous sodium bicarbonate to give a clear, biphasic solution, which was further extracted with dichloromethane. The organic extracts were dried and evaporated to a light brown semi-solid. The material was suspended in ether and filtered to give the amide (16.8 g) as a white solid; MS: m/z=381(M+1); NMR (CD$_3$OD): 7.28 (m,5), 4.11 (q,2, J=7.1), 3.55 (m,4), 2.68 (m,2), 2.26 (m,4), 2.05 (m,4), 1.75 (m,4), 1.21 (t,3, J=7.1).

e. 1-Benzyl-4-ethoxycarbonyl-4-(2-oxopiperidino) piperidine. A solution of the above amide (16.8 g) in tetrahydrofuran (50 mL) was cannulated into a suspension of sodium hydride (2.1 g) in tetrahydrofuran (150 mL). After being stirred overnight, the reaction mixture was quenched with water, concentrated (to remove tetrahydrofuran), diluted with water, and extracted with dichloromethane. The combined organic extracts were dried and evaporated. The crude product was chromatographed, with dichloromethane:methanol (gradient 97:3, 95:5) as eluent, to give 1-benzyl-4-ethoxycarbonyl-4-(2-oxopiperidino)piperidine (13.2 g) as a solid; MS: m/z=345(M+1); NMR (CD$_3$OD): 7.30 (m,5), 4.11 (q,2, J=7.1), 3.54 (s,2), 3.44 (m,2), 2.66 (m,2), 2.52 (m,2), 2.32 (m,2), 2.20 (m,2), 2.01 (m,2), 1.85 (m,2), 1.74 (m,2), 1.20 (t,3, J=7.1).

f. 4-Ethoxycarbonyl-4-(2-oxopiperidino)piperidine. A solution of 1-benzyl-4-ethoxycarbonyl-4-(2-oxopiperidino)piperidine (12.4 g) and 20% palladium hydroxide on carbon (2.0 g) in ethanol (150 mL) was stirred overnight under hydrogen (1 bar). The reaction mixture was filtered through diatomaceous earth, and the filtrate was evaporated to give 4-ethoxycarbonyl-4-(2-oxopiperidino)piperidine (9.1 g) as a viscous oil; MS: m/z=255(M+1); NMR (CD$_3$OD): 4.13 (q,2, J=7.1), 3.44 (m,2), 2.95 (m,4), 2.32 (m,2), 2.19 (m,2), 1.88 (m,4), 1.74 (m,2), 1.23 (t,3, J=7.1).

g. 1-Benzyloxycarbonyl-4-(ethoxycarbonyl)-4-(2-oxopiperidino)-piperidine. 4-Ethoxycarbonyl-4-(2-oxopiperidino)piperidine (9.0 g) in dichloromethane (25 mL) was added to a solution of N-(benzyloxycarbonyloxy)succinimide (8.8 g) and triethylamine (5.4 mL) in dichloromethane (150 mL). After 1.5 hours, the reaction mixture was washed successively with 1.0 N hydrochloric acid and saturated aqueous sodium bicarbonate. The separated organic layer was dried and evaporated to give 1-benzyloxycarbonyl-4-(ethoxycarbonyl)-4-(2-oxopiperidino)piperidine (11.6 g) as a light yellow solid; MS: m/z=389(M+1); NMR (CDCl$_3$/CF$_3$COOH): 7.37 (m,5), 5.16 (s,2), 4.28 (q,2, J=7.1), 4.09 (m,2), 3.40 (m,2), 3.28 (m,2), 2.53 (m,2), 2.34 (m,2), 1.83 (m,6), 1.30 (t,3, J=7.1).

h. 1-Benzyloxycarbonyl-4-carboxy-4-(2-oxopiperidino) piperidine. A solution of 1-benzyloxycarbonyl-4-ethoxycarbonyl-4-(2-oxo-piperidino)piperidine (11.4 g) in tetrahydrofuran (150 mL), 1.0 N sodium hydroxide (50 mL), and methanol (volume necessary to obtain clear solution) was heated at reflux for 10 hours. The reaction mixture was evaporated and the resulting aqueous solution was diluted with water and extracted with dichloromethane to recover unreacted starting material (3.7 g). The aqueous phase was acidified to pH 3 with 1.0 N hydrochloric acid and extracted with dichloromethane. The combined organic extracts were washed with water, dried, and evaporated to furnish a light yellow solid. The material was suspended in ether and filtered to give the acid (6.3 g) as a white solid; MS: m/z=361(M+1); NMR (CDCl$_3$/CF$_3$COOH): 7.37 (m,5), 5.17 (s,2), 4.11 (m,2), 3.45–3.32 (m,4), 2.55 (m,2), 2.37 (m,2), 1.94–1.78 (m,6).

i. 1-Benzyloxycarbonyl-4-(methylaminocarbonyl)-4-(2-oxoperhydropyrimidin-1-yl)piperidine. A solution of 1-benzyloxycarbonyl-4-carboxy-(2-oxoperhydropyrimidin-1-yl)piperidine (1.45 g), methylamine hydrochloride (0.32 g), 4-(dimethylamino)pyridine (0.59 g), triethylamine (0.67 mL), and 1-(3-dimethylaminopropyl)-3-ethyl-carbodiimide hydrochloride (0.92 g) in dichloromethane (20 mL) was stirred overnight. The reaction mixture was diluted with dichloromethane and washed successively with 1.0 N hydrochloric acid, saturated aqueous sodium bicarbonate, and water. The separated organic layer was dried and evaporated to give the anide (1.37 g) as a white solid which did not require purification; NMR (CD$_3$OD): 7.35 (m,5), 5.11 (s,2), 3.71 (m,2), 3.36 (m,2), 3.19 (m,2), 2.69 (s,3), 2.14 (m,2), 1.96 (m,4).

j. 4-(Methylaminocarbonyl)-4-(2-oxopiperidino) piperidine. 1-Benzyloxycarbonyl-4-(methylaminocarbonyl)-4-(2-oxoperhydropyrimidin-1-yl)piperidine was subjected to a procedure similar to that in Example 10 sub-part c. to give the piperidine; MS: m/z=241(M+1); NMR (CD$_3$OD): 3.41 (m,2), 3.19 (m,2), 3.05 (m,2), 2.89 (m,2), 2.69 (s,3), 2.16 (m,2), 2.00 (m,4).

EXAMPLE 27

3-[1-(3,4-Dichlorophenyl)-3-(4-(2-oxopiperidino) piperidino) propyl]-6-methoxy-2-methyl-2, 3-dihydroisoindol-1-one hydrochloride 3-(3,4-Dichlorophenyl)-3-(5-methoxy-2-methyl-3-oxo-2, 3-dihydro-1H-isoindol-1-yl)propionaldehyde (0.366 g) was coupled to 4-(2-oxopiperidino)piperidine (0.176 g) by a method similar to that described in Example 8. The reaction product was purified by chromatography and converted to the corresponding hydrochloride salt as described in the Example 8 to afford the title compound (0.158 g); mp 154–156° C.; MS: m/z=544(M+1); NMR(CD$_3$OD): 2.3 (m,13), 3.4 (s,3), 4.5 (m,1), 4.8 (d,1, J=3.8), 6.71 (dd,1, J=2, 8.4), 6.9 (d,1, J=2), 7.13 (d,1, J=2.4), 7.24 (m.2), 7.77 (d,1, J=8.4). Analysis for C$_{29}$H$_{35}$Cl$_2$N$_3$O$_3$.1.0 HCl.1.1 H$_2$O: Calculated: C, 59.95; H, 6.24, N, 7.23; Found: C, 57.97; H, 6.24; N, 6.73.

EXAMPLE 28

3- [1-(3,4-Dichlorophenyl)-3-(4-hydroxy-4-phenylpiperidino)propyl]-7-methoxy-2-methyl-2, 3-dihydroisoindol-1-one hydrochloride 3-(3,4-Dichlorophenyl)-3-(4-methoxy-2-methyl-3-oxo-2, 3-dihydro-1H-isoindol-1-yl)propionaldehyde (0.95 g) was coupled to 4-hydroxy-4-phenylpiperidine (0.44 g) by a method similar to that described in Example 8. The reaction product was purified by chromatography and converted to the corresponding hydrochloride salt as described in the Example 8 to afford the title compound (0.838 g); mp 163–185° C.; MS: m/z=539(M+1); NMR(CD$_3$SOCD$_3$): 1.78 (m,2), 2.10 (m,1), 2.98–3.22 (two peaks,3), 3.77 (s,3), 4.77 (m,1), 5.45 (m,1) 6.69–7.58 (m,11). Analysis for C$_{30}$H$_{32}$Cl$_2$N$_3$O$_2$.1.0.HCl,1.0H$_2$O: Calculated: C, 60.66; H, 5.94, N, 4.71; Found: C, 60.67; H, 5.94; N, 4.71.

The intermediate 3-(3,4-dichlorophenyl)-3-(4-methoxy-2-methyl-3-oxo-2,3-dihydro-1H-isoindol-1-yl) propionaldehyde was synthesized as described below.

a. 2-Methoxy-N-methylbenzamide. To a solution of 2-methoxybenzoyl chloride (12 g) in tetrahydrofuran (50 mL) at 0° C. was added aqueous solution of methyl amine (12 g). After stirring for 15 minutes the reaction mixture was stirred for 7 days at ambient temperature and diluted (water). Upon extraction with ethyl acetate and dichloro-methane, the organic layers were washed (water), dried, and evaporated to afford an oil. This material was distilled under reduced pressure to afford the amide; bp 160° C. (225 torr); MS: m/z=166(M+1); NMR: 3.0 (d,3 J=4.8), 3.92 (s,3), 6.96 (d,1 J=8.4), 7.04 (m,1), 7.41 (m,1), 7.90 (broad,1), 8.20 (dd,1, J=7.8, 1.8).

b. 3-[1-(3,4-Dichlorophenyl)but-3-enyl]-3-hydroxy-7-methoxy-2-methyl-2,3-dihydroisoindol-1-one. To a solution of 2-methoxy-N-methylbenzamide (2.0 g) in tetrahydrofuran (70 mL) at −40° C. was added a solution of 14.25 mL of 1.7 M solution of tert-butyllithium in pentane. This solution was stirred at −40° C. for 1 hour, warmed to −30° C. for 30 minutes and then cooled back to −40° C. A solution of 2-(3,4-dichloropheny)pent-4-enoic acid ethyl ester (3.3 g) in tetrahydrofuran (25 mL) was added to the reaction mixture. Upon stirring at −40° C. for 15 minutes the reaction mixture was warmed to 10° C. and treated with an aqueous solution of ammonium chloride, diluted (water) and extracted with ethyl acetate. The organic layer was dried and evaporated to afford the crude material which was purified by chromatography, with dichloromethane:methanol (30:1) as the eluent to afford the alcohol (0.78 g); MS: m/z=392(M+1); NMR: 1.90 (m,1), 2.16 (m,1), 3.96 (s,3), 3.38 (dd,1, J=12, 3.41), 3.77 (s,3), 4.87 (m,2), 5.44 (m,1), 6.4 (d,1, J=7.5), 6.7 (d,1, J=7.5), 7.05 (dd,1, J=8.4, 2), 7.31 (m,3).

c. 3-[1-(3,4-Dichlorophenyl)but-3-enyl]-7-methoxy-2-methyl-2,3-dihydroisoindol-1-one. A solution of 3-[1-(3,4-dichlorophenyl)-but-3-enyl]-3-hydroxy-7-methoxy-2-methyl-2,3-dihydroisoindol-1-one (0.4 g) in trifluoroacetic acid (0.78 mL) was added triethyl silane (1.6 mL) and the reaction mixture was stirred under reflux for 16 hours. At end of this period the volatile materials were evaporaed and the residue was treated with toluene and evaporated. The resulting material was purified by chromatography, with hexane:isopropanol (7:1) as the eluent to afford des-oxy compound (0.37 g); MS: m/z=376(M+1); NMR: 2.68 (m,2), 3.05 (s,3), 3.39 (m,1), 3.92 (s,3), 4.6 (m,1), 5.08 (m,2), 5.69 (m,1), 6.37–7.53 (m,6).

d. 3-(3,4-Dichlorophenyl)-3-(4-methoxy-2-methyl-3-oxo-2,3-dihydroxy-1H-isoindol-1-yl)propionaldehyde. 3-[1-(3,4-dichlorophenyl)but-3-enyl]-7-methoxy-2-methyl-2,3-dihydroisoindol-1-one (0.35 g) was subjected to conditions similar to those described in Example 2 sub-part d. The resulting material was purifiied by chromatography, to give the aldehyde (0.25 g): MS: m/z=378(M+1); NMR: 2.89 3,17 (two peaks, 3), 3.91 and 3.94 (two peaks,3), 4.6 (m,1), 6.2–7.56 (m,6).

EXAMPLE 29

3-[1-(3,4-Dichlorophenyl)-3-(4-hydroxy-4-phenylpiperidino)propyl]-5-fluoro-2-methyl-2,3-dihydroisoindol-1-one hydrochloride 3-(3,4-Dichlorophenyl)-3-(6-fluoro-2-methyl-3-oxo-2,3-dihydro-1H-isoindol-1-yl)propionaldehyde (2.05 g) was coupled to 4-hydroxy-4-phenylpiperidine (1.0 g) by a method similar to that described in Example 8. The reaction product was purified by chromatography and converted to the corresponding hydrochloride salt as described in the Example 8 to afford the title compound (2.05 g); mp 160–205° C.; MS: m/z=527(M+1); NMR(CD$_3$SOCD$_3$): 1.78 (m,2), 2.17 (m,1), 3.12 (s,3), 4.89 (m,1), 6.88 (d,1, J=8.3), 7.10–7.59 (m,9), 7.84 (d,1, J=8.7). Analysis for C$_{29}$H$_{29}$Cl$_2$N$_2$O$_2$F.1.0 HCl.1.0 H$_2$O: Calculated: C, 59.85; H, 5.54, N, 4.81; Found: C, 60.15; H, 5.39; N, 4.81.

The intermediate 3-(3,4-dichlorophenyl)-3-(6-fluoro-2-methyl-3-oxo-2,3-dihydro-1H-isoindol-1-yl) propionaldehyde was synthesized as described below.

a. N-Methyl-4-fluorobenzamide. Using a procedure similar to that described in Example 28 sub-part a, except replacing 2-methoxybenzoyl chloride with N-methyl-4-fluorobenzoyl chloride, the amide was prepared. The product was purified by crysatllization to give a white solid (9.56 g); mp 117–122° C.; MS: m/z=154(M+1).

b. 3-[1-(3,4-Dichlorophenyl)but-3-enyl]-5-fluoro-3-hydroxy-2-methyl-2,3-dihydroisoindol-1-one. A method similar to that used in Example 2 sub-part b. was used except that N-methyl-4-fluorobenzamide (1.53 g) was used insted of N-methylbenzamide. The crude product was purified by chromatography, with hexane:isopropanol (10:1) as the eluent to give a material which was suspended in hexane and filtered to obtain the desired material as a solid (2.31 g); mp 144–156° C.; MS: m/z=380(M+1); NMR(CDCl$_3$): 1.92 (m,1), 2.73 and 2.92 (two peaks,3), 3.32 (m,1), 4.91 (m,2), 5.45 (m,1), 6.33–7.52 (m,6).

c. 3-[1-(3,4-Dichlorophenyl)but-3-enyl]-2-methyl-2,3-dihydro-5-fluoro-1-H-isoindol-1-one. 3-[1-(3,4-dichlorophenyl)but-3-enyl]-5-fluoro-3-hydroxy-2-methyl-2,3-dihydroisoindol-1-one (2.29 g) was subjected to a procedure similar to that described in Example 2 sub-part c. The crude product was purified by chromatography, with hexane:isopropanol (7:1) as the eluent to give 3-[1-(3,4-dichlorophenyl)but-3-enyl]-2-methyl-2,3-dihydro-5-fluoro-1-H-isoindol-1-one as a solid (2.11 g); MS: m/z=364(M+1); NMR (CDCl$_3$): 2.08 (m,1), 2.73 (m,1), 3.24 and 3.39 (two peaks,3), 3.51 (m,1), 4.6 (dd,1, J=15, 3.8), 4.96 (m,1), 5.17 (m,2), 5.72 (m,1), 6.44–7.8 (m,6).

d. 3-(3,4-Dichlorophenyl)-3-(6-fluoro-2-methyl-3-oxo-2,3-dihydro-1H-isoindol-1-yl)propionaldehyde. 3-[1-(3,4-Dichlorophenyl)-but-3-enyl]-2-methyl-2,3-dihydro-5-fluoro-1-H-isoindol-1-one was subjected to a procedure similar to that described in Example 2 sub-part d. to give the aldehyde (2.1 g); MS: m/z=366(M+1); NMR(CDCl$_3$): 3.06 and 3.2 (two peaks,3), 4.03 (m,2), 4.67 (dd, 1, J=14, 3.5), 6.34–7.83 (m,6), 9.78 (s,1).

EXAMPLE 30

3-[1-(3,4-Dichlorophenyl)-3-(4-hydroxy-4-phenylpiperidino)propyl]-5-methoxy-2-methyl-2,3-dihydroyisoindol-1-one hydrochloride 3-(3,4-Dichlorophenyl)-3-(6-methoxy-2-methyl-3-oxo-2,3-dihydro-1H-isoindol-1-yl)propionaldehyde (0.59 g) was coupled to 4-hydroxy-4-phenylpiperidine (0.26 g) by a method similar to that described in Example 8. The reaction product was purified by chromatography and converted to the corresponding hydrochloride salt as described in the Example 8 to afford the title compound (0.418 g); mp 145–172° C.; MS: m/z=539(M+1); NMR(CD$_3$SOCD$_3$): 1.78 (m,2), 2.17 (m,1), 3.21 (s,3), 4.80 (s,1), 6.73–7.58 (m,11). Analysis for C$_{29}$H$_{29}$Cl$_2$N$_2$O$_2$F.1.0 HCl.1.0 H$_2$O: Calculated: C, 60.66; H, 5.94, N, 4.72; Found: C, 60.77; H, 5.70; N, 4.93.

The intermediate 3-(3,4-dichlorophenyl)-3-(6-methoxy-2-methyl-3-oxo-2,3-dihydroy-1H-isoindol-1-yl)propionaldehyde was synthesized as described below.

a. 4-Methoxy-N-methylbenzamide. Using a procedure similar to that described in Example 28 sub-part a, except replacing 2-methoxybenzoyl chloride with 4-methoxybenzoyl chloride (10 g) the amide was prepared (7.22 g) as a solid: mp 111–113° C.; MS: m/z=166; NMR(CDCl$_3$): 3.0 (d, J=4.9, 3), 3.84 (s,3), 6.90 (m,2), 7.74 (m,2).

b. 3-[1-(3,4-Dichlorophenyl)but-3-enyl]-5-fluoro-3-hydroxy-2-methyl-2,3-dihydroisoindol-1-one. A method similar to that used in Example 28 sub-part b. was used except that 4-methoxy-N-methyl-benzamide (1.65 g) was used instead of 2-methoxy-N-methylbenzamide. The crude product purified by chromatography with hexane:isopropanol (10:1) as the eluent, to give the alcohol (0.89 g); MS: m/z=392(M+1); NMR(CDCl$_3$): 2.49 (m,1), 2.61 (s,3), 3.10 (m,1), 3.24 (dd,1, J=12, 2.9), 3.94 (s,3), 4.90 (m,2), 5.5 (m,1), 6.34 (dd,1, J=8.3, 2), 6.61 (d,1 J=2), 6.94 (dd,1 J=8.3, 2.2), 7.06 (d,1, J=8.3), 7.19 (d,1, J=2), 7.38 (d,1 J=8.3).

c. 3-[1-(3,4-Dichlorophenyl)but-3-enyl]-5-methoxy-2-methyl-2,3-dihydrosoindol-1-one. 3-[1-(3,4-dichlorophenyl)but-3-enyl]-5-fluoro-3-hydroxy-2-methyl-2,3-dihydroisoindol-1-one was subjected to a procedure similar to that described in Example 2 sub-part c. The crude product was purified by chromatography with hexane:isopropanol (7:10) as the eluent to give the des-oxy compound (1.47 g); MS: m/z=376 (M+1); NMR(CDCl$_3$): 2.08 (m,2), 3.6 (s,3), 3.51 (m,1), 4.6 (m,1), 4.96 (m,2), 5.57 (m,1), 6.19 (d,1, J=2), 6.87–7.71 (m,5).

d. 3-(3,4-Dichlorophenyl)-3-(6-methoxy-2-methyl-3-oxo-2,3-dihydroy-1H-isoindol-1-yl)propionaldehyde. 3-[1-(3,4-dichlorophenyl)but-3-enyl]-5-methoxy-2-methyl-2,3-dihydrosoindol-1-one was subjected to a procedure similar to that described in Example 2 sub-part d. to give the aldehyde (0.6 g); MS: m/z=378(M+1); NMR(CDCl$_3$): 3.98 and 3.2 (two peaks,3), 4.03 (m,2), 4.61 (dd,1, J=21, 3.5), 6.0 (d,1 J=2), 6.73–7.75 (m,5), 9.66 and 9.74 (two peaks,1).

EXAMPLE 31

3-[1-(3,4-Dichlorophenyl)-3-(4-acetamido-4-phenylpiperidino)propyl]-7-hydroxy-2-methyl-2,3-dihydroisoindol-1-one hydrochloride 3-(3,4-Dichlorophenyl)-3-(4-hydroxy-2-methyl-3-oxo-2,3-dihydro-1H-isoindol-1-yl)propionaldehyde (0.2.0 g) was coupled to 4-acetamido-4-phenylpiperidine (0.14 g) by a method similar to that described in Example 8. The reaction product was purified by chromatography and converted to the corresponding hydrochloride salt as described in the Example 8 to afford the title compound (0.27 g); mp 185–205° C.; MS: m/z=566(M+1); NMR(CD$_3$SOCD$_3$): 2.88 (m,1), 2.96 (s,3), 4.79 (d,1, J=3.5), 6.86 (m,2), 7.09 (d,$_1$, J=1.8), 7.20–7.47 (m,8). Analysis for C$_{31}$H$_{33}$Cl$_2$N$_3$O$_2$.1.0 HCl.1.5 H$_2$O: Calculated: C, 59.10; H, 5.91, N, 6.67; Found: C, 59.51; H, 5.63; N, 6.23.

The intermediate 3-(3,4-dichlorophenyl)-3-(4-hydroxy-2-methyl-3-oxo-2,3-dihydro-1H-isoindol-1-yl)propionaldehyde was synthesized as described below.

a. 3-[1-(3,4-Dichlorophenyl)but-3-enyl]-7-hydroxy-2-methyl-2,3-dihydroisoindol-1-one. A solution of 3-[1-(3,4-dichlorophenyl)-but-3-enyl]-7-methoxy-2-methyl-2,3-dihydroisoindol-1-one (1.8 g) in dichloromethane (25 mL) was cooled to 0° C. and treated with a 1.0 M solution (16.7 mL) of boron tribromide in dichloromethane and stirred for 10 minutes. The reaction mixture was heated to reflux for 18 hours, cooled to the room temperature and diluted (water). The mixture was extracted with dichloromethane, and the dichloromethane was washed (brine) dried and evaporated. Purification by chromatography, with dichloromethane:isopropanol (60:1) gave the hydroxy compound (1.44 g); MS: m/z=362(M+1); NMR: 1.76 (m,3), 2.75 (m,1), 4.66 (m,2), 5.74 (m,1), 6.55–7.48 (m,6).

b. 3-(3,4-Dichlorophenyl)-3-(4-hydroxy-2-methyl-3-oxo-2,3-dihydro-1H-isoindol-1-yl)propionaldehyde. 3-[1-(3,4-Dichlorophenyl)-but-3-enyl]-2-methyl-2,3-dihydro-7-hydroxy-1-H-isoindol-1-one (1.38 g) was treated by a method similar to the one described in Example 2 sub-part d. to obtain the aldehyde (0.2 g); MS: m/z=364(M+1); NMR: 3.04 (s,3), 4.02 (m,1), 4.69 (d,1, J=3.7), 6.68 (dd,1, J=8.3, 2.2), 6.9 (d,1, J=8.25), 6.96 (d,1 J=2.18), 7.06 (d,1, J=7.5), 7.2 (m,1), 7.45 (m,1), 8.46 (s,1), 9.79 (s,1).

EXAMPLE 32

3-[1-(3,4-Dichlorophenyl)-3-(4-(2-oxopiperidino)piperidino)propyl]-7-hydroxy-2-methyl-2,3-dihydroisoindol-1-one hydrochloride 3-(3,4-Dichlorophenyl)-3-(4-hydroxy-2-methyl-3-oxo-2,3-dihydro-1H-isoindol-1-yl)propionaldehyde (0.31 g) was coupled to 4-(2-oxopiperidino)piperidine (0.156 g) by a method similar to that described in Example 8. The reaction product was purified by chromatography and converted to the corresponding hydrochloride salt as described in the Example 8 to afford the title compound (0.378 g); mp 230–240° C.; MS: m/z=530(M+1); NMR(CD$_3$SOCD$_3$): 1.69 (m,5), 3.36 (s,3), 3.6 (m,3), 4.55 (broad,1), 4.76 (d,1, J=3), 6.81 (m,2), 7.04 (d,1 J=1.7), 7.37 (m,3). Analysis for C$_{28}$H$_{33}$Cl$_2$N$_3$O$_3$.1.2 HCl.1.0 H$_2$O: Calculated: C, 56.73; H, 6.16, N, 7.09; Found: C, 56.71; H, 5.91; N, 7.06.

The intermediate 3-(3,4-dichlorophenyl)-3-(4-hydroxy-2-methyl-3-oxo-2,3-dihydro-1H-isoindol-1-yl)propionaldehyde was synthesized from 3-[1-(3,4-dichlorophenyl)but-3-enyl]-7-methoxy-2-methyl-2,3-dihydroisoindol-1-one (prepared at Example 28 sub-part c.) using a sequence similar to that described in Example 31 subparts a.–b.

The intermediate 4-(2-oxopiperidino)piperidine was prepared as described in International Patent Application Publication Number WO 94/10146 at Example 8.

EXAMPLE 33

3-[1-(3,4-Dichlorophenyl)-3-(4-(2-oxoperhydropyrimidine-1-yl)piperidino)propyl]-7-hydroxy-2-methyl-2,3-dihydroisoindol-1-one hydrochloride 3-(3,4-Dichlorophenyl)-3-(4-hydroxy-2-methyl-3-oxo-2,3-dihydro-1H-isoindol-1-yl)propionaldehyde (0.31 g) was coupled to 4-(2-oxoperhydropyrimidine-1-yl)piperidine (0.156 g) by a method similar to that described in Example 8. The reaction product was purified by chromatography and converted to the corresponding hydrochloride salt as described in the Example 8 to afford the title compound (0.378 g); mp 225–240° C.; MS: m/z=531(M+1); NMR (CD$_3$SOCD$_3$): 1.60 (m,2), 1.65 (m,2), 2.98 (s,3), 4.37 (broad,1), 4.76 (d,1, J=3.5), 6.82 (m,2), 7.37 (m,4). Analysis for C$_{27}$H$_{32}$Cl$_2$N$_4$O$_3$.1.2 HCl.1.0 H$_2$O: Calculated: C, 54.66; H, 5.98, N, 9.44; Found: C, 54.70; H, 5.76; N, 9.15.

EXAMPLE 34

3-[1-(3,4-Dichlorophenyl)-3-(4-(2-oxoperhydropyrimidine-1-yl)piperidino)propyl]-7-isopropoxy-2-methyl-2,3-dihydroisoindol-1-one hydrochloride 3-(3,4-Dichlorophenyl)-3-(4-isopropoxy-2-methyl-3-oxo-2,3-dihydro-1H-isoindol-1-yl)propionaldehyde (0.15 g) was coupled to 4-(2-oxoperhydropyrimidine-1-yl)piperidine (0.068 g) by a method similar to that described in Example 8. The reaction product was not purified by chromatography but converted to the corresponding hydrochloride salt as described in the Example 8 to afford the title compound (0.08 g); mp 180–200° C. (d); MS: m/z=573(M+1); NMR: 1.14 (m,6), 1.77 (broad,4), 2.17 (m,2), 2.98 (s,3), 4.32 (m,1), 4.74 (m,1), 6.76–7.02 (m,3), 7.34–7.55 (m,3). Analysis for C$_{30}$H$_{38}$Cl$_2$N$_4$O$_3$.1.0 HCl.2.0 H$_2$O: Calculated: C, 55.77; H, 6.71, N, 8.67; Found: C, 55.91; H, 6.45; N, 8.44.

The intermediate 3-(3,4-dichlorophenyl)-3-(4-isopropoxy-2-methyl-3-oxo-2,3-dihydro-1H-isoindol-1-yl) propionaldehyde was synthesized as described below.

a. 3-[1-(3,4-Dichlorophenyl)but-3-enyl]-7-isopropoxy-3-methyl-2,3-dihydroisoindol-1-one. 3-[1-(3,4-dichlorophenyl)but-3-enyl]-7-hydroxy-3-methyl-2,3-dihydroisoindol-1-one (0.3 g), prepared as described in Example 31, was treated as described in Example 42 sub-part a. to afford the crude product. Chromatography, with hexane:isopropanol (2:1) gave the isopropyl ether (0.225 g): MS: m/z=404; NMR: 1.34 (m,6), 2.7 (t, J=7.8, 2) 3.04 (s,3), 3.37 (m,l), 4.6 (m,2), 5.09 (m,2), 5.71 (m,1), 7.01 (m,6).

b. 3-(3,4-Dichlorophenyl)-3-(4-isopropoxy-2-methyl-3-oxo-2,3-dihydro-1H-isoindol-1-yl)propionaldehyde. 3-[1-(3,4-Dichlorophenyl)but-3-enyl]-7-isopropoxy-3-methyl-2,3-dihydroisoindol-1-one (0.22 g) was subjected to a procedure similar to the one described in Example 2 sub-part d. Chromatography, gave the aldehyde (0.16 g); MS: m/z=406(M+1); NMR: 1.33 (m,6), 2.97 (s,3), 4.0 (m,1), 4.54 (m,2), 7.06 (m,6), 9.74 (s,1).

EXAMPLE 35

3-[1-(3,4-Dichlorophenyl)-3-(4-(2-oxoperhydropyrimidine-1-yl)piperidino)propyl]-5-isopropoxy-2-methyl-2,3-dihydroisoindol-1-one hydrochloride 3-(3,4-Dichlorophenyl)-3-(6-isopropoxy-2-methyl-3-oxo-2,3-dihydro-1H-isoindol-1-yl)propionaldehyde (0.50 g) was coupled to 4-(2-oxoperhydropyrimidine-1-yl)piperidine (0.225 g) by a method similar to that described in Example 8. The reaction product was not purified by chromatography but converted to the corresponding hydrochloride salt as described in the Example 8 to afford the title compound (0.567 g); mp 160–170° C. (d); MS: m/z=573(M+1); NMR (CD$_3$SOCD$_3$): 1.38 (m, 6), 1.83 (broad,5), 3.29 (s,3), 4.82 (m,1), 6.74–6.97 (m,2), 7.18–7.64 (m,4). Analysis for C$_{30}$H$_{38}$Cl$_2$N$_4$O$_3$.1.0 HCl.1.5 H$_2$O: Calculated: C, 56.56; H, 6.64, N, 8.79; Found: C, 56.49; H, 6.40; N, 8.78.

The intermediate 3-(3,4-dichlorophenyl)-3-(6-isopropoxy-2-methyl-3-oxo-2,3-dihydro-1H-isoindol-1-yl) propionaldehyde was prpeared from 3-[1-(3,4-dichlorophenyl)but-3-enyl]-5-methoxy-3-methyl-2,3-dihydro-1H-isoindol-1-one (described at Example 30 sub-part c.) by treating the ether as described in Example 31 sub-part a. to give the corresponding alcohol, followed by a sequence similar to that described in Example 42 sub-parts a.–b.

EXAMPLE 36

3-[1-(3,4-Dichlorophenyl)-3-(4-hydroxy-4-phenylpiperidino)propyl]-5-hydroxy-2-methyl-2,3-dihydrisoindol-1-one hydrochloride 3-(3,4-Dichlorophenyl)-3-(6-hydroxy-2-methyl-3-oxo-2,3-dihydro-1H-isoindol-1-yl)propionaldehyde (1.0 g) was coupled to 4-acetamido-4-phenylpiperidine (0.7 g) by a method similar to that described in Example 8. The reaction product was purified by chromatography and converted to the corresponding hydrochloride salt as described in Example 8 to afford the title compound (0.94 g); mp 203–223° C.; MS: m/z=566(M+1); NMR(CD$_3$SOCD$_3$): 2.98 (s,3), 3.54 (m,1), 4.75 (m,1), 6.90 (m,2), 7.10 (d,1, J=1.8), 7.22–7.4 (m,8).

The intermediate 3-(3,4-dichlorophenyl)-3-(6-hydroxy-2-methyl-3-oxo-2,3-dihydro-1H-isoindol-1 -yl) propionaldehyde was synthesized from 3-[1-(3,4-dichlorophenyl)but-3-enyl]-5-methoxy-2-methyl-2,3-dihyddroisoindol-1-one (described Example 30 sub-part c.) using a sequence similar to that described in Example 31 sub-parts a.–b.

EXAMPLE 37

3-[1-Methyl-1-(3,4-dichlorophenyl)-3-(4-acetamido-4-phenylpiperidino)propyl]-2-methyl-2, 3-dihydroisoindol-1-one hydrochloride 3-Methyl-3-(3,4-dichlorophenyl)-3-(2-methyl-3-oxo-2,3-dihydro-1H-isoindol-1-yl)propionaldehyde (isomer A described below) (0.3 g) was coupled to 4-acetamido-4-phenylpiperidine (0.25 g) by a method similar to that described in Example 8. The reaction product was purified by chromatography and converted to the corresponding hydrochloride salt as described in the Example 8 to afford the title compound (0.354 g); mp 195–225° C.; MS: m/z= 564(M+1); NMR(CDCl$_3$): 1.0 (s,3), 1.91 (s,1), 2.50 (s,3), 2.98 (m,4), 3.37 (m,2), 7.22–7.72 (m,10), 7.79 (s,1), 8.13 (s,1). Analysis for C$_{32}$H$_{35}$Cl$_2$N$_3$O$_2$.1.0 HCl.2.0 H$_2$O: Calculated: C, 60.33; H, 6.33, N, 6.59; Found: C, 60.09; H, 5.97; N, 6.28.

The intermediate 3-methyl-3-(3,4-dichlorophenyl)-3-(2-methyl-3-oxo-2,3-dihydro-1H-isoindol-1-yl) propionaldehyde was synthesized as described below.

a. 3-[1-Methyl-1-(3,4-dichlorophenyl)but-3-enyl]-3-hydroxy-2-methyl-2,3-dihydroisoindol-1-one. Using a procedure similar to that used for Example 28 sub-part b. but substituting N-methylbenzamide for 2-methoxy-N-methylbenzamide and substituting 2-methyl-2-(3,4-dichloro-pheny)pent-4-enoic acid ethyl ester for 2-(3,4-dichloropheny)pent-4-enoic acid ethyl ester the alcohol was prepared; MS: m/z=376(M+1); NMR (CDCl$_3$): 1.98 and 1.07 (two peaks,3), 2.2:2 and 2.77 (two peaks,3), 2.38 (m,1), 3.0 and 3.4 (m,1), 4.9 (m,2), 5.2 (m,1), 6.12 (d, J=7.6, 1), 7.17–7.58 (m,7).

b. 3-[1-Methyl-1-(3,4-dichlorophenyl)but-3-enyl]-2-methyl-2,3-dihydro-1-H-isoindol-1-one. 3-[1-Methyl-1-(3,4-dichlorophenyl)-but-3-enyl]-3-hydroxy-2-methyl-2,3-dihydroisoindol-1-one was treated in a manner similar to that described in Example 28 sub-part c. to afford the desired product; MS: m/z=360(M+1); NMR(CDCl$_3$): 0.95 and 1.00 (two peaks,3), 2.58 and 3.24 (two peaks,3), 4.98 (m,2), 5.3 (m,$_1$), 6.05 (d,1, J=7.6), 7.17–7.5 (m,5), 7.85 (m,2).

c. 3-Methyl-3-(3,4-dichlorophenyl)-3-(2-methyl-3-oxo-2,3-dihydro-1H-isoindol-1-yl)propionaldehyde. 3-[1-Methyl-1-(3,4-dichlorophenyl)but-3-enyl]-2-methyl-2,3-dihydro-1-H-isoindol-1-one (1.13 g) was treated as described in Example 2 sub-part d. Chromatography gave two isomers of the aldehyde; Isomer A: MS: m/z=362(M+1); NMR(CDCl$_3$): 1.37 (s,3), 2.72 (s,3), 2.8 (m,1), 3.0 (m,1), 4.77 (s,1), 6.97 (m,1), 7.28 (m,1), 7.43–7.55 (m,4), 7.86 (m,1), 9.47 (t,1 J=2.3); Isomer B: MS: m/z=362(M+1); NMR(CDCl$_3$): 1.34 (s,3), 2.71 (dd,1, J=16, 2), 3.0 (s,3), 3.16 (dd,1, J=16, 1.8), 4.73 (s,1), 6.36 (d,1, J=7.7), 7.24–7.56 (m,4),7.85 (dd,1, J=8.3, 0.86), 9.47 (t,1, J=2.3).

EXAMPLE 38

3-[1-Methyl-1-(3,4-Dichlorophenyl)-3-(4-acetamido-4-phenylpiperidino)propyl]-2-methyl-2,3-dihydroisoindol-1-one hydrochloride (stereo chemistry)

3-Methyl-3-(3,4-dichlorophenyl)-3-(2-methyl-3-oxo-2,3-dihydro-1H-isoindol-1-yl)propionaldehyde (isomer B prepared as described in Example 37 sub-part c. above) (0.52 g) was coupled to 4-acetamido-4-phenylpiperidine (0.36 g) by a method similar to that described in Example 8. The reaction product was purified by chromatography and converted to the corresponding hydrochloride salt as described in the Example 8 to afford the title compound (0.55 g); mp 200–228° C.; MS: m/z=564(M+1); NMR: 1.0 (s,3), 1.99 (s,1), 2.36 (m,2), 2.7 (m,2), 3.26 (s,3), 4.65 (s,1), 5.94 (d,1, J=7.7), 7.18–7.41 (m,9), 7.54 (d,1 J=8.3), 7.77 (d, J=7.5). Analysis for C$_{32}$H$_{35}$Cl$_2$N$_3$O$_2$.1.0 HCl.1.0 H$_2$O Calculated: C, 62.09; H, 6.18, N, 6.79; Found: C, 62.32; H, 6.24; N, 6.66.

EXAMPLE 39

3-[1-(3,4-Dichlorophenyl)-3-(4-(2-oxoperhydropyrimidine-1-yl)piperidino)propyl]-6-hydroxy-2-methyl-2,3-dihydroisoindol-1-one hydrochloride 3-(3,4-Dichlorophenyl)-3-(5-hydroxy-2-methyl-3-oxo-2,3-dihydro-1H-isoindol-1-yl)propionaldehyde (0.23 g) was coupled to 4-(2-oxoperhydropyrimidine-1-yl)piperidine (0.136 g) by a method similar to that described in Example 8. The reaction product was not purified by chromatography but converted to the corresponding hydrochloride salt as described in the Example 8 to afford the title compound (0.220 g); mp 200–210° C.; MS: m/z=531(M+1); NMR: 1.0 (s,3), 1.99 (s,1), 2.36 (m,2), 2.7 (m,2), 3.26 (s,3),4.65 (s,1), 5.94 (d,1, J=7.7), 7.18–7.41 (m,9), 7.54 (d,1, J=8.31), 7.77 (d, J=7.5). Analysis for CH$_{32}$H$_{35}$Cl$_2$N$_3$O$_3$.1.0 HCl.1.5 H$_2$O: Calculated: C, 54.51; H, 6.09, N, 9.41; Found: C, 54.82 ; H, 5.78 ; N, 9.41.

The intermediate 3-(3,4-dichlorophenyl)-3-(5-hydroxy-2-methyl-3-oxo-2,3-dihydro-1H-isoindol-1-yl) propionaldehyde was synthesized as described below.

a. 3-[1-(3,4-Dichlorophenyl)but-3-enyl]-6-hydroxy-3-methyl-2,3-dihydroisoindol-1-one. 3-[1-(3,4-dichlorophenyl)but-3-enyl]-6-methoxy-3-methyl-2,3-dihydroisoindol-1-one (0.25 g, prepared as described in Example 16 sub-parts a.–c.) was subjected to conditions similar to that described in Example 31 sub-part a. The material was crystallized from toluene to obtain the desired alcohol (0.1 g); MS: m/z=362(M+1); NMR (CD$_3$SOCD$_3$): 2.69 (m,2), 3.01 (s,3), 3.62 (m,1), 4.7 (d,$_1$, J=3.5), 5.06 (m,2), 5.73 (m,1), 7.15 (m,6), 9.8 (s,1).

b. 3-(3,4-Dichlorophenyl)-3-(5-hydroxy-2-methyl-3-oxo-2,3-dihydro-1H-isoindol-1-yl)propionaldehyde. 3-[1-(3,4-Dichlorophenyl)-but-3-enyl]-6-hydroxy-3-methyl-2,3-dihydroisoindol-1-one (0.6 g) was subjected to a procedure similar to to the one described in Example 2 sub-patr d. Chromatography gave the aldehyde (0.4 g); obtained; MS: m/z=364 (M+1); NMR: 2.99 (s,3), 3.14 (m,2), 4.06 (broad, 1), 4.7 (s,1), 7.22 (m,6), 9.63 (s,1), 9.81 (s,1).

EXAMPLE 40

3-[1-(3,4-Dichlorophenyl)-3-(4-(2-oxoperhydropyrimidine-1-yl)piperidino)propyl]-6-(dimethylamino)-2-methyl-2,3-dihydro-isoindol-1-one hydrochloride 3-(3,4-Dichlorophenyl)-3-[5-(dimethylamino)-2-methyl-3-oxo-2,3-dihydro-1H-isoindol-1-yl]propionaldehyde (0.2 g) was coupled to 4-(2-oxoperhydropyrimidine-1-yl) piperidine (0.093 g) by a method similar to that described in Example 8. The reaction product was not purified by chromatography but converted to the corresponding hydrochloride salt as described in the Example 8 to afford the title compound (0.085 g); MS: m/z=558(M+1); NMR: 1.60 (broad, 3), 1.78 (broad,3), 2.14 (broad,3), 2.73 (broad,3), 3.02 (m,3), 3.57 (m,3), 4.37 (broad,1), 4.74 (broad,1), 7.27 (m,6). Analysis for C$_{29}$H$_{37}$Cl$_2$N$_5$O$_2$.2.0 HCl.2.0 H$_2$O: Calculated: C, 52.18; H, 6.49, N, 10.49; Found: C, 51.94; H, 6.71; N, 10.27.

The intermediate 3-(3,4-dichlorophenyl)-3-[5-(dimethylamino)-2-methyl-3-oxo-2,3-dihydro-1H-isoindol-1-yl]propionaldehyde was synthesized as described below.

a. N-Methyl-3-(dimethylamino)benzamide. 3-(dimethylamino)-benzoic acid (25 g) was treated as described in Example 16.a. Chromatography, with ethyl acetate as the eluent, gave the amide (13 g); MS: m/z=179 (M+1); NMR: 2.97 (d,3, J=6.2), 6.39 (broad,1), 6.98 (m,4).

b. 3-[1-(3,4-Dichlorophenyl)but-3-enyl]-6-(dimethylamino)-3-hydroxy-2-methyl-2,3-dihydroisoindol-1-one. Tetrahydrofuran (80 mL) containing tetramethylethylenediamine (6.09 g) at −74° C. was treated with 40.4 mL of 1.3 M solution of sec-butyllithium so the temperature of the reaction mixture remained below −74° C. After the completion of the addition, a solution of N-methyl-3-(dimethylamino)benzamide (4.46 g) in tetrahydrofuran (60 mL) was added dropwise to maintain the temperature of the reaction mixture below −68° C. After the addition was complete, the reaction mixture was stirred at −76° C. for 1.5 hours and treated with a solution of 2-(3,4-dichlorophenyl)pent-4-enoic acid ethyl ester (6.8 g) in tetrahydrofuran (10 mL). After stirring at −76° C for 10 minutes the reaction mixture was allowed to warm to the ambient temperature and stirred for 18 hours. The reaction mixture was concentrated under reduced pressure to half the volume, treated with 10% aqueous hydrochloric acid until the pH was 5, and diluted with ethyl acetate. The aqueous layer was extracted with ethyl acetate, and the organic layers were washed (water). The organics were dried (anhydrous potassium carbonate) and evaporated. The resulting material was purified by chromatography, hexane:isopropanol (9:1) as the eluent to give the alcohol (1.04 g); MS: m/z=405(M+1); NMR: 2.00 (m,2), 2.77 (m,1), 3.48 (broad,1), 4.88 (m,4), 5.47 (m,2), 6.91 (m,12).

c. 3-[1-(3,4-Dichlorophenyl)but-3-enyl]-6-(dimethylamino)-2-methyl-2,3-dihydroisoindol-1-one. 3-[1-(3,4-Dichlorophenyl)but-3-enyl]-6-(dimethylamino)-3-hydroxy-2-methyl-2,3-dihydroisoindol-1-one (1.0 g) was treated using a procedure similar to the one described in Example 28 sub-part c. to afford the des-hydroxy compound (0.3 g); MS: m/z=389(M+1); NMR: 2.68 (t,2, J=8.2), 3.04 (m,9), 3.32 (m,1), 4.57 (d,1, J=3.9), 5.08 (m,2), 5.72 (m,1), 6.98 (m,6).

d. 3-(3,4-Dichlorophenyl)-3-[5-(dimethylamino)-2-methyl-3-oxo-2,3-dihydro-1H-isoindol-1-yl]propionaldehyde. 3-[1-(3,4-Dichlorophenyl)but-3-enyl]-6-(dimethylamino)-2-methyl-2,3-dihydroisoindol-1-one (0.3 g) was subjected to a procedure similar to the one described in Example 2 sub-part d. Chromatography, gave the aldehyde (0.2 g); MS: m/z=391(M+1); NMR: 2.88 (m,11), 3.89 (m,1), 4.45 (d,1, J=3.3), 6.8 (m,6), 9.61 (s,1).

EXAMPLE 41

3-[1-(3,4-Dichlorophenyl)-3-(4-(2-oxoperhydropyrimidine-1-yl)piperidino)propyl]-2-methyl-6-methylsulfonyl-2,3-dihydroisoindol-1-one hydrochloride 3-(3,4-Dichlorophenyl)-3-(2-methyl-3-oxo-5-methylsulfonyl-2,3-dihydro-1H-isoindol-1-yl)propionaldehyde (0.35 g) was coupled to 4-(2-oxoperhydropyrimidine-1-yl)piperidine (0.15 g) by a method similar to that described in Example 8. The reaction product was not purified by chromatography but converted to the corresponding hydrochloride salt as described in the Example 8 to give the title compound (0.1 g); MS: m/z= 593(M+1); NMR: 1.16 (m,5), 2.21 (m,5), 3.65 (m,1), 4.25 (m,1), 5.01 (d,1, J=3.9), 6.73 (m,2), 7.21 (m,1), 8.18 (m,3). Analysis for $C_{28}H_{34}Cl_2N_4O_{24}S.2.0\ H_2O$: Calculated C, 53.14; H, 6.08, N, 8.89; Found: C, 53.58; H, 5.73; N, 8.56.

The intermediate 3-(3,4-Dichlorophenyl)-3-(2-methyl-3-oxo-5-methylsulfonyl-2,3-dihydro-1H-isoindol-1-yl)propionaldehyde was synthesized as described below.

a. N-methyl-3-nitrobenzamide. Using a method similar to that described in Example 16 sub-part a. 3-nitrobenzoic acid (30 g) was converted to the amide (18 g); MS: m/z=259 (M+1); NMR: 3.06 (d,3, J=4.9), 6.07 (broad,1), 7.79 (d,1 J=8.7), 8.11 (m,1), 8.36 (d,1 J=2.7).

b. N-methyl-3-aminobenzamide. A solution of N-methyl-3-nitrobenzamide (20 g) in acetic acid (500 mL) was treated with Raney Nickel catalyst (50 mL of slurry in water) and hydrogenated at 15 psi hydrogen pressure for 1.75 hour. At the end of this period the reaction mixture was filtered to remove the catalyst, evaporated and the residue was dissolved in dichloromethane. The dichloromethane layer was extracted with sodium bicarbonate solution, the aqueous layer was basified with potassium carbonate solution and extracted with two portions of ethyl acetate. The combined organic layers were dried over anhydrous sodium sulfate, and evaporated to obtain a solid, which was crystallized from ethyl acetate to give the amine (12.7 g): mp 115–116° C.; MS: m/z=229(M+1); NMR: 2.97 (d,3 J=9.7), 3.84 (s,2), 6.12 (broad,1), 6.55 (m,1), 6.84 (d,1, J=2.9), 7.27 (d,1, J=8.6).

c. N-methyl-3-methylthiobenzamide. To water (50 mL) containing concentrated hydrochloric acid (12.7 mL) was added N-methyl-3-aminobenzamide (12.7 g), the resulting suspension was stirred for 15 minutes and treated with sodium nitrite (3/75 g) in water (75 mL). The temperature of the reaction mixture was maintained below 5° C. and added to a solution of sodium thiomethoxide (8.93 g) in water (100 mL) kept at 5° C. Upon the addition was complete the reaction mixture was stirred at 0° C. for 1 hour and then allowed to warm to 15° C. The resulting precipitate was filtered and washed (water).

Upon drying in vacuum, the solid was crystallized from ethyl acetate to afford the desired N-methyl-3-methylthiobenzamide (10.2 g); MS: m/z=260(M+1); NMR: 2.47 (s,3), 3.00 (d,3, J=3), 6.06 (broad,1), 7.19 (m,3).

d. 3-[1-(3,4-Dichlorophenyl)but-3-enyl]-3-hydroxy-6-methylthio-2-methyl-2,3-dihydroisoindol-1-one. A solution of N-methyl-3-methylthiobenzamide (6.0 g) in tetrahydrofuran (150 mL) at −74° C. was treated with 19.3 mL of 2.5 M n-butyllithium. The reaction mixture was stirred at −76° C. for 30 minutes and treated dropwise with a solution of 2-(3,4-dichlorophenyl)pent-4-enoic acid ethyl ester (6.25 g) in tetrahydrofuran (10 mL) to maintain the temperature of the reaction mixture below −73° C. The reaction mixture was stirred at −76° C. for 35 minutes, and then allowed to warm to 0° C. The reaction mixture was then treated with 10% aqueous hydrochloric acid and diluted with ethyl acetate. The aqueous layer was extracted with ethyl acetate and the organic layers were washed (sodium bicarbonate), dryied (anhydrous sodium sulfate) and evaporated. Crystallization from ethyl acetate gave the alcohol; MS: m/z=405 (M+1); NMR(CDCl$_3$): 2.51 (m,5), 2.75 (s,3), 3.14 (m,1), 3.27 (m,1), 3.71 (s,1),4.89 (m,2), 6.3 (m,1), 6.6 (s,1), 7.32 (m,4).

e. 3-[1-(3,4-Dichlorophenyl)but-3-enyl]-3-methyl-6-methylthio-2,3-dihydroisoindol-1-one. 3-[1-(3,4-Dichlorophenyl)-but-3-enyl]-3-hydroxy-6-methylthio-2-methyl-2,3-dihydroisoindol-1-one (1.3 g) was treated using a procedure similar to the one described in Example 16 sub-part c. to afford the des-hydroxy compound (0.5 g); MS: m/z=392(M+1); NMR(CDCl$_3$): 2.51 (s,3), 2.7(t, J=7.5, 2), 3.09 (s,3), 3.4 (m,1), 4.63 (d,1, J=3.8), 5.1 (m,2), 5.71 (m,1), 7.02 (m,6).

f. 3-(3,4-Dichlorophenyl)-3-(2-methyl-3-oxo-5-methylsulfonyl-2,3-dihydro-1H-isoindol-1-yl)propionaldehyde. 3-[1-(3,4-Dichlorophenyl)but-3-enyl]-3-methyl-6-methylthio-2,3-dihydro-isoindol-1-one (0.5 g) was treated under a procedure similar to the one described in Example 2 sub-part d., except that 0.98 g of sodium periodate was used. Chromatography, gave the desired aldehyde (0.4 g); MS: m/z=426(M+1); NMR: 1.58 (s,1), 3.08 (m,8), 4.12 (m,1), 4.80 (d,1, J=3.5), 6.76 (m,2), 7.25 (m,1), 7.78 (m,1), 8.25 (m,2), 9.82 (s,1).

EXAMPLE 42

3-[1-(3,4-Dichlorophenyl)-3-(4-(2-oxoperhydropyrimidine-1-yl)piperidino)propyl]-6-isopropoxy-2-methyl-2,3-dihydroisoindol-1-one hydrochloride 3-(3,4-Dichlorophenyl)-3-(5-isopropoxy-2-methyl-3-oxo-2,3-dihydro-1H-isoindol-1-yl)propionaldehyde (0.3 g)

was coupled to 4-(2-oxoperhydropyrimidine-1-yl)piperidine (0.135 g) by a method similar to that described in Example 8. The reaction product was not purified by chromatography but converted to the corresponding hydrochloride salt as described in the Example 8 to afford the title compound (0.25 g); mp 192–200° C.; MS: m/z=573(M+1); NMR (CD$_3$SOCD$_3$): 1.24 (d,6, J=5.9), 1.77 (broad,2), 2.19 (m,2), 2.5 (m,2), 2.73 (broad,1l), 3.58 (m,3), 4.39 (m,1), 4.74 (m,2), 7.06 (m,5), 7.79 (d,1, J=8.4). Analysis for C$_{30}$H$_{38}$Cl$_2$N$_4$O$_3$.2.0 HCl: Calculated: C, 55.74; H, 6.24, N, 8.67; Found: C, 56.11; H, 6.22; N, 8.60.

The intermediate 3-(3,4-Dichlorophenyl)-3-(5-isopropoxy-2-methyl-3-oxo-2,3-dihydro-1H-isoindol-1-yl) propionaldehyde was synthesized as described below.

a. 3-[1-(3,4-dichlorophenyl)but-3-enyl]-6-isopropoxy-3-methyl-2,3-dihydroisoindol-1-one. 3-[1-(3,4-Dichlorophenyl)but-3-enyl]-6-hydroxy-3-methyl-2,3-dihydroisoindol-1-one (0.4 g) in tetrahydrofuran was treated with sodium hydride (0.05 g) and the resulting solution was treated with 2-iodopropane (0.8 g). Upon heating to reflux for 24 hours, the reaction mixture was diluted (water), extracted twice with ethyl acetate and the organic layer was washed (water and brine), dried and evaporated. Chromatography, with hexane:isopropanol (9:1) as the eluent, gave the ether, contaminated with the starting material. The material was dissolved in ethyl acetate and washed (1N sodium hydroxide solution, water and brine), dried, and evaporated to give the ether (0.35 g); MS: m/z=404; NMR (CDCl$_3$): 1.32 (d,6, J=6.1), 2.7 (t,2, J=7.8) 3.09 (s,3), 3.37 (m,1), 4.6 (m,2), 5.09 (m,2) (m,1), 7.01 (m,6).

b. 3-(3,4-Dichlorophenyl)-3-(5-isopropoxy-2-methyl-3-oxo-2,3-dihydro-1H-isoindol-1-yl)propionaldehyde. 3-[1-(3,4-dichlorophenyl)but-3-enyl]-6-isopropoxy-3-methyl-2,3-dihydroisoindol-1-one (0.55 g) was subjected to a procedure similar to the one described in Example 2 sub-part d. Chromatography gave the aldehyde (0.3 g); MS: m/z=406(M+1); NMR(CDCl$_3$): 1.33 (s,1), 3.01 (m,6), 4.0 (m,1), 4.60 (m,2), 7.06 (m,6), 9.74 (s,1).

EXAMPLE 43

3-[1-(3,4-Dichlorophenyl)-3-(4-(2-oxoperhydropyrimidine-1-yl)piperidino)propyl]-6-ethoxy-2-methyl-2,3-dihydroisoindol-1-one hydrochloride 3-(3,4-Dichlorophenyl)-3-(5-ethoxy-2-methyl-3-oxo-2,3-dihydro-1H-isoindol-1-yl)propionaldehyde (0.3 g) was coupled to 4-(2-oxoperhydropyrimidine-1-yl)piperidine (0.135 g) by a method similar to that described in Example 8. The reaction product was not purified by chromatography but converted to the corresponding hydrochloride salt as described in the Example 8 to afford the title compound (0.28 g); mp 190–200° C.; MS: m/z=559(M+1); NMR (CDCl$_3$): 1.33 (t,6, J=6.9), 1.71 (m,4), 2.20 (m,2), 2.5 (m,2), 2.74 (broad,1), 3.52 (m,3), 4.04 (m,2), 4.31 (m,1), 4.76 (m,2), 7.05 (m,5), 7.81 (d,1, J=8.41). Analysis for C$_{29}$H$_{36}$Cl$_2$N$_4$O$_3$.2.0 HCl.0.5 H$_2$O: Calculated: C, 54.30; H, 6.13, N, 8.73; Found: C, 54.02; H, 6.00; N, 8.47.

The intermediate 3-(3,4-Dichlorophenyl)-3-(5-ethoxy-2-methyl-3-oxo-2,3-dihydro-1H-isoindol-1-yl) propionaldehyde was synthesized as described below.

a. 3-[1-(3,4-Dichlorophenyl)but-3-enyl]-6-ethoxy-3-methyl-2,3-dihydroisoindol-1-one. 13-[1-(3,4-Dichlorophenyl)but-3-enyl]-6-hydroxy-3-methyl-2,3-dihydroisoindol-1-one (0.4 g) in tetrahydrofuran (5 mL) was treated with a suspension of sodium hydride (0.05 g) in tetrahydrofuran (10 mL), refluxed for 30 minutes and then treated with ethyl iodide (0.2 g) in tetrahydrofuran (5 mL). Upon heating to reflux for 2 hours, additional amounts of ethyl iodide (0.2 g) were added and the reflux was continued for an additional 3 hours. The reaction mixture was diluted (water), extracted twice with ethyl acetate and the organic layers were washed (water and brine), dried and evaporated. Chromatography, with hexane:isopropanol (9:1) as the eluent, gave the ether (0.24 g); MS: m/z=390; NMR: 1.39 (t,3, J=7), 2.81 (m,2), 3.09 (s,3), 3.14 (s,3), 3.58 (m,1), 4.05 (q,2, J=7), 4.77 (d,1, J=3.9), 4.98 (m,2), 5.76 (m,1), 6.92 (m,5), 7.70 (d,1, J=8.4).

b. 3-(3,4-Dichlorophenyl)-3-(5-ethoxy-2-methyl-3-oxo-2,3-dihydro-1H-isoindol-1-yl)propionaldehyde. 3-[1-(3,4-Dichlorophenyl)-but-3-enyl]-6-ethoxy-3-methyl-2,3-dihydroisoindol-1-one (0.389 g) was subjected to a procedure similar to the one described in Example 2 sub-part d. Chromatography, gave the aldehyde (0.3 g); MS: m/z=392(M+1); NMR: 1.43 (t,3, J=4.8), 3.05 (m,5), 4.02 (m,3), 4.61 (d,1, J=3.5), 7.05 (m,6), 9.75 (s,1).

EXAMPLE 44

3-[1-(3,4-Dichlorophenyl)-3-(4-(2-oxoperhydropyrimidine-1-yl)piperidino)propyl]-6-acetoxy-2-methyl-2,3-dihydroisoindol-1-one hydrochloride 3-(3,4-Dichlorophenyl)-3-(5-acetoxy-2-methyl-3-oxo-2,3-dihydro-1H-isoindol-1-yl)propionaldehyde (0.35 g) was coupled to 4-(2-oxoperhydropyrimidine-1-yl)piperidine (0.135 g) by a method similar to that described in Example 8. The reaction product was not purified by chromatography but converted to the corresponding hydrochloride salt as described in the Example 8 to afford the title compound (0.25 g); mp 190–200° C.; MS: m/z=573(M+1); NMR (CD$_3$SOCD$_3$): 1.63 (broad,6), 2.14 (broad,3), 2.27 (s,3), 2.7 (broad,1), 3.6 (m,3), 4.22 (m,1), 4.85 (d,1, J=3.6), 7.09 (m,5), 7.95 (d,1 J=8.2). Analysis for C$_{29}$H$_{34}$Cl$_2$N$_4$O$_4$.2.0 HCl.1.0 H$_2$O: Calculated: C, 52.42; H, 5.76, N, 8.43; Found: C, 52.83; H, 5.58; N, 8.31.

The intermediate 3-(3,4-dichlorophenyl)-3-(5-acetoxy-2-methyl-3-oxo-2,3-dihydro-1H-isoindol-1-yl) propionaldehyde was synthesized as described below.

a. 3-[1-(3,4-Dichlorophenyl)but-3-enyl]-6-acetoxy-3-methyl-2,3-dihydroisoindol-1-one. 3-[1-(3,4-Dichlorophenyl)but-3-enyl]-6-hydroxy-3-methyl-2,3-dihydroisoindol-1-one (0.4 g) in tetrahydrofuran (5 mL) was treated with a suspension of sodium hydride (0.05 g) in tetrahydrofuran (10 mL), refluxed for 30 minutes and treated with acetyl chloride (0.13 mL) in tetrahydrofuran (5 mL). After stirring for 5 minutes at room temperature, the reaction mixture was diluted with sodium bicarbonate solution and extracted twice with ethyl acetate. The organic layers were washed (water and brine), dried, and evaporated to give the acetoxy compound (0.4 g); mp 155–157° C.; MS: m/z=404; NMR(CDC$_{13}$): 2.33 (s,3), 2.71 (t, J=7, 2), 3.1 (s,3), 3.42 (m,1), 4.66 (d,1, J=3.8), 5.11 (m,2), 5.72 (m,1), 7.08 (m,6).

b. 3-(3,4-Dichlorophenyl)-3-(5-acetoxy-2-methyl-3-oxo-2,3-dihydro-1H-isoindol-1-yl)propionaldehyde. 3-[1-(3,4-Dichlorophenyl)-but-3-enyl]-6-acetoxy-3-methyl-2,3-dihydroisoindol-1-one. (0.4 g) was subjected to a procedure similar to the one described in Example 2 sub-part d. Chromatography, gave the aldehyde (0.38 g); MS: m/z=406 (M+1); NMR: 2.32 (s,3), 3.06 (m,5), 4.04 (m,1), 4.62 (d,1, J=3.5), 7.1 (m,6), 9.71 (s,1).

EXAMPLE 45

3-[1-(3,4-Dichlorophenyl)-3-(4-(2-oxoperhydropyrimidine-1-yl)piperidino)propyl]-6-fluoro-2-methyl-2,3-dihydroisoindol-1-one hydrochloride 3-(3,4-Dichlorophenyl)-3-(5-fluoro-2-methyl-3-oxo-2,3-dihydro-1H-isoindol-1-yl)propionaldehyde (0.27 g) was coupled to 4-(2-oxoperhydropyrimidine-1-yl)piperidine (0.135 g) by a method similar to that described in Example 8. The reaction product was not purified by chromatography but converted to the corresponding hydrochloride salt as described in the Example 8 to afford the title compound (0.3 g); mp 180–205° C. (d); MS: m/z=533(M+1); NMR (CD$_3$SOCD$_3$): 1.73 (m,4), 2.17 (broad,2), 2.5 (broad,2), 2.74 (broad,1), 3.49 (m,5),3.69 (m,1), 4.36 (m,1), 4.86 (d,1, J=3.3), 6.75 (d,1, J=8.2) 7.07 (s,1), 7.35 (m,3), 7.92 (m,1). Analysis for C$_{27}$H$_{31}$Cl$_2$N$_4$O$_4$F.2.0 HCl: Calculated: C, 53.48; H, 5.49, N, 9.24; Found: C, 53.15; H, 5.53; N, 9.04.

The intermediate 3-(3,4-dichlorophenyl)-3-(5-fluoro-2-methyl-3-oxo-2,3-dihydro-1H-isoindol-1-yl) propionaldehyde was synthesized as described below.

a. 2-Bromo-5-fluorobenzoic acid. A suspension of 2-bromo-5-fluorotoluene (50 g) in water (1.2L) containing potassium permanganate (189 g) and sodium hydroxide (8.3 g) was refluxed for 6 hours, treated with celite, and filtered. The filtrate was extracted twice with ethyl acetate. The aqueous layer was filtered and acidified with concentrated hydrochloric acid and the resulting precipitate was collected to afford the acid (16.33 g): MS: m/z=219; NMR: 7.16 (m,2), 7.71 (m,2).

b. N-Methyl-2-bromo-5-fluorobenzamide. A method similar to that described in Example 16 sub-part a. was used to convert 2-bromo-5-fluorobenzoic acid (18.36 g) to the amide (14.36 g); mp 105–107° C.; MS: m/z=232(M+1); NMR: 2,99 (d,3, J=4.8), 6.25 (broad,1), 7.25 (m,3).

c. 3-[1-(3,4-Dichlorophenyl)but-3-enyl]-6-fluoro-3-hydroxy-2-methyl-2,3-dihydroisoindol-1-one. A solution of N-methyl-2-bromo-5-fluorobenzamide (6.0 g) in tetrahydrofuran (150 mL) at −74° C. was treated with 19.3 mL of 2.5 M n-butyllithium. The reaction mixture was stirred at −76° C. for 30 minutes. 2-(3,4-dichlorophenyl)-pent-4-enoic acid ethyl ester (6.25 g) in tetrahydrofuran (10 mL) was added dropwise to maintain the temperature of the reaction mixture below −73° C. The reaction mixture was stirred at −73° C. for 35 minutes, and then allowed to warm to 0° C. The reaction mixture was treated with 10% aqueous hydrochloric acid, and diluted with ethyl acetate. The aqueous layer was extracted with ethyl acetate and the organic layers were washed (sodium bicarbonate), dried (anhydrous sodium sulfate) and evaporated. Crystallization from ethyl acetate gave the alcohol; MS: m/z=364(M+1); NMR: 2.68 (t, J=7.1, 2), 3.01 (s,3), 3.38 (m,1), 4.62 (d, J=3.3, 1), 5.1 (m,2), 5.69 (m,1), 6.99 (m,6).

d. 3-[1-(3,4-Dichlorophenyl)but-3-enyl]-6-fluoro-3-methyl-2,3-dihydroisoindol-1-one. 3-[1-(3,4-Dichlorophenyl)but-3-enyl]-6-fluoro-3-hydroxy-2-methyl-2,3-dihydroisoindol-1-one (2.6 g) was treated using a procedure similar to the one described in Example 2 sub-part c., except that the reaction mixture was heated to reflux for 2 hours to afford the des-hydroxy compound (0.6 g); MS: m/z=364(M+1); NMR: 2.71 (t, J=7.4, 2) 3.05 (s,3), 3.4 (m,1), 4.65 (d,J=3.7), 5.1 (m,2), 5.72 (m,1), 6.52 (m,1), 6.81 (d,1, J=21), 7.42 (m,4).

e. 3-(3,4-Dichlorophenyl)-3-(5-fluoro-2-methyl-3-oxo-2,3-dihydro-1H-isoindol-1-yl)propionaldehyde. 3-[1-(3,4-Dichlorophenyl)-but-3-enyl]-6-fluoro-3-methyl-2,3-dihydroisoindol-1-one (0.5 g) was subjected, to a procedure similar to the one described in Example 2 sub-part d. Chromatography, gave the aldehyde (0.27 g); MS: m/z=366 (M+1); NMR: 3.04 (m,8), 3.99 (m,1), 4.61 (d,1, J=3.5), 7.02 (m,6), 9.69 (s,1).

EXAMPLE 46

3-[1-(3,4-Dichlorophenyl)-3-(4-(2-oxoperhydropyrimidine-1-yl)piperidino)propyl)-5-chloro-2-methyl-2,3-dihydroisoindol-1-one hydrochloride 3-(3,4-Dichlorophenyl)-3-(6-chloro-2-methyl-3-oxo-2,3-dihydro-1H-isoindol-1-yl)propionaldehyde (0.23 g) was coupled to 4-(2-oxoperhydropyrimidine-1-yl)piperidine (0.135 g) by a method similar to that described in Example 8. The reaction product was not purified by chromatography but converted to the corresponding hydrochloride salt as described in the Example 8 to afford the title compound (0.19 g); mp 220° C.; MS: m/z=549(M+1); NMR: 1.73 (m,4), 2.09 (m,2), 2.5 (broad,2), 2.44 (m,2), 2.75 (s,1), 3.07 (m,9), 3.56 (m,4), 4.88 (d,1, J=3), 6.83 (d,1, J=8), 7.08 (s,1), 7.49 (m,3), 8.04 (m,1). Analysis for C$_{27}$H$_{31}$Cl$_3$N$_4$O$_4$: Calculated: C, 52.87; H, 5.75, N, 9.13; Found: C, 53.27; H, 5.64; N, 8.85.

The intermediate 3-(3,4-Dichlorophenyl)-3-(6-chloro-2-methyl-3-oxo-2,3-dihydro-1H-isoindol-1-yl) propionaldehyde was synthesized as described below.

a. N-Methyl-4-chlorobenzamide. A method similar to that described in Example 16 sub-part a. was used to convert 2-bromo-5-fluorobenzoic acid (23.5 g) to the amide (15 g); mp 158–159° C.; MS: m/z=170(M+1); NMR: 2,98 (d,3, J=4.8), 6.49 (broad,1), 7.37 (d,2), 7.7 (d,2 J=4.8).

b. 3-[1-(3,4-Dichlorophenyl)but-3-enyl]-5-chloro-3-hydroxy-2-methyl-2,3-dihydroisoindol-1-one. A method similar to that described in Example 40 sub-part b. was used except that N-methy-4-chloro-benzamide was used instead of N-methyl-3-(dimethylamino)benzamide. Chromatography, with hexane:isopropanol (9:1) as the eluent, gave the alcohol; MS: m/z=396(M+1); NMR: 1.87 (m,1), 1.99 (m,1), 2.5 (m,1), 2.7 (s,3), 2.89 (s,3), 2.89 (m,1), 3.3 (m,2), 4.42 (broad,1), 4.92 (m,4), 5.42 (m,2), 7.0 (m,12).

c. 3-[1-(3,4-Dichlorophenyl)but-3-enyl]-5-chloro-2-methyl-2,3-dihydro-1H-isoindol-1-one. 3-(1-(3,4-Dichlorophenyl)but-3-enyl]-5-chloro-3-hydroxy-2-methyl-2,3-dihydroisoindol-1-one (2.6 g) was treated using a procedure similar to the one described in Example 2 sub-part c. except that the reaction mixture was heated to reflux for 2 hours to afford the des-hydroxy compound (0.6 g); MS: m/z=364(M+1); NMR: 2.71 (t,2, J=7.4), 3.05 (s,3), 3.4 (m,1), 4.65 (d,1, J=3.7), 5.1 (m,2), 5.72 (m,1), 6.52 (m,1), 6.81 (d,1 J=2), 7.42 (m,4).

d. 3-(3,4-Dichlorophenyl)-3-(6-chloro-2-methyl-3-oxo-2,3-dihydro-1H-isoindol-1-yl)propionaldehyde. 3-[1-(3,4-Dichlorophenyl)but-3-enyl]-5-chloro-2-methyl-2,3-dihydro-1H-isoindol-1-one (0.93 g) was subjected to a procedure similar to the one described in Example 2 sub-part d. Chromatography, gave the aldehyde (0.30 g); MS: m/z= 380(M+1); NMR: 2.7 (t,2, J=7.3), 3.1 (s,3), 3.43 (m,1), 4.65 (d,1, J=3.7), 5.11 (m,2), 5.73 (m,1), 7.12 (m,6).

EXAMPLE 47

3-[1-(3,4-Dichlorophenyl)-3-(4-(2-oxoperhydro-pyrimidine-1-yl)piperidino)propyl]-4,5,6,7-tetrafluoro-2-methyl-2,3-dihydroisoindol-1-one hydrochloride 3-(3,4-Dichlorophenyl)-3-(4,5,6,7-tetrafluoro-2-methyl-3-oxo-2,3-dihydro-1H-isoindol-1-yl)propionaldehyde (0.43 g) was coupled to 4-(2-oxoperhydropyrimidine-1-yl) piperidine (0.183 g) by a method similar to that described in Example 8. The reaction product was not purified by chromatography but converted to the corresponding hydrochloride salt as described in the Example 8 to afford the desired 3-[1-(3,4-Dichlorophenyl)-3-(4-(2-oxoperhydropyrimidine-1-yl)piperidino)propyl]-2-methyl-2,3-dihydro-4,5,6,7-terafluoro-isoindol-1-one hydrochloride (0.465 g); mp 220° C. (d); MS: m/z=587(M+1); NMR: 1.18 (m,4), 2.67 (m,4), 3.36 (s,3), 4.58 (m,1), 4.90 (s,1), 6.87–7.37 (m,3). Analysis for C$_{27}$H$_{28}$Cl$_2$N$_4$O$_2$F$_4$.1.5.HCl.2H$_2$O: Calculated: C, 47.82; H, 4.98, N, 8.26; Found: C, 48.15; H, 4.73; N, 7.99.

The intermediate 3-(3,4-dichlorophenyl)-3-(4,5,6,7-tetrafluoro-2-methyl-3-oxo-2,3-dihydro-1H-isoindol-1-yl)propionaldehyde was synthesized as described below.

a. N-Methyl-2,3,4,5-tetrafluorobenzamide. A method similar to that used in Example 16 sub-part a. was used except the 2,3,4,5-teraflurobenzoic acid (15 g) was used instead of 2-bromo-5-fluorobenzoic aid to afford the amide (7.2 g); mp 97–99° C.; MS: m/z=208; NMR: 3.04 (s,3), 6.61 (broad,1), 7.76 (m,1).

b. 3-[1-(3,4-Dichlorophenyl)but-3-enyl]-4,5,6,7-tetrafluoro-3-hydroxy-2-methyl-2,3-dihydroisoindol-1-one. A method similar to that described in Example 40 sub-part b. was used except that N-methyl-2,3,4,5-tetrafluorobenzamide (4.14 g) was used instead of N-methyl-3-(dimethylamino)benzamide. Chromatography, with hexane:isopropanol as the eluent, gave the alcohol (1.092 g); MS: m/z=434(M+1); NMR: 2.3–2.5 (m,1), 2.8 and 3.0 (two peaks 3), 3.47 (ddd,1, J=2.2, 11, 28), 4.92 (m,2), 5.47 (m,1), 6.64–7.28 (m,3).

c. 3-[1-(3,4-Dichlorophenyl)but-3-enyl]-4,5,6,7-tetrafluoro-2-methyl-2,3-dihydroisoindol-1-one. 3-[1-(3,4-Dichlorophenyl)but-3-enyl]-4,5,6,7-tetrafluoro-3-hydroxy-2-methyl-2,3-dihydroisoindol-1-one (1.0 g) was treated using a procedure similar to the one described in Example 2 sub-part c. to give the des-hydroxy compound (0.716 g); MS: m/z=418(M+1); NMR: 2.61 (m,2), 3.3 (s,3), 5.1 (m,2), 5.65 (m,1), 6.78–7.30 (m,3).

d. 3-(3,4-Dichlorophenyl)-3-(4,5,6,7-tetrafluoro-2-methyl-3-oxo-2,3-dihydro-1H-isoindol-1-yl)propionaldehyde. 3-[1-(3,4-Dichlorophenyl)but-3-enyl)-4,5,6,7-tetrafluoro-2-methyl-2,3-dihydroisoindol-1-one (0.70 g) was subjected to a procedure similar to that described in Example 2 sub-part d. Chromatography, gave the aldehyde (0.436 g); MS: m/z=420(M+1).

EXAMPLE 48

3-[1-(3,4-Dichlorophenyl)-3-(4-(2-oxoperhydropyrimidine-1-yl)piperidino)propyl]-5-methoxycarbonyl-2-methyl-2,3-dihydroisoindol-1-one hydrochloride 3-(3,4-Dichlorophenyl)-3-(6-methoxycarbonyl-2-methyl-3-oxo-2,3-dihydrol-1H-isoindol-1-yl)propionaldehyde (0.3 g) was coupled to 4-(2-oxoperhydropyrimidine-1-yl)piperidine (0.135 g) by a method similar to that described in Example 8. The reaction product was not purified by chromatography but converted to the corresponding hydrochloride salt as described in the Example 8 afford the title compound (0.286 g); MS: m/z=573(M+1); NMR (CD$_3$SOCD$_3$): 1.72 (m,4), 2.11 (m,2), 2.50 (m,2), 2.77 (m,1), 3.05 (m,5), 3.77 (broad,1), 3.94 (s,3), 4.33 (m,1), 4.96 (broad,1), 6.83 (d, J=8.8, 1), 7.1 (s,1), 7.37 (d, J=8.2, 1), (d,1, J=7.8), 8.06 (d,1, J=7.8), 8.34 (s,1). Analysis for C$_{29}$H$_{34}$Cl$_2$N$_4$O$_4$.0.5 H$_2$O.2.0 HCl: Calculated: C, 53.14; H, 5.68, N, 8.55; Found: C, 53.34; H, 5.57; N, 8.56.

The intermediate 3-(3,4-Dichlorophenyl)-3-(6-methoxycarbonyl-2-methyl-3-oxo-2,3-dihydro-1H-isoindol-1-yl)propionaldehyde was synthesized as described below.

a. 3-[1-(3,4-Dichlorophenyl)but-3-enyl]-5-trifluoromethylsulfonyl-3-methyl-2,3-dihydroisoindol-1-one. 3-[1-(3,4-Dichlorophenyl)but-3-enyl]-5-hydroxy-2-methyl-2,3-dihydroisoindol-1-one (1.81 g) in dichloromethane was treated with triethylamine (0.66 g) followed by trifluoromethanesulfonyl anhydride (2.32 g). Chromatography, with ethyl acetate:hexane (1:1) as the eluent gave the trifluoromethylsulfonyl compound (0.2.52 g); MS: m/z=494(M+1); NMR: 2.11 (m,2), 2.75 (m, 2), 3.16 (s, 4), 3.2 (s,2), 3.49 (m,2), 4.72 (m,1), 5.05 (m,4), 5.68 (m,2), 7.21 (m,12).

b. 3-[1-(3,4-Dichlorophenyl)but-3-enyl]-5-methoxycarbonyl-3-methyl-2,3-dihydroisoindol-1-one. 3-[1-(3,4-Dichlorophenyl)but-3-enyl]-5-trifluoromethylsulfonyl-3-methyl-2,3-dihydroisoindol-1-one (2.52 g) in dimethylsulfoxide (60 mL) containing methanol (45 mL) was treated with palladium acetate (0.24 g), triethylamine (1.26 mL) and 1,3-bis(diphenylphospheno)propane (0.42 g) and carbon monoxide gas was bubbled while the reaction mixture was warmed to 70° C. The reaction mixture was stirred under an atmosphere of carbon monoxide for 16 hours at 70° C. and then poured in to 300 mL of water. The mixture was extracted with ethyl acetate, dried (anhydrous sodium sulfate) and evaporated. Chromatography, with ethyl acetate:hexane afforded the ester (0.5 g); MS: m/z=404(M+1); NMR: 2.76 (t,2, J=7.4), 3.11 (s,3), 3.48 (m,1), 4.00 (s,3), 4.74 (d,$_1$, J=3.7), 5.13 (m,2), 5.71 (m,1), 6.54 (m,1), 6.82 (d,1, J=2), 7.1 (d,1, J=5.3), 7.74 (d,1, J=7.9), 8.13 (d,1, J=,), 8.29 (s,1).

c. 3-(3,4-Dichlorophenyl)-3-(6-methoxycarbonyl-2-methyl-3-oxo-2,3-dihydrol-1H-isoindol-1-yl)propionaldehyde. 3-[1-(3,4-Dichlorophenyl)but-3-enyl]-5-methoxycarbonyl-3-methyl-2,3-dihydroisoindol-1-one (0.5 g) was subjected to a procedure similar to the one described in Example 2 sub-part d. Chromatography, gave the aldehyde (0.3 g); MS: m/z=406(M+1); NMR: 3.15 (m,5), 3.99 (s,3), 4.11 (m,1), 4.77 (d,1, J=3.5), 6.8 (m,3), 7.14 (d,1, J=8.3), 7.74 (d,1, J=7.9), 8.2 (m,2), 9.78 (s,1).

EXAMPLE 49

3-[1-(3,4-Dichlorophenyl)-3-(4-(2-oxoperhydropyrimidine-1-yl)piperidino)propyl]-6-methoxycarbonyl-2-methyl-2,3-dihydroisoindol-1-one hydrochloride 3-(3,4-Dichlorophenyl)-3-(5-methoxycarbonyl-2-methyl-3-oxo-2,3-dihydro-1H-isoindol-1-yl)propionaldehyde (0.28 g) was coupled to 4-(2-oxoperhydropyrimidine-1-yl)piperidine (0.126 g) by a method similar to that described in Example 8. The reaction product was not purified by chromatography but converted to the corresponding hydrochloride salt as described in the Example 8 to afford the title compound (0.370 g); mp 185–190° C. (d); MS: m/z=573 (M+1); NMR(CD$_3$SOCD$_3$): 1.02 (s,1), 1.14 (m,1), 1.69–1.93 (m,5), 3, 14 (s,3), 3.94 (s,3), 4.59 (m,1), 4.79, 4.79 (s,1), 6.6 (d,1, J=8), 6.89 (s,1), 7.16 (d,1, J=81), 7.86 (d,1, J=8), 8.33 (m,2). Analysis for C$_{29}$H$_{34}$Cl$_2$N$_4$O$_4$.1.5 H$_2$O.1.0 HCl: Calculated: C, 54.68; H, 6.01, N, 8.80; Found: C, 54.86; H, 5.98; N, 8.89.

The intermediate 3-(3,4-dichlorophenyl)-3-(5-methoxycarbonyl-2-methyl-3-oxo-2,3-dihydro-1H-isoindol-1-yl)propionaldehyde was synthesized as described below.

a. N-Methyl-2,5-dibromobenzamide. The amide was prepared from 2,5-dibromobenzoic acid (25 g) using a method similar to that described in Example 16 sub-part a. (15.8 g); mp 155–156° C.; MS: m/z=292(M+1); NMR: 3.0 (d,3, J=4.83), 7.41 (m,2), 7.64 (d,1, J=2.4).

b. 3-[1-(3,4-Dichlorophenyl)but-3-enyl]-6-bromo-3-hydroxy-2-methyl-2,3-dihydroisoindol-1-one. A solution of N-methyl-2,5-dibromobenzamide (5.86 g) in tetrahydrofuran (100 mL) was cooled to −76° C. and treated with phenyl lithium (22.2 mL of 1.8M solution). Upon stirring at −76° C.

for 2 hours, a solution of 2-(3,4-dichloro-pheny)pent-4-enoic acid ethyl ester (5.46 g) in tetrahydrofuran was added and the resulting reaction mixture allowed to warm to the room temperature and stirred for 1 hour. At the end of this period 10% aqueous hydrochloric acid was added and the reaction mixture was extracted with ethyl acetate. The organic layers were washed with sodium bicarbonate solution dried over anhydrous magnesium sulfate and evaporated to afford the crude product. This material was crystallized from ethyl acetate to afford the alcohol as a white solid (2.7 g); mp 225–228° C.; MS: m/z=441(M+1); NMR (CDCl$_3$): 2.5 (m,1), 2.82 (s,3), 3.12 (m,1), 3.28 (dd, J=12, 3), 4.90 (m,2), 5.47 (m,1), 6.31 (dd,1, J=6, 2), 6.65 (d,1, J=2), 7.10 (d,1, J=8.3), 7.60 (m,2), 7.76 (m,1).

c. 3-[1-(3,4-Dichlorophenyl)but-3-enyl]-6-bromo-2-methyl-2,3-dihydroisoindol-1-one. 3-[1-(3,4-Dichlorophenyl)but-3-enyl]-6-bromo-3-hydroxy-2-methyl-2,3-dihydroisoindol-1-one (2.17 g) was subjected to a procedure similar to that described in Example 2 sub-part c. Chromatography, with hexane:isoproponol (9:1) as the eluent, gave the des-hydroxy compound (0.75 g); MS: m/z=426(M+1); NMR: 2.72 (m,2), 3.10 (s,3), 3.39 (m,1), 4.6 (d,1, J=3.8), 5.11 (m,2), 5.70 (m,1), 6.50 (m,1), 6.81 (m,1), 7.14 (m,1), 7.48 (m,1), 7.70 (m,1), 7.85 (m,1).

d. 3-[1-(3,4-Dichlorophenyl)but-3-enyl]-6-methoxycarbonyl-2-methyl-2,3-dihydroisoindol-1-one. A solution of 3-[1-(3,4-dichlorophenyl)but-3-enyl]-6-bromo-2-methyl-2,3-dihydroisoindol-1-one (0.212 g) in dimethylsulfoxide (2 mL) and methanol (3 mL) was treated with triethylamine (0.168 mL) and Pd (1,1'-bisdiphenylphosphino-ferrocene)Cl$_2$ (0.146 g). The resulting mixture was heated to 60° C. under an atmosphere of carbon monoxide for 4 hours. At the end of this period the reaction mixture was diluted with water, extracted twice with ether and the organic layers were washed with water. The combined organic layers were dried and evaporated to afford the crude product. Chromatography, with hexane:isopropanol (9:1) as the eluent, gave the ester (0.105 g); MS: m/z=404(M+1); NMR: 2.73 (m,2), 3.13 (s,3), 3.46 (m,1), 4.72 (d,1, J=3.8), 5.13 (m,2), 5.71 (m,1), 6.50 (m,1), 6.85 (m,1), 7.10 (m,1), 7.70 (m,1), 7.82 (m,1), 8.36 (d1, J=1.2).

e. 3-(3,4-Dichlorophenyl)-3-(5-methoxycarbonyl-2-methyl-3-oxo-2,3-dihydro-1H-isoindol-1-yl)propionaldehyde. 3-[1-(3,4-Dichlorophenyl)but-3-enyl]-6-methoxycarbonyl-2-methyl-2,3-dihydroisoindol-1-one (0.404 g) was subjected to a procedure similar to that described in Example 2 sub-pard d. Chromatography, gave the aldehyde (0.24 g); MS: m/z=406(M+1).

EXAMPLE 50

3-[1-(3,4-Dichlorophenyl)-3-(4-(2-oxoperhydropyrimidine-1-yl)piperidino)propyl]-6-bromo-2-methyl-2,3-dihydro-isoindol-1-one hydrochloride 3-(3,4-Dichlorophenyl)-3-(5-bromo-2-methyl-3-oxo-2,3-dihydro-1H-isoindol-1-yl)propionaldehyde (0.325 g) was coupled to 4-(2-oxoperhydropyrimidine-1-yl)piperidine (0.139 g) by a method similar to that described in Example 8. The reaction product was not purified by chromatography but converted to the corresponding hydrochloride salt as described in the Example 8 to afford the title compound (0.34 g); mp 195–205° C. (d); MS: m/z=595(M+1); NMR (CD$_3$SOCD$_3$): 1.67–1.92 (m,5), 3.29 (s,3), 4.64 (m,2), 5.21 (s,1), 6.63 (d,1, J=7.6), 6.89 (s,1), 7.20 (d,1, J=8), 7.63–7.82 (m,3). Analysis for C$_{27}$H$_{31}$Cl$_2$N$_4$O$_2$Br.0.75 H$_2$O.1.0 HCl: Calculated: C, 50.33; H, 5.24, N, 8.70; Found: C, 50.31; H, 5.33; N, 8.43.

The intermediate 3-(3,4-Dichlorophenyl)-3-(5-bromo-2-methyl-3-oxo-2,3-dihydro-1H-isoindol-1-yl)propionaldehyde was synthesized as described below.

a. 3-(3,4-Dichlorophenyl)-3-(5-bromo-2-methyl-3-oxo-2,3-dihydro-1H-isoindol-1-yl)propionaldehyde. 3-[1-(3,4-Dichlorophenyl)but-3-enyl]-6-bromo-2-methyl-2,3-dihydroisoindol-1-one (0.425 g, Example 49 sub-part c.) was subjected to a procedure similar to that described in Example 2 sub-part d. Chromatography, gave the aldehyde (0.326 g); MS: m/z=428(M+1).

EXAMPLE 51

3-[1-(3,4-Dichlorophenyl)-3-(4-(2-oxoperhydropyrimidine-1-yl)piperidino)propyl]-6-aminocarbonyl-2-methyl-2,3-dihydroisoindol-1-one hydrochloride 3-(3,4-Dichlorophenyl)-3-(5-aminocarbonyl-2-methyl-3-oxo-2,3-dihydro-1H-isoindol-1-yl)propionaldehyde (0.2 g) was coupled to 4-(2-oxoperhydropyrimidine-1-yl)piperidine (0.093 g) by a method similar to that described in Example 8. The reaction product was not purified by chromatography but converted to the corresponding hydrochloride salt as described in the Example 8 to afford the title compound (0.19 g); mp 240–250° C. (d); MS: m/z=558(M+1); NMR: 2.60–2.77 (m,3), 3.29 (broad,3), 4.67 (m,1), 5.21 (s,1), 6.63 (m,1), 6.85 (s,1), 7.19 (d, J=8, 1), 7.63–7.82 (m,3). Analysis for C$_{27}$H$_{31}$Cl$_2$N$_4$O$_2$Br.1.0H$_2$O.1.3HCl.0.$_2$C$_4$H$_{10}$O: Calculated: 54.16; H, 6.04, N, 10.96; Found: C, 54.21; H, 5.86; N, 10.74.

The intermediate 3-(3,4-dichlorophenyl)-3-(5-aminocarbonyl-2-methyl-3-oxo-2,3-dihydro-1H-isoindol-1-yl)propionaldehyde was synthesized as described below.

a. 3-[1-(3,4-Dichlorophenyl)but-3-enyl]-6-carboxy-2-methyl-2,3-dihydroisoindol-1-one. A solution of 3-[1-(3,4-Dichlorophenyl)but-3-enyl]-6-methoxycarbonyl-2-methyl-2,3-dihydroisoindol-1-one (0.45 g) in methanol (10 mL) was treated with 1 N aqueous sodium hydroxide (2 mL) and stirred for 1.5 hours. At the end of this period the reaction mixture was acidified with hydrochloric acid and extracted with ethyl acetate. Upon washing with brine, drying over anhydrous-magnesium sulfate the organic layer was concentrated under reduce pressure to afford the acid; MS: m/z=390(M+1); NMR: 2.74 (t,2, J=7.3), 3.15 (s,3), 3.47 (m,1), 4.76 (dd,1, J=12.9, 3.7), 5.0 (m,2), 5.73 (m,1), 6.53 (m,1), 6.87 (m,1), 7.07 (m,1), 7.47 (m,1), 7.71 (m,1).

b. 3-[1-(3,4-Dichlorophenyl)but-3-enyl]-6-aminocarbonyl-2-methyl-2,3-dihydroisoindol-1-one. 3-[1-(3,4-Dichlorophenyl)but-3-enyl]-6-carboxy-2-methyl-2,3-dihydroisoindol-1-one (0.435 g) in dichloromethane (10 mL) was cooled in ice and treated with two drops of dimethylformamide followed by oxalylchloride (0.175 mL). The reaction mixture warmed to room temperature, stirred for 16h and evaporated. The resulting residue was dissolved in tetrahydrofuran (20 mL) and treated with aqueous ammonium hydroxide. Upon stirring for 1 hour, the reaction mixture was diluted with ethyl acetate and washed (brine), dried, and evaporated. Crystallization from ethyl acetate gave the amide as a solid (0.307 g); mp>213 .C; MS: m/z=389(M+1); NMR: 2.74 (t, J=7.4), 3.14 (s,3), 3,45 (m,1), 4.75 (d,1, J=3.8), 5.13 (m,2), 5.72 (m,1), 6.53 (dd,1, J=8.3, 2.1), 6.83 (d,1, J=2), 7.13 (d,1, J=8.3), 7.75 (d,1, J=8), 8.03 (d,1, J=1.1), 8.24 (m,1).

c. 3-(3,4-Dichlorophenyl)-3-(5-aminocarbonyl-2-methyl-3-oxo-2,3-dihydro-1H-isoindol-1-yl)propionaldehyde. 3-[1-(3,4-Dichlorophenyl)but-3-enyl]-6-aminocarbonyl-2- methyl-2,3-dihydroisoindol-1-one (0.307 g) was subjected to a procedure similar to that described in Example 2 sub-part d. Chromatography, gave the aldehyde (0.20 g); m/z=391(M+1); NMR: 3.11 (s,3), 4.10 (m,1), 4.75 (m,2), 6.6–8.2 (m,6), 9.80 (s,1).

EXAMPLE 52

3-(1-(3,4-Dichlorophenyl)-3-(4-(2-oxoperhydropyrimidine-1-yl)piperidino)propyl]-2,6-dimethyl-2,3-dihydroisoindol-1-one citrate 3-(3,4-Dichlorophenyl)-3-(2,5-dimethyl-3-oxo-2,3-dihydroisoindol-1-yl)propionaldehyde (0.215 g) was coupled to 4-(2-oxo-perhydropyrimidine-1-yl)piperidine (0.108 g) by a method similar to that described in Example 8. The reaction product was purified by chromatography as described in the Example 8. This material was converted to the corresponding citrate salt by treating with citric acid (0.317 g) in methanol and cocentrating under reduced pressure. The resulting material was titurated with ether and concentrated to remove ether to afford the title compound (0.177 g); mp 86–88° C.; MS: m/z=566(M+1); NMR ($CD_3SOCD_3$): 1.80 (m,6), 3.00 (s,3), 4.4 (m,1), 6.68 (dd,1, J=2, 8.3,), 6.87 (d,1, J=2), 7.19 (d,1, J=8), 7.41 (s,1), 7.5 (d,1, J=7.73), 7.75 (d,1, J=7.75). Analysis for $C_{28}H_{34}Cl_2N_4O_2.0.15H_2O.1.2C6H8O7.0.1C4H10O$: Calculated: C, 56.59; H, 5.86, N, 7.76; Found: C, 55.90; H, 6.05; N, 6.74.

The intermediate 3-(3,4-dichlorophenyl)-3-(2,5-dimethyl-3-oxo-2,3-dihydroisoindol-1-yl)propionaldehyde was synthesized as described below.

a. N-Methyl-2-bromo-5-methylbenzamide. A method similar to that described in Example 16 sub-part a. was used, except 2-bromo-5-methyl benzoic acid was used as the acid, to give the amide.

b. 3-[1-(3,4-Dichlorophenyl)but-3-enyl]-3-hydroxy-2,6-dimethyl-2,3-dihydroisoindol-1-one. N-Methyl-2-bromo-5-methyl-benzamide (5.0 g) was subjected to a method similar to that described in Example 16 sub-part b. Chromatography, with hexane:isopropanol (9:1) as the eluent gave the alcohol (2.17 g); NMR: 2.7 (m,9), 5.0 (m,2), 5.6 (m,2), 7.2 (m,6).

c. 3-[1-(3,4-Dichlorophenyl)but-3-enyl]-2,6-dimethyl-2,3-dihydroisoindol-1-one. 3-[1-(3,4-Dichlorophenyl)but-3-enyl]-3-hydroxy-2,6-dimethyl-2,3-dihydroisoindol-1-one (2.10 g) was subjected to a procedure similar to that described in Example 2 sub-part c. Chromatography, with hexane:isopropanol (9:1) as the eluent, gave the des-hydroxy compound (0.43 g); MS: m/z=390(M+1); NMR: 2.3 (s,3), 2.7 (m,2), 3.0 (s,3), 3.4 (m,1), 4.63 (d,1, J=3.7), 5.1 (m,2), 5.7 (m,1), 6.5 (dd,1, J=2, 8), 6.81 (d,1, J=2), 7.3 (m,4).

d. 3-(3,4-Dichlorophenyl)-3-(2,5-dimethyl-3-oxo-2,3-dihydro-1H-isoindol-1-yl)propionaldehyde. 3-[1-(3,4-Dichlorophenyl)but-3-enyl]-2,6-dimethyl-2,3-dihydroisoindol-1-one (0.43 g) was subjected to a procedure similar to that described in Example 2 sub-part d. Chromatography, gave the aldehyde (0.11 g); MS: m/z=364 (M+1); NMR: 2.4 (m,4), 3.0 (m,5), 3.4 (m,1), 4.5 (d,1, J=4.4), 7.3 (m,6), 9.7 (s,1).

EXAMPLE 53

3-[1-(3,4-Dichlorophenyl)-3-(4-(2-oxoperhydropyrimidine-1-yl)piperidino)propyl]-7-chloro-2-methyl-2,3-dihydroisoindol-1-one hydrochloride 3-(3,4-Dichlorophenyl)-3-(4-chloro-2-methyl-3-oxo-2,3-dihydro-1H-isoindol-1-yl)propionaldehyde (0.695 g) was coupled to 4-(2-oxoperhydropyrimidine-1-yl)piperidine (0.31 g) by a method similar to that described in Example 8. The reaction product was not purified by chromatography but converted to the hydrochloride salt to afford the title compound (0.220 g); mp 175–185° C.; MS: m/z=549(M+1); NMR($CD_3OD$): 1.92 (m,4), 2.13 (m,2), 2.54 (m,2), 3.29 (s,3), 3.66 (m,3), 4.37 (m,1), 6.76 (dd,1, J=8.3, 21), 6.96 (d,1, J=21), 7.29 (d,1, J=8), 7.5 (d,1, J=8), 7.65 (t,1, J=7.8), 7.83 (d,1, J=7.5). Analysis for $C_{29}H_{31}Cl_3N_4O_2.2.5 H_2O.1.0$ HCl: Calculated: C, 53.14; H, 5.69, N, 8.55; Found: C, 53.13; H, 5.67; N, 9.51.

The intermediate 3-(3,4-Dichlorophenyl)-3-(4-chloro-2-methyl-3-oxo-2,3-dihydro-1H-isoindol-1-yl) propionaldehyde was synthesized as described below.

a. N-Methyl-2-chlorobenzamide. 2-Chlorobenzoic acid was subjected to a procedure similar to that described in Example 16 sub-part a. to give the amide.

b. 3-[1-(3,4-Dichlorophenyl)but-3-enyl]-3-hydroxy-7-chloro-2-methyl-2,3-dihydroisoindol-1-one. A method similar to that described in Example 28 sub-part b. was used except the temperature was maintained at temperature of −76° C. instead of −40° C. Chromatography, with hexane:ethyl acetate (1:1) as the eluent gave the alcohol (1.1 g); MS: m/z=396(M+1); NMR: 2.44 (m,1), 2.69 (s,3), 3.1 (m,1), 3.3 (dd,1, J=12, 2.9), 4.12 (m,1), 4.89 (m,2), 5.45 (m,1), 6.30 (dd,1, J=8.3, 1.9), 6.58 (d,1, J=1.9), 7.08 (d,1, J=8.2), 7.34 (d,1, J=7.9), 7.53 (t,1, J=7.8), 7.64 (d,1, J=7.5).

c. 3-[1-(3,4-Dichlorophenyl)but-3-enyl]-7-chloro-2-methyl-2,3-dihydroisoindol-1-one. The above alcohol was subjected to a procedure similar to that described in Example 2 sub-part c. Chromatography, with hexane:isopropanol (9:1) gave the des-hydroxy compound (0.77 g); MS: m/z=380(M+1); NMR: 1.9 (m,1), 2.68 (m,1), 3.08 (s,3), 3.4 (m,1), 4.63 (dd,1, J=21, 3.7), 5.15 (m,1), 5.7 (m,1), 6.5 (m,1), 6.87 (dd,1, J=13, 2), 7.17 (m,1), 7.5 (m,3).

d. 3-(3,4-Dichlorophenyl)-3-(4-chloro-2-methyl-3-oxo-2,3-dihydro-1H-isoindol-1-yl)propionaldehyde. 3-[1-(3,4-Dichlorophenyl)-but-3-enyl]-7-chloro-2-methyl-2,3-dihydroisoindol-1-one (0.65 g) was subjected to a procedure similar to that described in Example 2 sub-part d. The reaction product was used without chromatography; MS: m/z=382(M+1); NMR: 1.29 (m,1), 1.94 (m,1), 3.04 (two peaks,3), 4.57 (dd,1, J=27, 3.3), 6.53–7.53 (m,6).

EXAMPLE 54

3-[1-(3,4-Dichlorophenyl)-3-(4-(2-oxoperhydropyrimidine-1-yl)piperidino)propyl]-7-trifluoromethyl-2-methyl-2,3-dihydroisoindol-1-one hydrochloride 3-(3,4-Dichlorophenyl)-3-(4-trifluoromethyl-2-methyl-3-oxo-2,3-dihydro-1H-isoindol-1-yl)propionaldehyde (0.416 g) was coupled to 4-(2-oxoperhydropyrimidine-1-yl) piperidine (0.183 g) by a method similar to that described in Example 8. The reaction product was not purified by chromatography but converted to the hydrochloride salt to afford the title compound (0.34 g); mp 190–205° C. (d); MS: m/z=583(M+1); NMR($CD_3SOCD_3$): 1.66 (m,2), 2.11 (m,1), 3.05 (s,3), 4.37 (m,1), 4.96 (m,1), 6.31 (m,1), 6.75 (m,1), 6.90 (s,1), 7.34 (m,1), 7.82 (s,1), 8.22 (m,1). Analysis for $C_{28}H_{31}Cl_2N_4O_2F_3.1.0 H_2O.1.0$ HCl: Calculated: C, 52.71; H, 5.37, N, 8.78; Found: C, 52.48; H, 5.22; N, 8.46.

The intermediate 3-(3,4-Dichlorophenyl)-3-(4-trifluoromethyl-2-methyl-3-oxo-2,3-dihydro-1H-isoindol-1-yl)propionaldehyde was synthesized as described below.

a. N-Methyl-2-trifluoromethylbenzamide. A solution of 2-trifluoromethylbenzoyl chloride (50 g) in dichloromethane was added to an ice cold suspension of aqueous methylamine (100 mL of 40% solution) in dichloromethane. Upon stirring the reaction mixture at the room temperature for 1 hour it was diluted with dichloromethane. The organic layer was dried over anhydrous magnesium sulfate and evaporated to afford the desired material as solid (47.73 g); mp 110–112° C.; MS: m/z=204; NMR: 2.0 (d,3, J=4.8), 7.56 (m,5).

b. 3-[1-(3,4-Dichlorophenyl)but-3-enyl]-3-hydroxy-7-trifluoromethyl-2-methyl-2,3-dihydroisoindol-1-one. N-Methyl-2-trifluoromethylbenzamide (10.15) was subjected to a method similar to that described in Example 53 sub-part b. Chromatography, with hexane:ethyl acetate (1:1) as the eluent afforded the alcohol (3.36 g); MS: m/z=430 (M+1); NMR: 2.79 and 3.0 (two peaks,3), 3.4 (dd,1, J=12, 3.6), 4.91 (m,2), 5.45 (m,1), 6.32–7.96 (m,6).

c. 3-[1-(3,4-Dichlorophenyl)but-3-enyl]-7-trifluoromethyl-2-methyl-2,3-dihydroisoindol-1-one. 3-[1-(3,4-Dichlorophenyl)but-3-enyl]-3-hydroxy-7-trifluoromethyl-2-methyl-2,3-dihydroisoindol-1-one was subjected to a procedure similar to that described in Example 2 sub-part c. Chromatography, with hexane:ethyl acetate (1:1) as the eluent, gave the des-hydroxy compound (2.2 g); MS: m/z=414(M+1); NMR: 2.65 (m,2), 3.09 (s,3), 3.4 (m,1), 4.71 (d,1, J=3.6), 5.1 (m,2), 5.7 (m,1), 6.59 (dd,1, J=8.2, 2.1), 6.83 (d,1, J=2.1), 7.2 (d,1, J=8.3), 7.7 (m,3).

d. 3-(3,4-Dichlorophenyl)-3-(4-trifluoromethyl-2-methyl-3-oxo-2,3-dihydro-1H-isoindol-1-yl) propionaldehyde. 3-[1-(3,4-Dichlorophenyl)but-3-enyl]-7-trifluoromethyl-2-methyl-2,3-dihydroisoindol-1-one (2.0 g) was subjected to a procedure similar to that described in Example 2 sub-part d. The resulting material (1.7 g) was used in the next step without further purification: MS: m/z=416(M+1); NMR: 2.83 (dd,1, J=18, 5.6), 3.04 (s,3), 4.09 (m,1), 4.74 (d,1, J=3), 6.74 (dd,1, J=8.3, 2.2), 6.95 (d,1, J=2.2), 7.26 (d,1, J=8.2), 7.75 (m,3), 9.75 (s,1).

EXAMPLE 55

3-[1-(3,4-Dichlorophenyl)-3-(4-(2-oxopiperidino)-4-(methylaminocarbonyl)piperidino)propyl]-2-methyl-2,3-dihydroisoindol-1-one citrate 3-(3,4-Dichlorophenyl)-3-(2-methyl-3-oxo-2,3-dihydroxy-1H-isoindol-1-yl)propionaldehyde (0.62g) was coupled to 4-(2-oxopiperidino)-4-(methylaminocarbonyl) piperidine (0.469 g) by a method similar to that described in Example 8. The reaction product was purified by chromatography and converted to the citrate salt as described in Example 52 to afford the title compound; MS: m/z 571 (M+1); NMR (CD$_3$OD): 1.74–1.76 (m,2), 1.85–1.88 (m,2), 1.93–2.04 (m,2), 2.20–2.34 (m,7), 2.41–2.63 (m,5), 2.66 (s,3), 3.15 (s,3), 3.41–3.45 (m,2), 3.57–3.65 (m,1), 4.86 (d,1, J=4.1), 6.67 (dd,1, J=8.4, 2.1), 6.83 (d,1, J=2.1), 7.16 (d,1, J=8.3), 7.54 (m,1), 7.61 (m,1), 7.67 (m,1), 7.84(m,1). Analysis for C$_{30}$H$_{36}$N$_4$O$_3$Cl$_2$.1.4 H$_2$O.1.05 C$_6$H$_8$O$_7$: Calculated C, 54.60; H, 5.96; N, 7.02; Found: C, 54.60; H, 5.94, N, 6.84.

The intermediate 3-(3,4-dichlorophenyl)-3-(2-methyl-3-oxo-2,3-dihydro-1H-isoindol-1-yl)propionaldehyde was synthesized as described at Example 2 sub-parts a–d.

EXAMPLE 56

3-[1-(3,4-Dichlorophenyl)-3-(4-acetamido-4-phenylpiperidino)propyl]-5-hydroxy-2-methyl-2,3-dihydroisoindol-1-one hydrochloride 3-(3,4-Dichlorophenyl)-3-(6-hydroxy-2-methyl-3-oxo-2,3-dihydro-1H-isoindol-1-yl)propionaldehyde (1.5 g) was coupled to 4-acetamido-4-phenylpiperidine (0.7 g) by a method similar to that described in Example 8. The reaction product was purified by chromatography and converted to the corresponding hydrochloride salt as described in Example 8 to afford the title compound (1.26 g); mp 212–225° C.; MS: m/z=566(m+1); NMR: 2.00 (s,3), 2.22 (m,5), 2.5 (m,2), 2.7(m,2), 2.99(s,3), 3.54(m,1), 4.54 (d,1, J=3.4), 5.81 (s,1), 6.6 (m,1), 6.7 (m,1), 6.97 (m,1), 7.11 (m,2), 7.31 (m,6), 7.50 (d,1, J=8).

The intermediate 3-(3,4-dichlorophenyl)-3-(6-hydroxy-2-methyl-3-oxo-2,3-dihydro-1H-isoindol-1-yl) propionaldehyde was synthesized from 3-[1-(3,4-dichlorophenyl)but-3-enyl]-5-methoxy-2-methyl-2,3-dihydroisoindol-1-one (described Example 30 sub-part c.) using a sequence similar to that described in Example 31 sub-parts a.–b.

EXAMPLE 57

(3R)-3-[(1S)-1-(3,4-Dichlorophenyl)-3-(4-(2-oxoperhydropyrimidine-1-yl)piperidino)propyl]-2-methyl-2,3-dihydroisoindol-1-one hydrochloride.

(3S)-3-(3,4-Dichlorophenyl)-3-((1R)-2-methyl-3-oxo-2,3-dihydro-1H-isoindol-1-yl)propionaldehyde (2.09 g) was coupled to 4-(2-oxoperhydropyrimidine-1-yl)piperidine (1.111 g) by a method similar to that described in Example 1 to give the title compound (3.31 g); mp 170–210° C. (d); [α]$_D$=36° (c=1.0); MS: m/z=515(M+1); NMR (CD$_3$SOCD$_3$): 1.66 (m,2), 1.78 (m,2), 2.18 (m,2), 3.05 (s,3), 4.39 (m,1), 4.86 (d,1, J=4), 6.75 (m,1), 6.95 (d,1, J=1.6), 7.3 (d,1, J=8), 7.5 (m,2), 7.64 (m,1), 7.94 (d,1, J=7.6). Analysis for C$_{27}$H$_{32}$Cl$_2$N$_4$O.1.5 H$_2$O.1.5 HCl: Calculated: C, 54.30; H, 6.16, N, 9.38; Found: C, 54.33; H, 5.92; N, 9.19.

The intermediate (3S)-3-(3,4-dichlorophenyl)-3-[(1R)-2-methyl-3-oxo-2,3-dihydro-1H-isoindol-1-yl] propionaldehyde was prepared as follows.

a. 3-[(1S)-1-(3,4-Dichlorophenyl)but-3-enyl]-3-hydroxy-2-methyl-2,3-dihydroisoindol-1-one. A solution of N-methylbenzamide (11.49 g) in tetrahydrofuran was cooled to −78° C. and treated with a solution of tert-butyllithiun (100 mL of 1.7 M solution in pentane) so that the temperature of the mixture did not rise above −65° C. The reaction mixture was warmed to 0° C. and stirred for 15 minutes. The reaction mixture was cooled to −78° C. and treated with anhydrous lanthanumtrichloride (26.42 g prepared by heating lanthanumtri-chlorideheptahydrate under vacuum at 120° C. for 16 hours). The resulting suspension was warmed to 0° C. and stirred for 15 minutes. The mixture was cooled to −78° C. and treated with a solution of (2S)-2-(3,4-dichlorophenyl)-N-methoxy-N-methylpent-4-enamide (14.36 g) in tetrahydrofuran (150 mL). The mixture was warmed to 0° C., stirred until it reached 12° C., and was treated with aqueous hydrochloric acid. The mixture was extracted with ether and the combined ether layers were washed (brine, aqueous sodium bicarbonate), dried, and evaporated. The resulting material was treated with ethyl acetate, stirred for 16 hours, cooled to 0° C. and filtered to afford the desired material as a solid. The mother liquor was purified by chromatography, with hexane:isopropanol (9:1) as the eluent to afforded additional 3-[(1S)-1-(3,4-dichlorophenyl)but-3-enyl]-3-hydroxy-2-methyl-2,3-dihydroisoindol-1-one (6.43 g); [α]$_D$=40° (c=1.0, ethanol); MS: m/z=288(M+1); NMR: 2.51 (m,1), 2.91 (s,3), 3.16 (m,1), 3.30 (dd,1, J=12, 3), 4.91 (m,2), 5,48 (m,1), 6.31 (dd,1, J=8, 1.8), 6.53 (d,1, J=2), 7.05 (d,1 J=8), 7.15 (m,1), 7.29 (m,1), 7.57 (t,1, J=7.4), 7.72 (m,1).

b. (3R)-3-[(1S)-1-(3,4-Dichlorophenyl)but-3-enyl]-2-methyl-2,3-dihydroisoindol-1-one. 3-[(1S)-1-(3,4-Dichlorophenyl)but-3-enyl]-3-hydroxy-2-methyl-2,3-dihydroisoindol-1-one (6.0 g) was subjected to conditions similar to those described in Example 16, sub-part c. Chromatography, with hexane:isopropanol (9:1) as the eluent gave (3R)-3-[(1S)-1-(3,4-dichlorophenyl)but-3-enyl]-2-methyl-2,3-dihydroisoindol-1-one (2.41 g); $[\alpha]_D=75°$ (c=1 ethanol); MS: m/z=346(M+1); NMR: 2.05 (m,2), 3.25 (s,3), 3.5 (m,1), 4.63 (d,1, J=3.6), 4.95 (m,2), 5.7 (m,1), 6.77 (m,1), 7.07 (dd,1, J=8.2, 2.1), 7.3–7.5 (m,3), 7.8 (m,1).

c. (3S)-3-(3,4-Dichlorophenyl)-3-[(1R)-2-methyl-3-oxo-2,3-dihydro-1H-isoindol-1-yl]propionaldehyde. (3R)-3-[(1S)-1-(3,4-dichlorophenyl)but-3-enyl]-2-methyl-2,3-dihydroisoindol-1-one (3.9 g) was subjected to conditions similar to those described in Example 2 sub-part d. Chromatography, with hexane:ethyl acetate (1:1) gave the desired (3S)-3-(3,4-dichlorophenyl)-3-[(1R)-2-methyl-3-oxo-2,3-dihydro-1H-isoindol-1-yl]propionaldehyde (3.92 g); MS: m/z=348(M+1); NMR: 3.04 (s,3), 4.07 (m,1), 4.69 (d,1, J=3.5), 6.68 (dd,1l, J=8.3, 2.2), 6.9 (d,1, J=2.1), 7.2 (d,1, J=8.3), 7.57 (m,3), 7.76 (d,1, J=7.5), 9.77 (s,1).

The intermediate (2S)-2-(3,4-dichlorophenyl)-N-methoxy-N-methylpent-4-enamide was prepared as follows.

d. (2S)-2-(3,4-Dichlorophenyl)-N-methoxy-N-methylpent-4-enamide. A solution of (2S)-2-(3,4-dichlorophenyl)pent-4-enoic acid (48.8 g) in 250 mL of dichloromethane was cooled in ice and treated with two drops of dimethylformamide followed by 19.25 mL of oxalylchloride. The reaction mixture was allowed to warm to the room temperature over a period of 16 hours and was concentrated under reduce pressure. The material was dissolved in dichloromethane (600 mL), cooled to 0° C. and treated with N,O-dimethylhydroxylamine hydrochloride (22.17 g). The resulting suspension was treated drop wise with triethylamine (53.9 mL). The reaction mixture was stirred for 30 minutes and treated with 1N hydrochloric acid (200 mL). The organic layer was separated, washed twice with 1N hydrochloric acid and brine, dried and evaporated to afford the desired (2S)-2-(3,4-dichlorophenyl)-N-methoxy-N-methylpent-4-enamide (53.29 g); $[\alpha]_D=51°$ (c=3.35 ethanol); MS: m/z=288 (M+1); NMR: 2.43 (m,1), 2.77 (m,1), 3.16 (s,3), 3.54 (s,3), 4.03 (t,1, J=7.2), 5.03 (m,2), 5.68 (m 1), 7.17 (dd,1, J=8.3, 2), 7.37(m 2).

EXAMPLE 58

(3R)-3-1(1S)-1-(3,4-Dichlorophenyl)-3-(4-(2-methylsulfonylphenyl)piperidino)propyl]-2-methyl-2,3-dihydroisoindol-1-one hydrochloride A solution of (3S)-3-(3,4-Dichlorophenyl)-3-((1R)-2-methyl-3-oxo-2,3-dihydro-1H-isoindol-1-yl)propionaldehyde (0.468 g) in methanol (10 mL) was treated with 4-(2-methylsulfonylphenyl)piperidine (0.3 g) as described in Example 8. The resulting material was not purified by chromatography but was transformed into the hydrochloride to afford the title compound (0.51 g); $[\alpha]_D=$ 21° (c=1.0 Ethanol); mp 190–200° C. (dec); MS: m/z=571 (M+1); NMR(CD$_3$SOCD$_3$): 1.99 (broad,2), 2.37 (broad, 2), 3.35 (s,3), 3.60 (s,3), 4.9 (d,1, J=3.6), 6.8 (dd,1, J=8.4, 2), 7.0 (s,1), 7.3–7.98 (m,9). Analysis for C$_{30}$H$_{32}$Cl$_2$N$_2$O$_2$S.HCl.H$_2$O: Calculated: C, 57.55; H, 5.63; N, 4.47; Found: C, 57.32; H, 5.33; N, 4.50.

EXAMPLE 59

(3R)-3-[(1S)-1-(3,4-Dichlorophenyl)-3-(4-(2-oxo-piperidino)piperidino)propyl]-2-methyl-2,3-dihydroisoindol-1-one hydrochloride A solution of (3S)-3-(3,4-Dichlorophenyl)-3-((1R)-2-methyl-3-oxo-2,3-dihydro-1H-isoindol-1-yl) propionaldehyde (0.596 g) was treated with 4-(2-oxopiperidino)piperidine (0.311 g) as described in Example 8. The resulting material was not purified by chromatography but was transformed into the hydrochloride to afford the title compound (0.51 g); $[\alpha]_D=28°$ (c=1.0 Ethanol); mp 150–160° C. (dec); MS: m/z=514(M+1); NMR (CD$_3$SOCD$_3$): 1.69 (broad,5), 2.23 (broad, 3), 3.06 (s,3), 4.57 (m,1), 4.87 (d,1, J=3.7), 6.75 (dd,1, J=8.4, 2), 6.96 (d,1, J=2), 7.33 (d,1, J=8), 7.50 (m,2), 7.62 (m,1), 7.92 (d,1, J=7.6). Analysis for C$_{28}$H$_{33}$Cl$_2$N$_3$O$_2$.1.5 HCl.H$_2$O: Calculated: C, 57.27; H, 6.26; N, 7.16; Found: C, 57.24; H, 6.15; N, 7.26.

EXAMPLE 60

3-[1-(3,4-Dichlorophenyl)-3-(4-(2-oxopiperidino) piperidino)propyl]-2-ethyl-2,3-dihydroisoindol-1-one hydrochloride A solution of 3-(3,4-dichlorophenyl)-3-(2-ethyl-3-oxo-2, 3-dihydro-1H-isoindol-1-yl)propionaldehyde (0.476 g) was treated with 4-(2-oxopiperidino)piperidine (0.945 g) as described in Example 8. The resulting material was not purified by chromatography but was transformed into the hydrochloride to give title compound (0.51 g); mp 135–140° C. (dec); MS: m/z=558(M+1); NMR(CD$_3$OD): 1.22 (m,3), 2.2 (m,12), 3.0 (m,11), 4.5 (m,1), 5.04 (d,1, J=3.85), 7.27 (m,7). Analysis for C$_{29}$H$_{35}$Cl$_2$N$_3$O$_2$.HCl.H2O: Calculated: C, 59.74; H, 6.56; N, 7.20; Found: C, 59.77; H, 6.33; N, 6.83.

The intermediate 3-(3,4-dichlorophenyl)-3-(2-ethyl-3-oxo-2,3-dihydro-1H-isoindol-1-yl)propionaldehyde was synthesized as described below.

a. N-Ethylbenzamide. A solution of benzoylchloride (14.06 g) in dichloromethane was added to a suspension of 24.27 mL of 70% aqueous solution of ethyl amine in 100 mL of dichloromethane cooled in ice. After stirring at room temperature for 16 hours the reaction mixture was diluted with 5% aqueous sodium hydroxide. The organic layer was dried (anhydrous sodium sulfate), and evaporated to give the amide (13.86 g); mp 62–63° C.; MS: m/z=150(M+1); NMR: 1.24 (t,3, J=7), 3.49 (m,2), 6.29 (s,1), 7.4 (m,3), 7.7 (m,2).

b. 3-[1-(3,4-Dichlorophenyl)but-3-enyl]3-hydroxy-2-ethyl-2,3-dihydroisoindol-1-one. A solution of N-ethylbenzamide (2.235 g) in tetrahydrofuran (200 mL) was cooled to −76° C. and treated with tert-butyl lithium (17.64 mL of 1.7 M solution) slowly such that the temperature of the reaction mixture remained below −76° C. The resulting yellow solution was stirred at −76° C. for 45 minutes, and was warmed to 0° C. The resulting solution was cooled to −78° C. and treated with a solution of 2-(3,4-dichlorophenyl)pent-4-enoic acid ethyl ester (4.095 g) in tetrahydrofuran was added. The reaction mixture was stirred at −76° C. for 15 minutes and then allowed to warm to 0° C. and stirred at that temperature for 30 minutes. At the end of this period, a saturated solution ammonium chloride was added (200 mL) and the reaction mixture was extracted with ethyl acetate. Upon washing with ammonium chloride solution, drying and evaporation the organic layer afforded the crude product. Chromatography, with hexane:isopropanol (9:1) afforded two isomers of the alcohol: isomer A (0.938 g); mp 145–150° C.; MS: m/z=406(M+1); NMR (CDCl$_3$): 1.3 (m,3), 2.54 (m,1), 1.9 (m,1), 2.1 (m,1), 3.0 (s,1), 3.4 (m,2), 3.7 (m,1), 4.8 (m,2), 5.41 (m,1), 7.4 (m,7): Isomer B (0.92 g); mp 68–70° C.; MS: m/z=406(M+1); NMR(CDCl$_3$): 1.2 (m,3), 2.5 (m,1), 3.2 (m,4), 4.92 (m,2), 5.5 (m,1), 6.31 (d,d, J=8.2, 2, 1), 6.56 (d, J=2, 1), 7.59 (m,5).

c. 3-[1-(3,4-Dichlorophenyl)but-3-enyl]-2-ethyl-2,3-dihydroisoindol-1-one. 3-[1-(3,4-Dichlorophenyl)but-3-enyl]-3-hydroxy-2-ethyl-2,3-dihydroisoindol-1-one (3.1 g) was treated by a method similar to that described in Example 2 sub-part c. to afford the des-hydroxy compound (2.46 g): MS: m/z=390(M+1); NMR(CDCl$_3$): 1.2 (m,3), 2.7 (m,1), 3.3 (m,2), 3.48 (m,2), 4.2 (m,1), 4.75–4.88 (m,1), 5.0 (m,2), 5.6 (m,1), 7.4 (m, 7).

d. 3-(3,4-Dichlorophenyl)-3-(2-ethyl-3-oxo-2,3-dihydro-1H-isoindol-1-yl)propionaldehyde. 3-[1-(3,4-Dichlorophenyl)but-3-enyl]-2-ethyl-2,3-dihydroisoindol-1-one (2.5 g) was subjected to a procedure similar to that described in Example 2 sub-part d. Chromatography, gave the aldehyde (0.74 g); MS: m/z=392(M+1); NMR (CDCl$_3$): 1.17 (t, J=7, 3), 2.4 (m,$_1$), 3.2 (m,2), 4.1 (m,2), 4.78–4.84 (m,1), 7.4 (m,7), 9.6–9.7 (m,1).

EXAMPLE 61

3-[1-(3,4-Dichlorophenyl)-3-[4-(2-methylsulfinylphenyl)piperidino)propyl]-2-ethyl-2,3-dihydroisoindol-1-one hydrochloride 3-(3,4-Dichlorophenyl)-3-(2-ethyl-3-oxo-2,3-dihydro-1H-isoindol-1-yl)propionaldehyde (0.24 g) and 4-(2-methylsulfinylphenyl)piperidine (0.224 g) were coupled using conditions similar to those described Example 1 to give the title compound (0.198 g); mp 150° C. (dec); MS: m/z=571(M+1); NMR (CD$_3$OD): 1.3 (m,3), 2.0 (m,6), 2.6 (m,1), 3.3 (m,12), 5.05 (m,1), 7.28 (m,1l). Analysis for C$_{31}$H$_{34}$Cl$_2$N$_2$O$_2$S.1.0 HCl.0.9 H$_2$O: Calculated: C, 59.83; H, 5.96; N, 74.50; Found: C, 59.55; H, 5.76; N, 4.89.

The intermediate 4-(2-methylsulfinylphenyl)piperidine was prepared as described in Example 66 sub-parts d.–h.

EXAMPLE 62

3-[1-(3,4-Dichlorophenyl)-3-(4-(2-oxoperhydropyrimidin-1-yl)piperidino)propyl]-2-ethyl-2,3-dihydroisoindol-1-one hydrochloride A solution of 3-(3,4-dichlorophenyl)-3-(2-ethyl-3-oxo-2,3-dihydroisoindol-1-yl)propionaldehyde (0.36 g) was treated with 4-(2-oxoperhydropyrimidin-1-yl)piperidine (0.183 g) as described in Example 8. The resulting material was purified by chromatography and was transformed into the hydrochloride to afford the title compound (0.23 9); mp 165–170° C.; MS: m/z=557(M+1); NMR(CD$_3$OD): 2.3 (m,7), 2.9 (m,10), 3.45 (m,1), 4.0 (m,1), 4.3 (m,1), 5.0 (m,1), 7.25 (m,7). Analysis for C$_{28}$H$_{34}$Cl$_2$N$_4$O$_2$.1.0 HCl.1.2 H$_2$O: Calculated: C, 57.23; H, 6.41; N, 9.53; Found: C, 57.16; H, 6.21; N, 9.28.

EXAMPLE 63

3-[1-(3,4-Dichlorophenyl)-3-(4-(2-methylthiophenyl)piperidino)propyl]-2-ethyl-2,3-dihydroisoindol-1-one hydrochloride 3-(3,4-Dichlorophenyl)-3-(2-ethyl-3-oxo-2,3-dihydro-1H-isoindol-1-yl)propionaldehyde (0.724 g) was coupled to 4-(2-methylthiophenyl)piperidine (0.414 g) by a method similar to that described in Example 8. The reaction product was not purified by chromatography but converted to the hydrochloride salt to afford the title compound (0.63 g); mp 110–140° C. (d); MS: m/z=553(M+1); NMR (CDCl$_3$): 1.19 (m,3), 2.0 (m,2), 2.45 (s,3), 2.68 (m,7), 3.16 (m,3), 3.56 (m,4), 4.18 (m,1), 4.86 (d,1, J=3.7), 6.56–7.79 (m,11). Analysis for C$_{31}$H$_{34}$Cl$_2$N$_2$OS.HCl: Calculated: C, 63.1; H, 5.97, N, 4.75; Found: C, 62.94; H, 5.94; N, 4.82.

EXAMPLE 64

3-[1-(3,4-Dichlorophenyl)-3-(4-(2-methylsulfonylphenyl)piperidino)propyl]-2-ethyl-2,3-dihydroisoindol-1-one hydrochloride 3-(3,4-Dichlorophenyl)-3-(2-ethyl-3-oxo-2,3-dihydro-1H-isoindol-1-yl) propionaldehyde (0.724 g) was coupled to 4-(2-methylsufonyl-phenyl)piperidine (0.706 g) by a method similar to that described in Example 8. The reaction product was not purified by chromatography but converted to the hydrochloride salt to afford the title compound (0.64 g); mp 168–175° C. (d); MS: m/z=585(M+1); NMR (CDCl$_3$): 1.19 (m,3), 2.0 (m,3), 2.35 (m,7), 2.95 (s,3), 4.87 (m,1), 6.56–8.01 (m,11). Analysis for C$_{31}$H$_{34}$Cl$_2$N$_2$O$_3$S.1.5 HCl.1.5 H$_2$O: Calculated: C, 55.79; H, 5.82, N, 4.20; Found: C, 55.90; H, 5.45; N, 4.20.

EXAMPLE 65

3-[1-(3,4-Dichlorophenyl)-3-(4-(2-methylsulfinylphenyl)piperidino)propyl]-2-propyl-2,3-dihydroisoindol-1-one hydrochloride A solution of 3-(3,4-dichlorophenyl)-3-(2-propyl-3-oxo-2,3-dihydro-1H-isoindol-1-yl)propionaldehyde (0.235 g) was treated with 4-(2-methylsulfinylphenyl)piperidine (0.236 g) as described in Example 8. The resulting material was purified by chromatography and was transformed into the hydrochloride to afford the title compound (0.09 g); mp 78–85° C. (dec); MS: m/z=583(M+1); NMR(CD$_3$OD): 0.92 (m,3), 1.5–4.3 (m,21), 4.98–5.04 (m,1), 7.27 (m,1l). Analysis for C$_{32}$H$_{36}$Cl$_2$N$_2$O$_2$S.1.0 HCl.0.5 H$_2$O: Calculated: C, 61.09; H, 6.08; N, 4.45; Found: C, 60.78; H, 5.68; N, 4.67.

The intermediate 3-(3,4-dichlorophenyl)-3-(2-propyl-3-oxo-2,3-dihydro-1H-isoindol-1-yl)propionaldehyde was prepared as described below.

a. N-Propylbenzamide. A solution of benzoylchloride (11.61 g) in dichloromethane was added to a solution of 17.73 g of propylamine in 100 mL of dichloromethane cooled in ice. Upon stirring at room temperature for 16 hours, the reaction mixture was diluted with 5% aqueous sodium hydroxide and the organic layer was dried over anhydrous sodium sulfate. Evaporation of the organic layer afforded the crude product (14.93 g). This material was distilled under reduced pressure to afford the desired material as a solid: mp 72–74° C.; MS: m/z=164(M+1); NMR: 0.97 (t,3, J=7), 1.64 (m,2), 6.39 (s,1), 7.4 (m,3), 7.76 (m,2).

b. 3-[1-(3,4-Dichlorophenyl)but-3-enyl]-3-hydroxy-2-propyl-2,3-dihydro-1H-isoindol-1-one. Using a procedure similar to that described in Example 60 sub-part b., except replacing N-ethylbenzamide with N-propylbenzamide (2.44 g), the alcohol (3.8 g) was prepared; MS: m/z=389(M+1); NMR(CDCl$_3$): 1.21 (m,3), 2.7 (m,2), 3.4 (m,3), 4.1 (m,2), 5.0 (m,3), 5.7 (m,1), 7.4.(m,7).

c. 3-[1-(3,4-Dichlorophenyl)but-3-enyl]-2-propyl-2,3-dihydroisoindol-1-one. 3-[1-(3,4-Dichlorophenyl)but-3-enyl]-3-hydroxy-2-propyl-2,3-dihydro-1H-isoindol-1-one (3.68 g) was treated by the method similar to that described in Example 2 sub-part c. to afford the des-hydroxy compound (0.68 g): MS: m/z=376(M+1); NMR(CDCl$_3$): 0.97 (m,3), 1.6 (m,2), 2.8 (m,1), 3.0 (m,1), 3.4 (m,1), 4.0 (m,1), 4.8 (d,1, J=3.6), 5.1 (m,2), 5.7 (m,1), 7.4 (m,7).

d. 3-(3,4-Dichlorophenyl)-3-(2-propyl-3-oxo-2,3-dihydro-1H-isoindol-1-yl)propionaldehyde. 3-[1-(3,4-Dichlorophenyl)but-3-enyl]-2-propyl-2,3-dihydro-isoindol-1-one (0.65 g) was subjected to a procedure similar to that described in Example 2 sub-part d. Chromatography, gave the aldehyde (0.256 g); MS: m/z=375(M+1); NMR(CDCl$_3$): 0.87 (t,3, J=7), 3.0 (m,3), 4.0 (m,4), 4.80 (d,1, J=3.5), 7.2 (m,7), 9.9 (m,1).

EXAMPLE 66

(3R)-3-((1S)-1-(3,4-Dichlorophenyl)-3-(4-(2-methylsulfinylphenyl)piperidino)propyl]-2-ethyl-2,3-dihydro-isoindol-1-one hydrochloride (3S)-3-(3,4-Dichlorophenyl)-3-1(1R)-2-ethyl-3-oxo-2,3-dihydro-1H-isoindol-1-yl]propionaldehyde (0.4 g) was coupled to 4-(2-methylsulfinylphenyl)piperidine (0.36 g) using a method similar to that described in Example 1, to afford the title compound (0.25 g); mp 120–125° C. (d); MS: m/z=569(M+1); NMR (CDCl$_3$): 1.20 (m,3), 2.69 (s,3), 4.88 (m,1), 6.59–7.9 (m,11). Analysis for C$_{31}$H$_{34}$Cl$_2$N$_2$O$_2$S.HCl.1.5 H$_2$O: Calculated: C, 58.82; H, 6.05, N, 4.43; Found: C, 58.51; H, 6.07; N, 4.59.

The intermediate (3S)-3-(3,4-dichlorophenyl)-3-[(1R)-2-ethyl-3-oxo-2,3-dihydro-1H-isoindol-1-yl]propionaldehyde was prepared as follows.

a. (3R)-3-[(1S)-1-(3,4-Dichlorophenyl)but-3-enyl]-2-ethyl-3-hydroxy-2,3-dihydroisoindol-1-one. Using a procedure similar to that described in Example 57 sub-part a., except replacing N-methyl-benzamide with N-ethylbenzamide (1.79 g), (3R)-3-[(1S)-1-(3,4-dichlorophenyl)-but-3-enyl]-2-ethyl-3-hydroxy-2,3-dihydroisoindol-1-one (0.722 g) was prepared; MS: m/z=376(M+1).

b. (3R)-3-[(1S)-1-(3,4-Dichlorophenyl)but-3-enyl]-2-ethyl-2,3-dihydroisoindol-1-one. (3R)-3-[(1S)-1-(3,4-Dichlorophenyl)but-3-enyl]-2-ethyl-3-hydroxy-2,3-dihydroisoindol-1-one (0.32 g) was subjected to conditions similar to those described in Example 16 sub-part c. to give (3R)-3-[(1S)-1-(3,4-dichlorophenyl)but-3-enyl]-2-ethyl-2,3-dihydroisoindol-1-one (0.152 g); MS: m/z=360(M+1).

c. (3S)-3-(3,4-Dichlorophenyl)-3-[(1R)-2-ethyl-3-oxo-2,3-dihydroisoindol-1-yl]propionaldehyde. (3R)-3-[(1S)-1-(3,4-dichlorophenyl)but-3-enyl]-2-ethyl-2,3-dihydroisoindol-1-one (0.5 g) was subjected to conditions similar to those described in Example 2 sub-part d. to give the aldehyde (0.4 g); MS: m/z=360(M+1); NMR: 1.74 (t,3, J=7), 3.13 (m,3), 4.06 (m,2), 4.84 (d,1, J=3.5), 6.63 (dd,1, J=8.3, 2.1), 6.84 (d,1, J=2.2), 7.17 (d,1, J=8.3), 7.49 (m,1), 7.60 (m,2), 7.74 (d,$_1$, J=7.4), 9.80 (s,1).

The intermediate 4-(2-methylsulfinylphenyl)piperidine was prepared as follows.

d. 1-Benzyloxycarbonyl-4-piperidone. A solution of 4-piperidone hydrochloride (70 g) in 1.4 L of saturated sodium bicarbonate solution was treated dropwise with a solution of benzyloxycarbonylchoride (75 mL) in 40 mL of dioxane. The reaction mixture was stirred over night and extracted with three portions of ethyl acetate. The organic layers were washed (1N hydrochloric acid, water, and brine) dired and evaporated to give an oil (96.62 g).

e. 1-Benzyloxycarbonyl-4-hydroxy-4-(2-methythiophenyl)-piperidine. A suspension of magnesium turnings (1.5 g in anhydrous 100 ml of tetrahydrofuran was treated with dibromoethane (11.6 g) in tetrahydrofuran (10 mL). The resulting solution was stirred for 2 hours at room temperature. This solution was added to a solution prepared by treating 2-bromothioanisole (12.5 g) in terahydrofuran (80 mL) cooled to −70° C. with n-butyllithium in pentane (24.6 mL, 2.5 M) and stirring at −70° C. for 1 hour. The resulting reaction mixture was allowed to warm to 0° C. and stirred 2 hours. The reaction mixture was cooled to −78° C. and treated with a solution of 1-benzyloxycarbonyl-4-piperidone ( 14.36 g) in tetrahydrofuran (25 mL). The reaction mixture was allowed to warm to the room temperature, was stirred for 16 hours, and was treated with saturated aqueous ammonium chloride (120 mL). The organic layer was separated and the aqueous layer was extrated with ethyl acetate. The combined organic layers were washed (aqueous sodiub bicarbonate), dried, and evaporated to give material which was purified by chromatography, with hexane:ethyl acetate as the eluent to give 1-benzyloxycarbonyl-4-hydroxy-4-(2-methythiophenyl)piperidine (10 g); MS: m/z=357(M+1); NMR: 2.1 (m,4), 2.53 (s,3), 3.41 (broad,2), 4.11 (s,2), 4.42 (s,1), 5.15 (s,2), 7.34 (m,9).

f. 1-Benzyloxycarbonyl-4-(2-methythiophenyl) piperidine. A solution of 1-benzyloxycarbonyl-4-hydroxy-4-(2-methythiophenyl)-piperidine (10 g) in 100 mL of dichloromethane was treated trifluoroacetic acid (17 mL) and triethylsilane (68 mL). The reaction mixture was stirred at room temperature for 16 hours and was treated with aqueous sodium bicarbonate solution (300 mL). After stirring for 30 minutes, the organic layer was separated, dried (anhydrous sodium sulfate) and evaporated. The resulting material was purified by chromatography, with hexane:ethyl acetate (3:1) as the eluent. The resulting material was heted under reduced pressure at 80° C. for 30 minutes to afford 1-benzyloxycarbonyl-4-(2-methythiophenyl)-piperidine; MS: m/z 342 (M+1); NMR: 1.61 (m,2), 1.82 (m,2), 2.45 (s,3), 2.91 (s,2), 3.04 (m,1), 4.33 (s,2), 5.16 (s,2), 7.26 (m,9).

g. 1-Benzyloxycarbonyl-4-(2-methylsulfinylphenyl) piperidine. A solution of 1-benzyloxycarbonyl-4-(2-methylthiophenyl)piperidine (3.27 g) in 60 mL of chloroform was cooled in ice and treated with trans-2-(phenylsulfonyl)-3-phenyloxaziridine (2.5 g) (Vishwakarma et al., Org. Syn, 66, 203–210). The reaction mixture was allowed to warm to room temperature over 1 hour and the solvent was evaporated. Chromatography, with ethyl acetate:methanol (9:1) as the eluent gave the sulfinyl compound (1.71 g); MS: 358; NMR: 1.6–1.9 (m,4), 2.7 (s,3), 2.8–3.0 (broad,3), 4.4–4.5 (broad,2), 5.2 (s,2), 7.2–7.3 (m,1), 7.3–7.4 (m,5), 7.4–7.5 (m,2), 8.0 (m,1).

h. 4-(2-Methylsulfinylphenyl)piperidine. A solution of 1-benzyloxycarbonyl-4-(2-methylsulfinylphenyl)piperidine (1.66 g) in 8 mL of trifluoroacetic acid was heated to reflux for 45 minutes. The reaction mixture was evaporated and the residue was treated with toluene. Upon evaporating the solvent, the residue was treated with an additional portion of toluene and the process was repeated. The final residue was dried under reduced pressure and purified by chromatography, with dichloromethane:methanol:triethylamine (19:1:1) as the eluent, to give the piperidine (0.87 g); MS: 224; NMR: 1.6–2.4 (m,4), 2.7 (two peaks,3), 2.9–3.2 (m,3), 3.3–3.5 (m,2), 5.3–5.7 (broad,1), 7.4–7.5 (m,3), 7.9–8.0 (m,1).

EXAMPLE 67

(3R)-3-[(1S)-1-(3,4-Dichlorophenyl)-3-(4-((R*)-2-methylsulfinylphenyl)piperidino)propyl]-2-ethyl-2,3-dihydro-isoindol-1-one citric acid salt (3S)-3-(3,4-dichlorophenyl)-3-[(1R)-2-ethyl-3-oxo-2,3-dihydro-1H-isoindol-1-yl]propionaldehyde (1.02 g) was coupled to 4-((R*)-2-methylsulfinylphenyl)piperidine (0.94 g) by a method similar to that described in Example 1. The reaction product was purified by chromatography, with dichloromethane:methanol (9:1) as the eluent, and converted to the citric acid salt (1.11 g); mp 96–110° C.(d); $[\alpha]_D=4.0°$ (c=1 ethanol); MS: m/z=569(M+1); NMR (CD$_3$SOCD$_3$): 1.13 (t,3, J=7), 2.7 (m,23), 5.02 (d,1, J=3.4), 7.32 (m,11). Analysis for C$_{31}$H$_{34}$Cl$_2$N$_2$O$_2$S.1.2 C$_6$H$_8$O$_7$.1.0 H$_2$O: Calculated: C, 56.08; H, 5.61, N, 3.42; Found: C, 56.06; H, 5.22; N, 3.57.

The intermediate 4-[(R*)-2-methylsulfinylphenyl] piperidine was prepared as follows.

a. 1-Benzyloxycarbonyl-4-[(R*)-2-methylsulfinylphenyl]-piperidine. A solution of 2.86 g of (R)-(+)-1,1'-bi-2-naphthol in carbon tetrachloride (100 mL) was treated with titanium tetraisopropoxide (33 mL) followed by water (0.39 mL). After stirring for 2 hours, a solution of 1-benzyloxycarbonyl-4-(2-methythiophenyl)-piperidine (5 g, prepared as described in Example 66, sub-part f.) in carbontetrachloride (20 mL) was added follwed by tert-butylhydro-peroxide (8 mL). The resulting reaction mixture was stirred for 16 hours, and was purified by chromatography, with ethyl acetate as the eluent, to give a 2:1 mixture of enantiomers (2 g), as indicated by high pressure liquid chromatography. This material was purified by fractional crystallization from ethyl acetate:hexane mixtures to afford a single enantioner which was determined to be at least 99% enantiomerically pure by high pressure liquid chromatography. High pressure liquid chromatography was carried out on an Analytical OD column (4.6×250 mM, Catalog Number 7195-00, DIACEL Chemical Industries Limited, New York, N.Y., USA.), with ethanol as the eluent, using a flow rate of 0.3 mL/minute and UV detection (254 nM). The retention time for the major enantiomer was 16.5 minutes, and for the minor enantiomer was 17.5 minutes. The absolute configuration at the sulfoxide center was not determined. The major enantiomer from this preparation was designated 1-benzyloxycarbonyl-4-[(R*)-2-methyl-sulfinylphenyl]piperidine (0.58 g); $[\alpha]_D=-98.6°$ (C=0.73, ethanol); mp 137–138° C.; MS: m/z=368(M+1); NMR: 1.79 (m,2), 2.71 (s,3), 2.94 (m,3), 4.36 (s,2), 5.7 (s,2), 7.64 (m,9).

b. 4-[(R*)-2-Methylsulfinylphenyl]piperidine. A solution of 1-benzyloxycarbonyl-4-[(R*)-2-methylsulfinylphenyl] piperidine (0.55 g) in trifluoroacetic acid (12 mL) was refluxed for 30 minutes. The reaction mixture was evaporated and the residue was triturated with ether. The resulting material was dried under reduced pressure to afford the piperidine as a hygroscopic solid (0.52 g); MS: m/z 224; NMR: 1.88 (m,2), 2.2 (s,3), 3.11 (m,3), 3.57 (s,2), 7.73 (m,4).

The intermediate 1-Benzyloxycarbonyl-4-[(R*)-2-methyl-sulfinylphenyl]piperidine can alternatively be prepared as follows.

c. N-Benzyloxycarbonyl-4-[(R*)-2-methylsulfinylphenyl]-piperidine. To a solution of diethyl-D-tartarate (3.4 mL) in dichloromethane (50 mL) was added titanium tetraisopropoxide (3.0 mL) followed by water (0.18 mL). The resulting solution was stirred vigorously for 30 minutes, treated with N-benzyloxycarbony-4-(2-methylthiophenyl)piperidine (3.41 g), and cooled to −15° C. The reaction mixture was treated with tert-butylhydroperoxide (2 mL) drop wise over a period of 1 minute, and stirred at −15° C. for 40 hours. Water (4 mL) was added, and the solution was stirred vigorously for 1 hour and filtered through a bed of diatomous earth. The filtrate was stirred with 5% aqueous sodium hydroxide (100 mL) for 1 hour and was washed with brine (50 mL). The aqueous layer was extracted with dichloromethane and the combined organic layers were washed (brine), dried (anhydrous sodium sulfate), and evaporated to give a solid product which was crystallized from diisopropyl ether to afford N-Benzyloxycarbonyl-4-[(R*)-2-methyl-sulfinylphenyl] piperidine (3.0 g).

EXAMPLE 68

(3R)-3-[(1S)-1-(3,4-Dichlorophenyl)-3-(4-((S*)-2-methylsulfinylphenyl)piperidino)propyl]-2-ethyl-2, 3-dihydro-isoindol-1-one citric acid salt (3S)-3-(3,4-dichlorophenyl)-3-[(1R)-2-ethyl-3-oxo-2,3-dihydro-1H-isoindol-1-yl]propionaldehyde (0.492 g) was coupled with 4-[(S*)-2-methylsulfinylphenyl]piperidine (0.43 g) by a method similar to that described in Example 1. The resulting material was converted to the citric acid salt (0.504 g); mp 163–179° C.; $[\alpha]_D=59°$ (c=1 ethanol); MS: m/z=569(M+1); NMR (CD$_3$SOCD$_3$): 1.13 (t,3, J=7), 2.85 (m,23), 5.02 (d,1, J=3.4), 7.32 (m,11). Analysis for C$_{31}$H$_{34}$Cl$_2$N$_2$O$_2$S.C$_6$H$_8$O$_7$.2.0 H$_2$O: Calculated: C, 55.71; H, 5.81, N, 3.51; Found: C, 55.76; H, 5.60; N, 3.51.

The intermediate 4-[(S*)-2-methylsulfinylphenyl] piperidine was prepared as follows.

a. N-Benzyloxycarbonyl-4-[(S*)-2-methysulfinylphenyl]-piperidine. Using a method similar to that described in Example 67 sub-part a. except replacing (R)-(+)-bi-2-naphthol with (S)-(−)-bi-2-naphthol, N-benzyloxycarbonyl-4-((S*)-2-methysulfinyl-phenyl) piperidine was prepared (0.6 g); $[\alpha]_D=97°$ (c=1.0, ethanol); MS: m/z=358(M+1); NMR: 1.78 (m,4), 2.71(s,3), 2.92 (m,3), 4.36(s,2), 5.17 (s 2), 7.64 (m,9).

b. 4-[(S*)-2-methysulfinylphenyl]piperidine. Using a procedure similar to that described in Example 67 sub-part b., N-benzyloxycarbonyl-4-[(S*)-2-methysulfinylphenyl] piperidine (0.575 g) was converted to 4-[(S*)-2-methysulfinylphenyl]piperidine (0.56 g); MS: m/z 224(M+ 1); NMR: 1.88 (d,2, J=12), 2.2 (m,4), 2.75 (s,3), 3.11 (m,3), 3.57 (s,2), 7.63 (m,4).

The intermediate N-benzyloxycarbonyl-4-[(S*)-2-methysulfinylphenyl]piperidine can alternatively be prepared as follows.

c. N-Benzyloxycarbonyl-4-[(S*)-2-methysulfinylphenyl]-piperidine. N-Benzyloxycarbonyl-4-(2-methythiophenyl)piperidineas was oxidized using a procedure similar to that described in Example 67 sub-part c., except using diethyl-S-tartarate for the diethyl-D-tartarate used therein, to give N-Benzyloxycarbonyl-4-[(S*)-2-methy-sulfinylphenyl]piperidine.

EXAMPLE 69

(3R)-3-[(1S)-1-(3,4-Dichlorophenyl)-3-(4-pyrid-3-yl-piperidino)propyl]-2-methyl-2,3-dihydroisoindol-1-one hydrochloride A solution of (3S)-3-(3,4-dichlorophenyl)-3-((1R)-2-methyl-3-oxo-2,3-dihydro-1H-isoindol-1-yl) propionaldehyde (0.428 g) was treated with 4-pyrid-3-ylpiperidine (0.20g) as described in Example 8. The resulting material was not purified by chromatography, but was transformed into the hydrochloride to afford the title compound (0.535 g); $[\alpha]_D=34°$ (c=1.0 ethanol); mp 170–210° C. (dec); MS: m/z=494(M+1); NMR: 2.12 (m,4), 3.03 (s,3), 3.69 (m,7), 4.88 (m,1), 6.75 (m,1), 6.96 (m,1), 7.32 (m,1), 7.49 (m,2), 7.63(m,1), 7.92 (m,2), 8.37 (m,1), 8.81 (m,2). Analysis for C$_{28}$H$_{29}$Cl$_2$N$_3$O.2 HCl.H$_2$O: Calculated C, 57.45; H, 5.68; N, 7.18; Found: C, 57.22; H, 5.67; N, 7.12.

The intermediate (3S)-3-(3,4-dichlorophenyl)-3-[(1R)-2-methyl-3-oxo-2,3-dihydro-1H-isoindol-1-yl] propionaldehyde was synthesized as described Example 57 sub-parts a–d.

EXAMPLE 70

3-[1-(3,4-Dichlorophenyl)-3-(4-hydroxy-4-phenylpiperidino)propyl]-6-chloro-2-methyl-2,3-dihydroisoindol-1-one hydrochloride 3-(3,4-Dichlorophenyl)-3-(5-chloro-2-methyl-3-oxo-2,3-dihydroxy-1H-isoindol-1-yl)propionaldehyde was reductively coupled to 4-hydroxy-4-phenylpiperidine using a procedure similar to that described in Example 74, to give the title compound; MS: m/z=571(M+1); NMR: (selected signals) 7.70 (s,1), 7.49–7.58 (m,4), 7.26–7.40 (m,3), 7.20 (d,1), 6.87 (s,1), 6.53 (d,1), 4.62 (d,1). Analysis for $C_{29}H_{29}Cl_3O_2N_2.0.25\ H_2O$: Calculated: C, 63.51; H, 5.42; N, 5.11; Found: C, 63.47; H, 5.56; N, 5.09.

The intermediate 3-(3,4-Dichlorophenyl)-3-(5-chloro-2-methyl-3-oxo-2,3-dihydroxy-1H-isoindol-1-yl)propionaldehyde was prepared as described in Example 99 sub-parts a.–c.

EXAMPLE 71

3-[1-(3,4-Dichlorophenyl)-3-(4-hydroxy-4-phenylpiperidino)propyl]-2-methyl-3-oxo-2,3-dihydro-1H-indazole 3-(3,4-Dichlorophenyl)-3-(2-methyl-3-oxo-2,3-dihydro-1H-indazol-1-yl)propionaldehyde (0.6 g) was coupled to 4-hydroxy-4-phenylpiperidine (0.344 g) by a method similar to that described in Example 8. The reaction product was purified by chromatography and converted to the hydrochloride salt to afford the title compound (0.25 g); mp 140–145° C. (d); MS: m/z=507(M+1); NMR($CD_3SOCD_3$): 1.83 (broad,2), 3.44 (s,3), 5.49 (t,1, J=8),7.16–7.75 (m,12). Analysis for $C_{30}H_{32}Cl_2N_2O.1.0\ H_2O.1.0\ HCl$: Calculated: C, 59.43; H, 5.71, N, 7.43; Found: C, 60.04; H, 5.55; N, 7.42.

The intermediate 3-(3,4-Dichlorophenyl)-3-(2-methyl-3-oxo-2,3-dihydro-1H-indazol-1-yl)propionaldehyde was prepared as described below.

a. 2-Nitro-N-methylbenzamide. A method similar to the one described in Example 28 sub-part a. was used except that 2-nitrobenzoyl chloride (9.23 g) was used instead of o-anisoyl chloride to afford the desired 2-nitro-N-methylbenzamide (8.26 g) as solid; MS: m/z=181(M+1); NMR($CDCl_3$): 3.01 (d,3, J=5), 5.91 (broad,1), 7.49–7.69 (m,3), 8.06 (dd,1, J=8, 1.2).

b. 2-Methyl-3-oxo-2,3-dihydro-1H-indazole. A solution of 2-nitro-N-methylbenzamide (8.26 g) in 50 mL of methanol was treated with 100 mL of 1N sodium hydroxide solution followed by 9.8 g of zinc and the resulting suspension was refluxed for 24 hours. At the end of this period, the reaction mixture was filtered and the residue was washed (methanol). The combined filtrates were evaporated, acidified with 1N hydrochloric acid to pH 7.0 and extracted with dichloromethane. The organic layer was dried and evaporated to afford material which was suspended in 50 mL of ethyl acetate. The resulting solid was filterd to give the indazole (1.57 g); MS: m/z=149(M+1); NMR ($CDCl_3$): 3.49 (s,3), 7.23 (m,2), 7.33 (broad,1), 7.51 (m,1), 7.84 (m,1).

c. 3-[1-(3,4-Dichlorophenyl)but-3-enyl]-2-methyl-3-oxo-2,3-dihydro-1H-indazole. A solution of 2-methyl-3-oxo-2,3-dihydro-1H-indazole in 20 mL of dimethylformamide was treated with 0.16 g of 60% dispersion of sodium hydride in oil. The resulting suspension was stirred for 1 hour and treated with 1.08 g of 1-bromo-1-(3,4-dichloro-phenyl)but-3-ene. The reaction mixture was stirred for 16 hours, diluted with water, extracted with ethyl acetate and the organic layer was washed (brine), dried, and evaporated. Chromatography, with ethyl acetate:hexane (1:1) afforded 3-[1-(3,4-Dichlorophenyl)but-3-enyl]-2-methyl-3-oxo-2,3-dihydro-1H-indazole (0.769 g); MS: m/z=347(M+1); NMR ($CDCl_3$): 2.75 (m,2), 3.37 (s,3), 5.05 (m,2), 5.68 (m,1), 6.98 (d,1, J=8), 7.15–7.26 (m,2), 7.41–7.53 (m,3), 7.83 (d,1, J=7.6).

d. 3-(3,4-Dichlorophenyl)-3-(2-methyl-3-oxo-2,3-dihydro-1H-indazol-1-yl)propionaldehyde. 3-[1-(3,4-Dichlorophenyl)but-3-enyl]-2-methyl-3-oxo-2,3-dihydro-1H-indazole (0.95 g) was subjected to a procedure similar to that described in Example 2 sub-part d. The aldehyde was used without purification (0.6): MS: m/z=349(M+1); NMR ($CDCl_3$): 2.74 (m,1), 3.14 (m,1), 3.34 (s,3), 5.62 (m,1), 6.87 (d,1, J=8.3), 7.22 (m,2), 7.43 (m,3), 7.85 (d,1, J=7.7).

The intermediate 1-Bromo-1-(3,4-dichlorophenyl)but-3-ene was prepared as follows.

e. 1-(3,4-Dichlorophenyl)but-3-en-1-ol. A solution of 3,4-dichlorobenzaldehyde (22.68 g) in tetrhydrofuran (200 mL) at 0° C. was treated with 130 mL of 1 M solution of allylmagnesium bromide in ether. The reaction mixture was allowed to warm to room temperature over a period of 16 hours and poured in a solution of ammonium chloride. Extarction with ethyl acetate, washing the organic layer with brine, drying and evaporating gave material which was purified by chromatography, with hexane:isopropanol (9:1) as the eluent, to afford the alcohol (5.04 g); MS: m/z=217 (M+1); NMR($CDCl_3$) 2.1 (m,1), 2.49 (m,2), 4.71 (m,1), 5.20 (m,2), 5.76 (m,1), 7.15 (m,1), 7.47–7.67 (m,2).

f. 1-Methanesulfonyloxy-1-(3,4-dichlorophenyl)but-3-ene. A solution of 1-(3,4-dichlorophenyl)but-3-en-1-ol in dichloromethane was cooled to −5° C. and treated with triethylamine followed by methanesulfonyl chloride. The reaction mixture was warmed to room temperature and stirred for 2 hours. The mixture was washed (5% solution of hydrochloric acid, sodium bicarbonate solution), dried and evaporated afford the methanesulfonyloxy compound. This material was not further characterized but used in the next step.

g. 1-Bromo-1-(3,4-dichlorophenyl)but-3-ene. A solution of 1-methanesulfonyloxy-1-(3,4-dichlorophenyl)but-3-ene in acetone was treated with lithiumbromide and heated to reflux for 16 hours. The reaction mixture was cooled to the room temperature, evaporated, diluted with ether and washed with water. The aqueous layer was extracted with ether and the organic layers were washed with brine, and evaporated to give an oil. Chromatography, with hexane as the eluent, gave material which was distilled under reduced pressure to give the bromo compound; mp 75–85° C./0.25 mTorr; MS: m/z=199(M-Broad); NMR($CDCl_3$): 2.92 (m,2), 4.85 (t,1, J=7.5), 5.14 (m,2), 5.67,(m,1), 7.23 (m,1), 7.40–7.48 (m,2).

EXAMPLE 72

3-[1-(3,4-Dichlorophenyl)-3-(4-hydroxy-4-phenylpiperidino)propyl]-2-isopropyl)-2,3-dihydroisoindol-1-one hydrochloride 3-(3,4-Dichlorophenyl)-3-(2-isopropyl-3-oxo-2,3-dihydro-1H-isoindol-1-yl)propionaldehyde (0.375 g) was coupled to 4-hydroxy-4-phenylpiperidine (0.177 g) by a method similar to that described in Example 8. The reaction product was purified by chromatography and converted to the hydrochloride salt to afford the title compound (0.233 g); mp 140°C. (d); MS: m/z=537(M+1); NMR($CD_3SOCD_3$): 1.3 (m,3), 1.44 (m,3), 3.7 (broad,1), 3.95 (m,1), 4.90 (m,1), 6.69–7.95 (m,12). Analysis for $C_{31}H_{34}Cl_2N_2O_2 \cdot 1.0\ H_2O \cdot 1.0$ HCl: Calculated: C, 62.89; H, 6.30, N, 4.73; Found: C, 63.15; H, 6.16; N, 4.78.

The intermediate 3-(3,4-dichlorophenyl)-3-(2-isopropyl-3-oxo-2,3-dihydro-1H-isoindol-1-yl)propionaldehyde was prepared as described below.

a. N-isopropylbenzamide. A method similar to the one described in Example 28 sub-part a. was used except that benzoylchlorode (14.05 g) was used insted of 2-methoxybenzoyl chloride and isopropylamine was used instead of methylamine to afford anide (14.2 g) as solid; MS: m/z=164(M+1); NMR(CDCl$_3$): 1.27 (d,1, J=6.5), 4.30 (m,1), 7.45 (m,3), 7.76 (m,2).

b. 3-[1-(3,4-Dichlorophenyl)but-3-enyl]-2-isopropyl-3-hydroxy-2,3-dihydroisoindol-1-one.

A method similar to that described in Example 2 sub-part b. was used except that N-isopropylbenzamide (4.1 g) was used instead of N-methylbenzamide and a temperature of −40° C. was used instead of −15° C. The crude product was not purified or characterized further but used in the next step (9.02 g).

c. 3-[1-(3,4-Dichlorophenyl)but-3-enyl]-2-isopropyl-2,3-dihydroisoindol-1-one. 3-[1-(3,4-Dichlorophenyl)but-3-enyl]-2-isopropyl-3-hydroxy-2,3-dihydroisoindol-1-one (9.02 g) was subjected to a procedure similar to that described in Example 2 sub-part c. Chromatography, with hexane:ethyl acetate (2:1) as the eluent afforded the deshydroxy compound (4.363 g); MS: m/z=374(M+1); NMR (CDCl$_3$): 1.5 (m,6), 2.72 (m,1), 3.87 (m,1), 4.75 (m,1), 4.94 (m,1), 5.17 (m,1), 5.73 (m,1), 6.57 (m,1), 7.08 (m,1), 7.15–7.82 (m,5).

d. 3-(3,4-Dichlorophenyl)-3-(2-isopropyl-3-oxo-2,3-dihydro-1H-isoindol-1-yl)propionaldehyde. 3-[1-(3,4-Dichlorophenyl)but-3-enyl]-2-isopropyl-2,3-dihydroisoindol-1-one (0.374 g) was subjected to a procedure similar to that described in Example 2 sub-part d. The resulting material was used without further purification (0.375 g): MS: m/z=376(M+1).

EXAMPLE 73

3-[(1R*)-1-(3,4-Dichlorophenyl)-3-(4-hydroxy-4-phenyl-piperidino)propyl]-2-methylisoquinol-1-one hydrochloride 3-(3,4-Dichlorophenyl)-3-(2-methyl-1-oxo-isoquin-3-yl)-propionaldehyde (2.94 g) was coupled to 4-hydroxy-4-phenylpiperidine (1.35 g) by a method similar to that described in Example 8. The resulting material was subjected to high pressure liquid chromatography using a CHIRALCEL OD column (5 cm ID×50 cm, supplied by DAICEL Chemical Industries Limited, Japan), with hexane:ethanol:acetonitrile 60:40:2 as the eluent at a flow rate of 54 ml/minute. The first isomer (0.47 g) was converted to the hydrochloride salt to afford the desired 3-[(1R*)-1-(3,4-dichlorophenyl)-3-(4-hydroxy-4-phenylpiperidino)propyl]-2-methylisoqunol-1-one hydrochloride (0.42 g); mp 193–215° C. (d); [α]$_D$=−80.8 (c=1.0 Methanol); MS: m/z= 521(M+1); NMR (CD3OD): 2.0 (d,2, J=14), 2.3–2.7 (m,4), 3.1–3.6 (m,8), 4.46 (t,1, J=8), 7.1 (s,1), 7.2–7.6 (m,10), 7.7–7.8 (m,2), 8.3 (d,1, J=8). Analysis for $C_{30}H_{30}Cl_2N_2O_2 \cdot 1.5\ H_2O \cdot 1.0$ HCl: Calculated: C, 61.6; H, 5.86; N, 4.79; Found: C, 61.56; H, 5.61; N, 4.53.

The intermediate 3-(3,4-dichlorophenyl)-3-(2-methyl-1-oxo-isoquin-3-yl)propionaldehyde was prepared as follows.

a. 3-[1-(3,4-Dichlorophenyl)-3-(tetrahydropyran-2-yloxy)-propyl]-3-hydroxy-2-methyl-3,4-dihydroisoquinol-1-one. Using a procedure similar to that described in Example 1 sub-part c., except using N-methyl-2-methylbenzamide (2.99 g) instead of N-methylbenzamide and tert-butyllithium instead of butyllithium, the alcohol was prepared. The reaction product (11.59 g) was used directly in the next step.

b. 3-[1-(3,4-Dichlorophenyl)-3-hydroxypropyl]-2-methyl-isoquinol-1-one. 3-[1-(3,4-Dichlorophenyl)-3-(tetrahydropyran-2-yloxy)-propyl]-3-hydroxy-2-methyl-3,4-dihydroisoquinol-1-one (11.59 g) was subjected to a procedure similar to that described in Example 1 sub-part d, g). The reaction product was purified by chromatography, with hexane:ethyl acetate (1:1) as the eluent, to give 3-[1-(3,4-dichlorophenyl)-3-hydroxypropyl]-2-methyl-isoquinol-1-one (0.7 g); MS: m/z=363(M+1); NMR (CD$_3$SOCD$_3$) 2.0–2.3 (m,2), 2.6–3.5 (m,5), 4.5 (m,1), 4.7 (t,1, J=5), 6.8 (s,1), 7.2–7.7 (m,6), 8.2 (d,1, J=8,).

c. 3-(3,4-Dichlorophenyl)-3-(2-methyl-3-oxo-isoquin-1-yl)-propionaldehyd. 3-[1-(3,4-Dichlorophenyl)-3-hydroxypropyl]-2-methyl-isoquinol-1-one (2.74 g) was oxidized using a procedure similar to that described in Example 1 sub-part f. The reaction product (2.94 g) was contaminated with the starting material, but was used directly in the next reaction; MS: m/z=360(M+1); NMR(CDCl$_3$): 2.5–3.8 (m,5) 4.1–4.8 (m,1), 6.5–6.6 (m,1), 7.1–7.6 (m,6), 8.4 (m,1).

EXAMPLE 74

3-[1-(3,4-Methylenedioxyphenyl)-3-(4-(2-oxoperhydro-pyrimidine-1-yl)piperidino)propyl]-2-methyl-2,3-dihydroisoindol-1-one hydrochloride A solution of 3-(3,4-methylenedioxyphenyl)-3-(2-methyl-3-oxo-2,3-dihydroxy-1H-isoindol-1-yl) propionaldehyde (0.3 g) in methanol (4 mL) was treated with 4-(2-oxoperhydropyrimidin-1-yl)-piperidine (0.183 g) and acetic acid (0.06 mL). After stirring for 5 minutes, sodium cyanoborohydride (0.063 g) was added and the mixture allowed to stir (48 hours). The reaction was quenched by addition of a saturated solution of sodium bicarbonate (50 mL) and the product extracted into dichloromethane. The organic solution was dried and the solvent removed to give an oil. This oil was purified by chromatography, eluting with methanol:dichloromethane (15:85) to afford the pure free base. This material was dissolved in methanol (4 mL) and anhydrous citric acid (0.094 g) was added. The solvent was evaporated to give the title compound as a white solid (0.33 g); MS: m/z=491(M+ 1); NMR: (selected signals) 7.84 (d,1), 7.63 (m,1), 7.47 (2), 6.64 (d,1), 6.29 (m,3), 5.87 (d,2). Analysis for $C_{28}H_{34}O_4N_4 \cdot C_6H_8O_7 \cdot H_2O$: Calculated: C, 58.28; H, 6.32; N, 7.99; Found: C, 58.13; H, 6.22; N, 7.73.

The intermediate 3-(3,4-methylenedioxyphenyl)-3-(2-methyl-3-oxo-2,3-dihydroxy-1H-isoindol-1-yl) propionaldehyde was prepared as follows.

a. 3,4-Methylenedioxyphenylacetic acid methyl ester. A solution of 3,4-methylenedioxyphenylacetic acid (10 g), and concentrated sulfuric acid (1 mL) in methanol (139 mL) was heated at 60° C. for 12 hours. The reaction was quenched by addition of a saturated solution of sodium bicarbonate (50 mL) and the solvent evaporated. The resulting oil was distilled (broad p 129° C., 1 Torr) to provide the ester; m/z=195(M+1).

b. 2-(3,4-Methylenedioxyphenyl)pent-4-enoic acid methyl ester. A solution of the ester (2.05 g) in tetrahydrofuran (30 mL) was added to a −78° C. solution of lithium bis(trimethylsilyl)amide (11.7 mL of a 1.0M solution in hexane). After stirring for 1 hour, allyl bromide (1 mL in 5 mL of tetrahydrofuran) was added and the solution allowed to warm to room temperature. The reaction was quenched by addition of a saturated solution of ammonium chloride and the product extracted into ether. The ether solution was washed (water), dried, and evaporated. Chromatography, with ether:hexane (5:95) to gave 2-(3,4-methylenedioxyphenyl)pent-4-enoic acid methyl ester (2.0 g); TLC: Rf=, 0.5, ether:hexane (5:95); MS: m/z=235(M+1).

c. 3-[1-(3,4-Methylenedioxyphenyl)but-3-enyl]-3-hydroxy-2-methyl-2,3-dihydroisoindol-1-one. To a solution of N-methyl benzamide (3.51 g) in tetrahydrofuran (70 mL) @–78° C. was added n-butyllithium (21.3 mL of a 2.5 M solution in hexane) and the solution was warmed to 0° C. and stirred for 1 hour. The solution was recooled to –78° C. and to this was added a solution of 2-(3,4-methylenedioxyphenyl)pent-4-enoic acid methyl ester (6.0 g) in tetrahydrofuran (20 mL). The solution was stirred for 2 hours and then warmed to 0° C. The reaction was quenched by addition of a saturated solution of ammonium chloride and the product extracted into ethyl acetate. The organic solution was washed with a saturated solution of ammonium chloride, water, and brine. The solution was dried and the solvent evaporated to provide a crystalline material which was triturated with ether, collected and dried to provide the hydroxy compound (4.66 g); TLC: Rf=, 0.4, methanol:dichloromethane (3:97); MS: m/z=338(M+1).

d. 3-[1-(3,4-Methylenedioxyphenyl)but-3-enyl]-2-methyl-2,3-dihydroisoindol-1-one. To a solution of the hydroxy compound (9.2 g) in trifluoroacetic acid (38 mL) was added triethylsilyl hydride (40 mL) and the resulting solution was allowed to stir for 1 hour. The solvent was evaporated and the resulting material was diluted with ethyl acetate and washed with a saturated solution of sodium bicarbonate, water, and brine. The organic layers were dried and the solvent evaporated. The resulting material was purified by chromatography, eluting with isopropanol/hexane (5:95 to 10:90) to provide the des-hydroxy compound (4.1 g); TLC: Rf=, 0.5, methanol:dichloromethane (3:97); MS: m/z=322(M+1).

e. 3-(3,4-Methylenedioxyphenyl)-3-(2-methyl-3-oxo-2,3-dihydroxy-1H-isoindol-1-yl)propionaldehyde. To a solution of 3-[1-(3,4-methylenedioxyphenyl)but-3-enyl]-2-methyl-2,3-dihydroisoindol-1-one (0.35 g) in tetrahydrofuran (10 mL) and water (5 mL) was added sodium periodate (0.52 g), osmium tetroxide (0.1 mL of a 4% solution in water) and the resulting mixture was allowed to stir for 3 hours. The reaction mixture was filtered through celite, diluted with ethyl acetate and washed with a saturated solution of sodium thiosulfate, water, and brine. The organic portions were dried and the solvent removed by evaporation. Chromatography, with ethyl acetate as the eluent, gave the aldehyde (0.3 g); TLC: Rf=, 0.35, ethyl acetate; MS: m/z=324 (M+1).

EXAMPLES 75–97

Using a reductive coupling procedure similar to that described in Example 74, except replacing 3-(3,4-methylenedioxy-phenyl)-3-(2-methyl-3-oxo-2,3-dihydroxy-1H-isoindol-1-yl)-propionaldehyde, with the required aldehyde and 4-(2-oxoperhydro-pyrimidin-1-yl)piperidine with the required piperidine, the following compounds of formula I wherein $Q^2$ is 2-methyl-3-oxo-2,3-dihydro-1H-isoindol-1-yl, $Q^3$ is hydrogen, and $Q^1$ and $Q^4$ have the indicated values were prepared.

Example 75. $Q^1$=4-Acetamido-4-phenylpiperidino, $Q^4$=3,4-methylene-dioxyphenyl; MS: m/z=526(M+1); NMR: (selected signals) 7.80 (m,2), 7.61 (t,1), 7.51 (m,2), 7.35 (m,3), 7.17 (m,1), 6.60 (d,1), 6.33 (d,3), 6.22 (s,1), 5.86 (d,2), 4.80 (d,1). Analysis for $C_{32}H_{35}O_4N_3 \cdot C_6H_8O_7 \cdot 0.1 H_2O$: Calculated: C, 62.03; H, 6.16; N, 5.71; Found: C, 62.10; H, 6.27; N, 5.51.

Example 76. $Q^1$=4-(2-Oxoperhydropyrimidin-1-yl)piperidino, $Q^4$=4-chlorophenyl; MS: m/z=481(M+1); NMR: (selected signals) 7.88 (d,1), 7.64–7.44 (m,3), 7.10 (d,2), 6.76 (d,2), 4.81 (d,1), 4.40–4.20 (m,1). Analysis for $C_{27}H_{33}O_2N_4Cl \cdot C_6H_8O_7 \cdot 1.25 H_2O$: Calculated: C, 58.32; H, 6.45; N, 8.24; Found: C, 58.20; H, 6.25; N, 8.16.

Example 77. $Q^1$=4-Acetamido-4-phenylpiperidino, $Q^4$=4-chlorophenyl; MS: m/z=516(M+1); NMR: (selected signals) 7.91 (d,1), 7.70–7.15 (m,10), 6.87 (d,2), 4.88 (d,1), 3.65–3.57 (m,3). Analysis for $C_{31}H_{34}O_2N_3Cl \cdot C_6H_8O_7 \cdot 0.20 H_2O$: Calculated: C, 62.43; H, 6.00; N, 5.90; Found: C, 62.19; H, 5.96; N, 5.76.

Example 78. $Q^1$=4-Hydroxy-4-phenylpiperidino, $Q^4$=4-chlorophenyl; MS: m/z=475(M+1); NMR: (selected signals) 7.92 (d,1), 7.66 (t,1), 7.55–7.25 (m,9), 7.16 (d,2), 6.85 (d,2), 4.88 (d,1), 3.68–3.52 (m,4). Analysis for $C_{29}H_{31}O_2N_2Cl \cdot C_6H_8O_7 \cdot 0.20 H_2O$: Calculated: C, 62.67; H, 5.92; N, 4.18; Found: C, 62.27; H, 5.85; N, 4.03.

Example 79. $Q^1$=4-(2-Oxoperhydropyrimidin-1-yl)piperidino, $Q^4$=4-bromophenyl; MS: m/z=525(M+1); NMR: (selected signals) 7.87 (d,1), 7.65 (t,1), 7.50 (m,2), 7.26 (d,2), 6.72 (d,2), 6.24 (s,1), 4.84 (d,1). Analysis for $C_{27}H_{33}O_2N_4Br \cdot C_6H_8O_7 \cdot 0.25 H_2O$: Calculated: C, 54.89; H, 5.79; N, 7.76; Found C, 54.72; H, 5.85; N, 7.69.

Example 80. $Q^1$=4-Acetamido-4-phenylpiperidino, $Q^4$=4-bromophenyl; MS: m/z=560(M+1); NMR: (selected signals) 7.98 (s,1), 7.84 (d,1), 7.62 (m,1), 7.49 (m,2), 7.34–7.20 (m,7), 6.74 (d,2), 4.83 (d,1). Analysis for $C_{31}H_{34}O_2N_3Br \cdot C_6H_8O_7 \cdot 0.25 H_2O$: Calculated: C, 58.69; H, 5.66; N,5.55; Found: C, 58.30; H, 5.60; N, 5.53.

Example 81. $Q^1$=4-(2-Oxoperhydropyrimidin-1-yl)piperidino, $Q^4$=4-trifluoromethylphenyl; MS: m/z=515(M+1); Analysis for $C_{28}H_{33}O_2N_4F_3 \cdot C_6H_8O_7 \cdot 0.5 H_2O$: Calculated: C, 57.05; H, 5.91; N, 7.82; Found: C, 56.83; H, 5.85; N, 7.60.

Example 82. $Q^1$=4-Acetamido-4-phenylpiperidino, $Q^4$=4-trifluoromethyl-phenyl; MS: m/z=550 (M+1); Analysis for $C_{32}H_{34}O_2N_3F_3 \cdot C_6H_8O_7 \cdot 0.25 H_{20}$: Calculated: C, 61.16; H, 5.74; N, 5.63; Found: C, 60.97; H, 5.83; N, 5.62.

Example 83. $Q^1$=4-Hydroxy-4-phenylpiperidino, $Q^4$=4-trifluoromethyl-phenyl; MS: m/z=509(M+1); Analysis for $C_{30}H_{31}O_2N_2F_3 \cdot C_6H_8O_7 \cdot 0.5 H_2O$: Calculated: C, 60.93; H, 5.68; N, 3.95; Found: C, 60.85; H, 5.74; N, 3.92.

Example 84. $Q^1$=4-(2-Oxoperhydropyrimidin-1-yl)piperidino, $Q^4$=3-chlorophenyl, isolated as the free base; MS: m/z=509(M+1); NMR: (selected signals) 7.71 (d,1), 7.53–7.63 (m,2), 7.47 (t,1), 7.08 (d,1), 6.99 (t,1), 6.72 (s,1), 6.60 (d,1), 4.62 (d,1). Analysis for $C_{27}H_{33}O_2N_4Cl \cdot 0.5 H_2O$: Calculated: C, 66.18; H, 6.99; N, 11.43; Found: C, 66.23; H, 6.80; N, 11.56.

Example 85. $Q^1$=4-Acetamido-4-phenylpiperidino, $Q^4$=3-chlorophenyl; MS: m/z=544(M+1); NMR: (selected signals) 7.88 (d,1), 7.69 (d,1), 7.59 (d,1), 7.50 (t,1), 7.23–7.42 (m,5), 7.04–7.12 (m,2), 6.71 (m,2), 4.92 (d,1). Analysis for $C_{31}H_{34}O_2N_3Cl \cdot C_6H_8O_7 \cdot 0.5 H_2O$: Calculated: C, 61.96; H, 6.04; N, 5.86; Found: C, 61.76; H, 6.20; N, 5.56.

Example 86. $Q^1$=4-(2-Oxoperhydropyrimidin-1-yl)piperidino, $Q^4$=3,4-difluorophenyl; MS: m/z=483(M+1); NMR: (selected signals) 7.81 (d,1), 7.62 (dt,1), 7.45 (m,2), 7.09 (m,2), 6.73 (m,1), 6.69 (broad s,1), 4.82 (d,1). Analysis for $C_{27}H_{32}O_2N_4F_2 \cdot C_6H_8O_7 \cdot 0.7\ H_2O$: Calculated: C, 57.66; H, 6.07; N, 8.15; Found: C, 57.59; H, 6.07; N, 8.15.

Example 87. $Q^1$=4-Acetamido-4-phenylpiperidino, $Q^4$=3,4-difluorophenyl; MS: m/z=518(M+1); NMR: (selected signals) 7.80 (dd,2), 7.60 (t,1), 7.48 (m,2), 7.09 (m,2), 6.73 (m,1), 6.69 (broad s,1), 4.82 (d,1). Analysis for $C_{31}H_{33}O_2N_3F_2 \cdot C_6H_8O_7 \cdot 0.5\ H_2O$: Calculated: C, 61.83; H, 5.89; N, 5.84; Found: C, 61.78; H, 6.01; N, 5.56.

Example 88. $Q^1$=4-Acetamido-4-phenylpiperidino, $Q^4$=4-methoxyphenyl; MS: m/z=512(M+1); NMR: (selected signals) 8.03 (s,1), 7.85 (d,1), 7.60 (m,1), 7.48 (m,2), 7.32 (m,3), 7.21 (m,1), 6.64 (m,4), 4.80 (d,1). Analysis for $C_{32}H_{37}O_3N_3 \cdot C_6H_8O_7 \cdot 0.7\ H_2O$: Calculated: C, 63.71; H, 6.52; N, 5.86; Found: C, 63.67; H, 6.47; N, 5.74.

Example 89. $Q^1$=4-(2-Oxoperhydropyrimidin-1-yl)piperidino, $Q^4$=2,4-dichlorophenyl; MS: m/z=515(M+1); NMR: (selected signals) 7.81 (d,1), 7.51–7.70 (m,4), 7.15 (dd,1), 6.75 (d,1), 6.23 (broad s,1), 4.88 (d,1), 3.99–4.13 (m,2). Analysis for $C_{27}H_{32}O_2N_4Cl_2 \cdot C_6H_8O_7 \cdot 1.0\ H_2O$: Calculated: C, 54.62; H, 5.83; N, 7.72; Found: C, 54.68; H, 5.66; N, 7.74.

Example 90. $Q^1$=4-Acetamido-4-phenylpiperidino, $Q^4$=2,4-dichlorophenyl; MS: m/z=550(M+1); NMR: (selected signals) 7.51–7.95 (m,6), 7.18–7.35 (m,7), 6.88 (d,1), 4.88 (d,1), 4.00–4.04 (m,1). Analysis for $C_{31}H_{33}O_2N_3Cl_2 \cdot C_6H_8O_7 \cdot 0.7\ H_2O$: Calculated: C, 58.42; H, 5.69; N, 5.52; Found: C, 58.40; H, 5.54; N, 5.84.

Example 91. $Q^1$=4-(2-Oxopiperidino)piperidino, $Q^4$=4-methoxycarbonyl-phenyl; MS: m/z=504(M+1); NMR: (selected signals) 7.86 (d,1), 7.62 (m,3), 7.45 (d,2), 6.91 (d,2), 4.87 (d,1), 4.36 (broad t,1). Analysis for $C_{30}H_{37}O_4N_3 \cdot 1.0\ C_6H_8O_7 \cdot 1.0\ H_2O$: Calculated: C, 59.97; H, 6.57; N, 5.73; Found: C, 59.78; H, 6.30; N, 5.84.

Example 92. $Q^1$=4-(2-Oxoperhydropyrimidin-1-yl)piperidino, $Q^4$=3-trifluoromethylphenyl. Analysis for $C_{28}H_{33}F_3N_4O_2 \cdot 1.0\ C_6H_8O_7 \cdot 0.25\ H2O$: Calculated: C, 57.41; H, 5.88; N, 7.87; Found: C, 57.29; H, 5.95; N, 7.56.

Example 93. $Q^1$=4-Acetamido-4-phenylpiperidino, $Q^4$=3-trifluoromethyl-phenyl. Analysis for $C_{32}H_{34}F_3N_3O_2 \cdot 1.0\ C_6H_8O_7 \cdot 0.5\ H_2O$: Calculated: C, 60.79; H, 5.77; N, 5.57; Found: C, 61.02; H, 5.65; N, 5.88.

Example 94. $Q^1$=4-hydroxy-4-phenylpiperidino, $Q^4$=3-trifluoromethyl-phenyl. Analysis for $C_{30}H_{31}F_3N_2O_2 \cdot 1.0\ C_6H_8O_7 \cdot 0.5\ H_2O$: Calculated: C, 60.92; H, 5.68; N, 3.94; Found: C,. 60.65; H, 5.89; N, 3.65.

Example 95. $Q^1$=4-(2-Oxoperhydropyrimidin-1-yl)piperidino, $Q^4$=3,4-dimethylphenyl. Analysis for $C_{29}H_{38}N_4O_2 \cdot 1.2\ C_6H_8O_7 \cdot 1.0\ H2O$: Calculated: C, 60.12; H, 6.91; N, 7.74; Found: C, 60.21; H, 6.95; N, 7.96.

Example 96. $Q^1$=4-Acetamido-4-phenylpiperidino, $Q^4$=3,4-dimethylphenyl; Analysis for $C_{33}H_{39}N_3O_2 \cdot 1.0\ C6H_8O_7 \cdot 0.8\ H_2O$: Calculated: C, 65.40; H, 6.83; N, 5.86; Found: C, 65.56; H, 6.99; N, 5.61.

Example 97. $Q^1$=4-(2-Oxoperhydropyrimidin-1-yl)piperidino, $Q^4$=4-methoxyphenyl. Analysis for $C_{28}H_{36}N_4O_3 \cdot 1.0\ C_6H_8O_7 \cdot 1.7\ H_2O$: Calculated: C, 58.39; H, 6.83; N, 8.01; Found: C, 58.02; H, 6.75; N, 7.80.

The intermediate aldehydes for Examples 75–97 were prepared using a sequence similar to that described in Example 74 sub-parts a.–e. by substituting the requsite acid for the 3,4-methylenedioxy-phenylacetic acid used in Example 74 sub-part a.

EXAMPLE 98

3-[1-(4-Methoxycarbonylphenyl)-3-(4-(2-oxoperhydro-pyrimidine-1-yl)piperidino)propyl]-2-methyl-2,3-dihydroisoindol-1-one hydrochloride 3-(4-Methoxycarbonylphenyl)-3-(2-methyl-3-oxo-2,3-dihydro-1H-isoindol-1-yl)propionaldehyde and 4-(2-oxoperhydropyrimidine-1-yl)-piperidine were reductively coupled using a procedure similar to that described in Example 74 to give the title compound; MS: m/z=505(M+1); NMR: (selected signals) 7.87 (d,1), 7.64 (m,3), 7.45 (d,2), 6.91 (d,2), 6.24 (broad s,1), 4.87 (d,1), 4.18 (m,1). Analysis for $C_{29}H_{36}O_4N_4 \cdot 1.0\ C_6H_8O_7 \cdot 1.0\ H_2O$: Calculated: C, 58.81; H, 6.48; N, 7.83; Found: C, 58.62; H, 6.21; N, 7.81.

The intermediate 3-(4-methoxycarbonylphenyl)-3-(2-methyl-3-oxo-2,3-dihydro-1H-isoindol-1-yl) propionaldehyde was prepared as follows.

a. 3-[1-(4-Hydroxyphenyl)but-3-enyl]-2-methyl-2,3-dihydroisoindol-1-one. To a 0° C. solution of 3-[1-(4-methoxy-phenyl)but-3-enyl]-2-methyl-2,3-dihydroisoindol-1-one (0.56 g) in dichloromethane (6 mL) was added boron tribromide (1.82 mL) and the solution allowed to warm to room temperature and stirr for 12 hours. The reaction was quenched by addition of water and the product extracted into ethyl acetate. The organic portion was washed with 1 N sodium hydroxide and the aqueous layer separated and made acidic to pH=5 with 1 N HCl. This solution was extracted with ethyl acetate and the organic portion was dried, and the solvent evaporated. The resulting mass crystallized upon standing to give the alcohol as a white solid (0.15 g); TLC: Rf=0.25, ethyl acetate:hexane (1:1); MS: m/z=294(M+1).

b. 3-[1-(4-Trifluoromethylsulfonyloxyphenyl)but-3-enyl]-2-methyl-2,3-dihydroisoindol-1-one. To a solution of the alcohol (0.77 g) in dichloromethane (25 mL) was added N-phenyltrifluoro-methanesulfonimide (1.22 g), triethylamine (0.47 mL) and the reaction stirred for 12 hours. The solvent was evaporated and the residue purified by chromatography, eluting with ethyl acetate:hexane (1:1) to provide the triflate (1.0 g); TLC: Rf=0.40, ethyl acetate:hexane (1:1); MS: m/z=426(M+1).

c. 3-[1-(4-Methoxycarbonylphenyl)but-3-enyl]-2-methyl-2,3-dihydroisoindol-1-one. A solution of the triflate (0.95 g), bis(diphenylphospinyl)propane (0.2 g), triethylamine (0.8 mL), palladium acetate (0.1 g), and dimethyl sulfoxide (10 mL) in methanol (20 mL) was placed under a carbon monoxide atmosphere and heated at 70° C. for 12 hours. The reaction was diluted with ethyl acetate and washed with water, and brine. The organic layer was dried and the solvent removed by evaporation. The product was purified by chromatography, eluting with ethyl acetate:hexane (1:1), to provide the methyl ester (0.37 g); TLC: Rf=0.45, ethyl acetate:hexane (1:1); MS: m/z=336(M+1).

d. 3-(4-Methoxycarbonylphenyl)-3-(2-methyl-3-oxo-2,3-dihydroxy-1H-isoindol-1-yl)propionaldehyde. 3-[1-(4-Methoxycarbonyl-phenyl)but-3-enyl]-2-methyl-2,3-dihydroisoindol-1-one was subjected to a procedure similar to that described in Example 74 sub-part e. to give the aldehyde; TLC: Rf=0.35, ethyl acetate:hexane (3:1); MS: m/z=338(M+1).

EXAMPLE 99

3-[1-(3,4-Dichlorophenyl)-3-(4-(2-oxoperhydropyrimidine-1-yl)piperidino)propyl]-6-chloro-2-methyl-2,3-dihydroisoindol-1-one hydrochloride 3-(3,4-Dichlorophenyl)-3-(5-chloro-2-methyl-3-oxo-2,3-dihydroxy-1H-isoindol-1-yl)propionaldehyde and 4-(2-oxoperhydro-pyrimidine-1-yl)piperidine were reductively coupled using a procedure similar to that described in Example 74 to give the title compound; MS: m/z=577(M+1); NMR: (selected signals) 7.70 (s,1), 7.54 (s,2), 7.13 (d,1), 6.84 (s,1), 6.49 (d,1), 4.60 (d,1), 4.55 (s,1). Analysis for $C_{27}H_{31}Cl_3O_2N_4 \cdot 0.5\ H_2O$: Calculated: C, 58.02; H, 5.77; N, 10.02; Found: C, 58.22; H, 5.79; N, 9.79.

The intermediate 3-(3,4-dichlorophenyl)-3-(5-chloro-2-methyl-3-oxo-2,3-dihydroxy-1H-isoindol-1-yl) propionaldehyde was prepared as follows.

a. 3-[1-(3,4-Dichlorophenyl)but-3-enyl]-6-chloro-3-hydroxy-2-methyl-2,3-dihydroisoindol-1-one. Using a procedure similar to that described in Example 74 sub-part c., except replacing N-methylbenzamide with N-methyl-2-bromo-5-chlorobenzamide, the alcohol was prepared; TLC: Rf=0.45, hexane:isopropanol (90:10), MS: m/z=396(M+1).

b. 3-[1-(3,4-Dichlorophenyl)but-3-enyl]-6-chloro-2-methyl-2,3-dihydroisoindol-1-one. The alcohol was subjected to a procedure similar to that described in Example 74 sub-part d. to give the des-hydroxy compound; TLC Rf=0.36, hexane:isopropanol (90:10), MS: m/z=380(M+1).

c. 3-(3,4-Dichlorophenyl)-3-(5-chloro-2-methyl-3-oxo-2,3-dihydroxy-1H-isoindol-1-yl)propionaldehyde. The des-hydroxy compound was subjected to a procedure similar to that described in Example 74 sub-part e. to give the aldehyde; TLC: Rf=0.1, hexane:isopropanol (90:10), MS: m/z= 382 (M+1).

EXAMPLE 100

3-[1-(3,4-Dichlorophenyl)-3-(4-acetamido-4-phenylpiperidino)propyl]-6-chloro-2-methyl-2,3-dihydroisoindol-1-one hydrochloride 3-(3,4-Dichlorophenyl)-3-(5-chloro-2-methyl-3-oxo-2,3-dihydroxy-1H-isoindol-1-yl)propionaldehyde was reductively coupled to 4-acetamido-4-phenylpiperidine using a procedure similar to that described in Example 74, to give the title compound; MS: m/z=584(M+1); NMR: (selected signals) 7.71 (s,1), 7.54 (s,2), 7.21–7.41 (m,5), 7.16 (d,1), 6.87 (s,1), 6.53 (d,1), 5.46 (s,1). Analysis for $C_{31}H_{32}Cl_3O_2N_3 \cdot 0.5\ H_2O$: Calculated: C, 62.69; H, 5.60; N, 7.07; Found: C, 62.73; H, 5.50; N, 7.00.

EXAMPLE 101

(3R*)-3-[(1S*)-1-(4-Bromo-3-chlorophenyl)-3-(4-(2-oxoperhydropyrimidine-1-yl)piperidino)propyl]-2-methyl-2,3-dihydroisoindol-1-one citrate (3S*)-3-(4-Bromo-3-chlorophenyl)-3-((1R*)-2-methyl-3-oxo-2,3-dihydroxy-1H-isoindol-1-yl)propionaldehyde and 4-(2-oxoperhydropyrimidine-1-yl)piperidine were reductively coupled using a procedure similar to that described in Example 74 to give the title compound as a white solid; mp 105 C° (dec); TLC solvent (free base) 9:1 dichloromethant:methanol, $R_f$=0.44; NMR: (selected signals) 4.26 (m,1), 4.84 (d,1), 6.28 (s,1), 6.65 (d,1), 6.92 (d,1), 7.49 (m,3), 7.64 (m,1), 7.90 (d,1); MS: (CI, CH$_4$) m/z=561(M+1). Analysis for $C_{27}H_{32}BrClN_4O_2 \cdot 1.0\ C_6H_8O_7 \cdot 1.0\ H_2O$: Calculated: C, 51.47; H, 5.49; N, 7.28; Found: C, 51.53; H, 5.53; N, 6.79.

a. 2-(4-Bromo-3-chlorophenyl)pent-4-enoic acid methyl ester. Using a procedure similar to that described in Example 74 sub-part b., except replacing 3,4-methylenedioxyphenylacetic acid methyl ester with 4-bromo-3-chlorophenylacetic acid methyl ester [O. K. Behens et al, U.S. Pat. No. 2,479,295 (1949)], the vinyl compound was prepared. Chromatography, with hexane:ethyl ether (gradient, 100:0-95:5) as the eluent, gave the a yellow oil; TLC (95:5 hexane:ethyl ether), $R_f$=0.32; NMR: 2.45 (m,1), 2.71 (m,1), 3.59 (s,3), 3.85 (t,1), 4.99 (m,1), 5.67 (m,1), 7.22 (dd,1), 7.58 (d,1), 7.72 (d,1); MS: m/z=305(M+1).

b. (3*)-3-[(1*)-1-(4-Bromo-3-chlorophenyl)but-3-enyl]-3-hydroxy-2-methyl-2,3-dihydroisoindol-1-one. Using a procedure similar to that described in Example 74 sub-part c., the alcohol was prepared; Chromatography, with hexane:ethyl ether (9:1) followed by hexane:isopropanol (93:7) followed by hexane:isopropanol (9:1), gave the desired syn-diasteiomer which was designated (3*)-3-[(1*)-1-(4-Bromo-3-chlorophenyl)but-3-enyl]-3-hydroxy-2-methyl-2,3-dihydroisoindol-1-one as a tacky solid; TLC: (solvent, hexane:isopropanol 9:1), $R_f$=0.26; NMR indicated a 3:1 syn to anti mixture; MS: m/z=408(M+1). The anti diasteriomer, had an $R_f$=0.31 (solvent, hexane:isopropanol 9:1).

c. (3R*)-3-[(1S*)-1-(4-Bromo-3-chlorophenyl)but-3-enyl]-2-methyl-2,3-dihydroisoindol-1-one. The alcohol was subjected to a procedure similar to that described in Example 74 sub-part d. to give the des-hydroxy compound. Chromatography, with hexane:isopropanol (9:1) as the eluent gave the syn-compound as a viscous yellow oil; TLC: (9:1 hexane:isopropanol), Rf=0.19; NMR: 2.72 (m,2), 3.04 (s,3), 3.70 (m,1), 4.84–5.15 (m,3), 5.73 (m,1), 6.64 (dd,1), 6.95 (d,1), 7.40–7.66 (m,4), 7.84 (d,1); MS: m/z=392(M+1).

d. (3S*)-3-(4-Bromo-3-chlorophenyl)-3-((1R*)-2-methyl-3-oxo-2,3-dihydroxy-1H-isoindol-1-yl) propionaldehyde. The des-hydroxy compound was subjected to a procedure similar to that described in Example 74 sub-part e. to give the aldehyde. Chromatography, with hexane:isopropanol (9:1) as the eluent gave a tacky solid; TLC: (9:1 hexane:isopropanol), Rf=0.07; NMR: 3.03 (s,3), 3.12–3.18 (m,2), 4.02–4.13 (m,1), 4.85 (d,1), 6.75 (dd,1), 7.05 (d,1), 7.43–7.66 (m,4), 7.85 (d,1), 9.65 (s,1); MS: m/z=394(M+1).

EXAMPLE 102

(3R*)-3-[(1S*)-1-(4-Bromo-3-chlorophenyl)-3-(4-(2-oxopiperidino)piperidino)propyl]-2-methyl-2,3-dihydroisoindol-1-one citrate (3S*)-3-(4-Bromo-3-chlorophenyl)-3-((1R*)-2-methyl-3-oxo-2,3-dihydroxy-1H-isoindol-1-yl)propionaldehyde and 4-(2-oxopiperidino)piperidine were reductively coupled using a procedure similar to that described in Example 74 to give the title compound as a white solid; mp 115–120° C. (dec); NMR: selected signal 4.39 (m,1), 4.86 (d,1), 6.65 (d,1), 6.93 (s,1), 7.50 (m,3), 7.67 (m,1), 7.88 (d,1); MS: m/z=560(M+1). Analysis for $C_{28}H_{33}BrClN_3O_2 \cdot 1.0\ C_6H_8O_7 \cdot 1.0\ H_2O$: Calculated: C, 53.10; H, 5.64; N, 4.61. Found: C, 53.09; H, 5.46; N, 4.99.

EXAMPLE 103

(3R*)-3-[(1S*)-1-(4-Bromo-3-chlorophenyl)-3-(4-(2-oxopiperidino)-4-(methylaminocarbonyl) piperidino)propyl]-2-methyl-2,3-dihydroisoindol-1-one citrate (3S*)-3-(4-Bromo-3-chlorophenyl)-3-((1R*)-2-methyl-3-oxo-2,3-dihydroxy-1H-isoindol-1-yl)propionaldehyde and 4-(2-oxopiperidino)-4-(methylaminocarbonyl)piperidine were reductively coupled using a procedure similar to that described in Example 74 to give the title compound as a white solid; mp 130–135 C° (dec); NMR: selected signals: 4.84 (d,1), 6.68 (d,1), 6.93 (s,1), 7.45 (m,3), 7.66 (m,1), 7.85 (d,1); MS: m/z=617(M+1). Analysis for $C_{30}H_{36}BrClN_4O_3 \cdot 1.05\ C_6H_8O_7 \cdot 0.75\ H_2O$: Calculated: C, 52.45; H, 5.57; N, 6.74. Found: C, 52.84; H, 5.67; N, 6.58.

EXAMPLE 104

(3R*)-3-[(1S*)-1-(4-Biphenyl)-3-(4-(2-oxoperhydropyrimidine-1-yl)piperidino)propyl]-2-methyl-2,3-dihydroisoindol-1-one citrate To a vigorously stirred mixture of (3R*)-3-[(1S*)-1-(4-bromophenyl)-3-(4-(2-oxoperhydropyrimidine-1-yl)

piperidino)propyl]-2-methyl-2,3-dihydroisoindol-1-one (0.50 g, Example 79), tetrakis(tri-phenylphosphine) palladium (0.03 g), 2M aqueous sodium carbonate (1.5 mL) and toluene (3 mL) was added a solution of phenylboronic acid (0.13 g) in a minimum of 95% ethanol. The stirred mixture was heated at 90–95 C° for 6 hours, cooled, poured into water and extracted with ethyl acetate. The organic layer was dried, and evaporated. Chromatography, with dichloromethane:methanol (gradient 95:5-90:10) as the eluent gave the free base of the title compound (0.22 g). The citrate salt was prepared in methanol, the solvent evaporated, the residue triturated with ethyl ether, the ether distilled off and the treatment repeated to yield 0.20 g (28%) of the title compound; mp 150 C° (dec); NMR: selected signals: 4.19 (m,1), 4.85 (d,1), 6.23 (broad s,1), 6.85 (d,2), 7.29–7.67 (m,10), 7.89 (d,1); MS: m/z=523(M+1). Analysis for $C_{33}H_{38}N_4O_2 \cdot 1.0\ C_6H_8O_7 \cdot 2.0\ H_2O$: Calculated: C, 62.39; H, 6.71; N, 7.46. Found: C, 62.41; H, 6.51; N, 7.52.

EXAMPLE 105

(3R*)-3-[(1S*)-1-(4-methylthiophenyl)-3-(4-(2-oxoperhydropyrimidine-1-yl)piperidino)propyl]-2-methyl-2,3-dihydroisoindol-1-one citrate A stirred mixture of (3R*)-3-[(1S*)-1-(4-bromophenyl)-3-(4-(2-oxoperhydropyrimidine-1-yl)piperidino)propyl]-2-methyl-2,3-dihydroisoindol-1-one (0.5 g, Example 79), sodium thiomethoxide (0.11 g), tetrakis(triphenylphosphine) palladium (0.04 g) and n-butanol (5 mL) was heated at reflux overnight. The cooled mixture was filtered by suction through a Celite pad, the filtrate treated with water and extracted with ethyl acetate. The organic layer was dried and evaporated. Chromatography, with dichloromethane:methanol (gradient 95:5-90:10) as the eluent gave the free base of the title compound (0.13 g) as a light tan solid. The citrate salt was prepared in methanol, the solvent evaporated, the residue triturated with ethyl ether, the ether distilled off and the treatment repeated to yield the title compound (0.14 g) as a tan solid; mp 140 C° (dec). NMR indicated that some isomerization had occurred; selected signals: 4.15 (broad m), 4.82 (m), 6.24 (broad s), 6.68 (d), 6.76 (d), 6.92 (d), 7.06 (d), 7.20 (s), 7.26–7.63 (m), 7.86 (d); MS: m/z=493(M+1). Analysis for $C_{28}H_{36}N_4O_2S \cdot 1.0\ C_6H_8O_7 \cdot 1.0\ H_2O$: Calculated: C, 58.11; H, 6.60; N, 7.97. Found: C, 58.37; H, 6.41; N, 7.97.

EXAMPLE 106

3-[(1S*)-1-(3,4-Dichlorophenyl)-3-(4-hydroxy-4-phenylpiperidino)propyl]-2-methylisoquinol-1-one hydrochloride The second isomer to elute from the chiral OD column in Example 73 was converted to the hydrochloride salt to afford the desired 3-[(1S*)-1-(3,4-dichlorophenyl)-3-(4-hydroxy-4-phenylpiperidino)propyl]-2-methylisoqunol-1-one hydrochloride (0.41g); mp 193–215° C. (d); $[\alpha]_D=80$ (c=1.0 Methanol); MS: m/z=521(M+1); NMR (CD3OD): 2.0 (d,2, J=14), 2.3–2.5 (m,3), 2.7 (m,1), 3.2 (m,1), 3.3–3.6 (m,8), 4.5 (t,1, J=8), 7.0 (s,1), 7.2–7.4 (m,4), 7.2–7.4 (m,4), 7.5–7.69 (m,5), 7.8 (m,2), 8.3 (d,1, J=8). Analysis for $C_{30}H_{30}Cl_2N_2O_2 \cdot 1.0\ H_2O \cdot 1.0\ HCl$: Calculated C, 62.56; H, 5.77; N, 4.86; Found: C, 62.72 ; H, 5.74; N, 4.67.

In general a diastereomeric mixture of a compound of formula XVIII can be separated by chromatography to give a syn-diastereomer of formula XIX and an anti-diastereomer of formula XX as shown in Scheme III. Intermediates of formula XIX and XX can be converted to compounds of formula I wherein the syn- or anti- stereochemistry is conserved. In general, for compounds of formula I in which $Q^2$ is a radical of formula IIa, wherein $M^1$ is —CH—, the syn-diastereomer is preferred. In the above Examples, the compounds of Examples 9–27, 31–36, 39–46, 48–55, 60–65, 70, and 74–105 were prepared as the syn-diastereomer, the compound of Example 56 was prepared as the anti-diastereomer, and the compounds of Examples 28–30, 47 and 72 were prepared as a mixture of syn and anti diastereomers.

FORMULAE

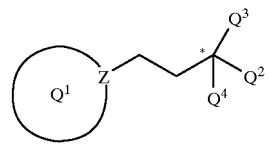

I

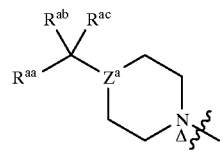

Ia

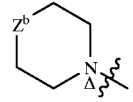

Ib

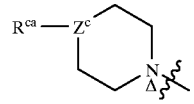

Ic

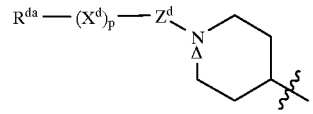

Id

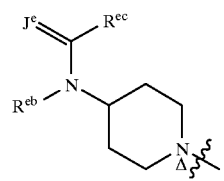

Ie

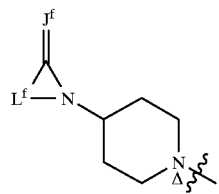

If

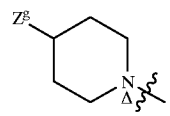

Ig

-continued
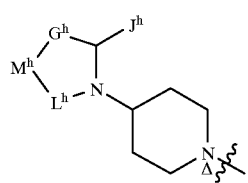
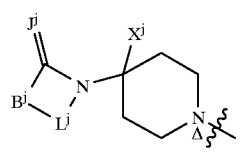
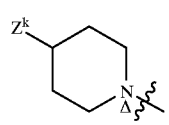
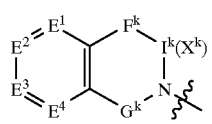
IIa
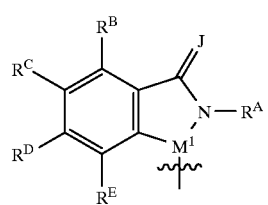
IIb
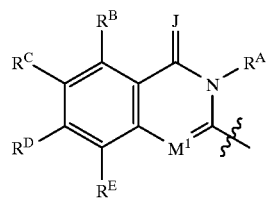
IIc
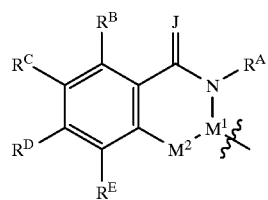
IId
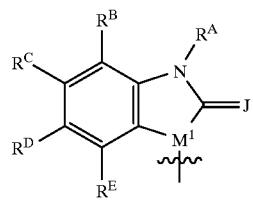
-continued
Ih
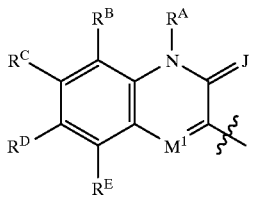
Ij
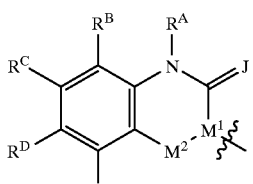
Ik
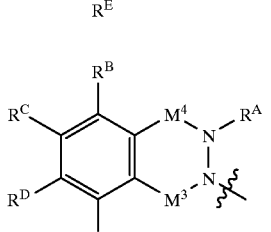
Il
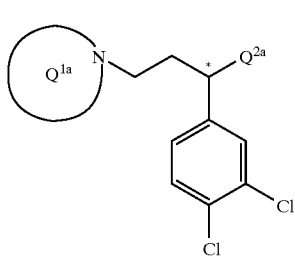
IIe
IIf
IIg
III
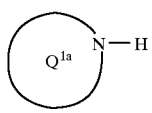
IIIa
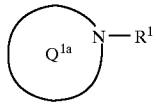
IIIb
IV
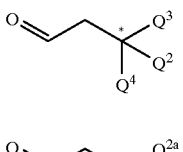
IVa

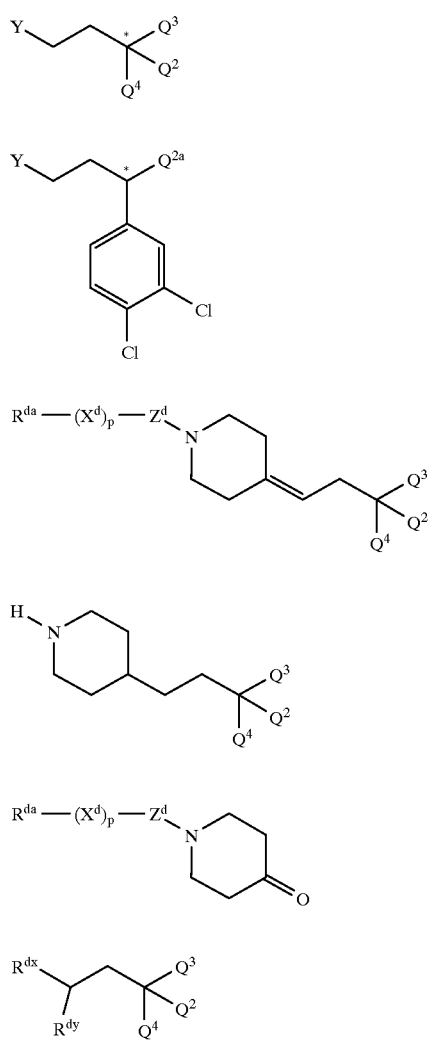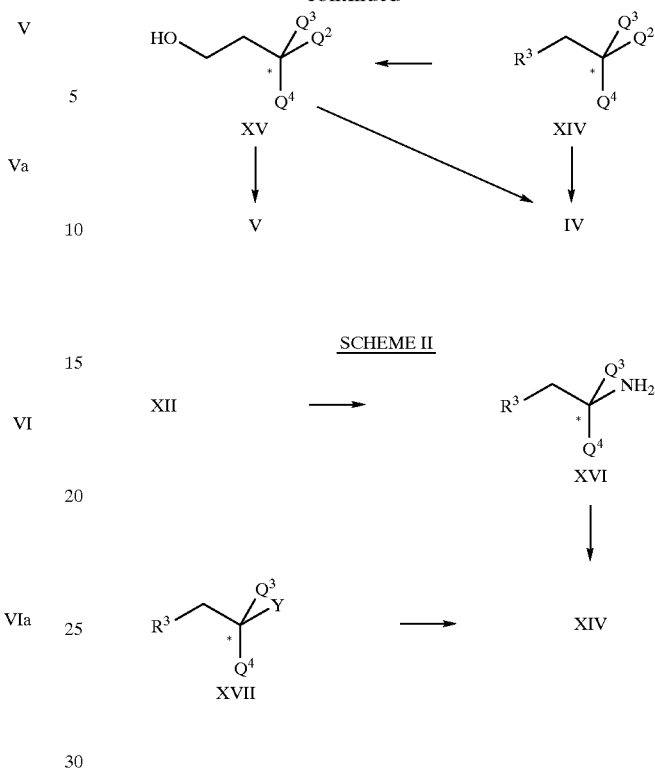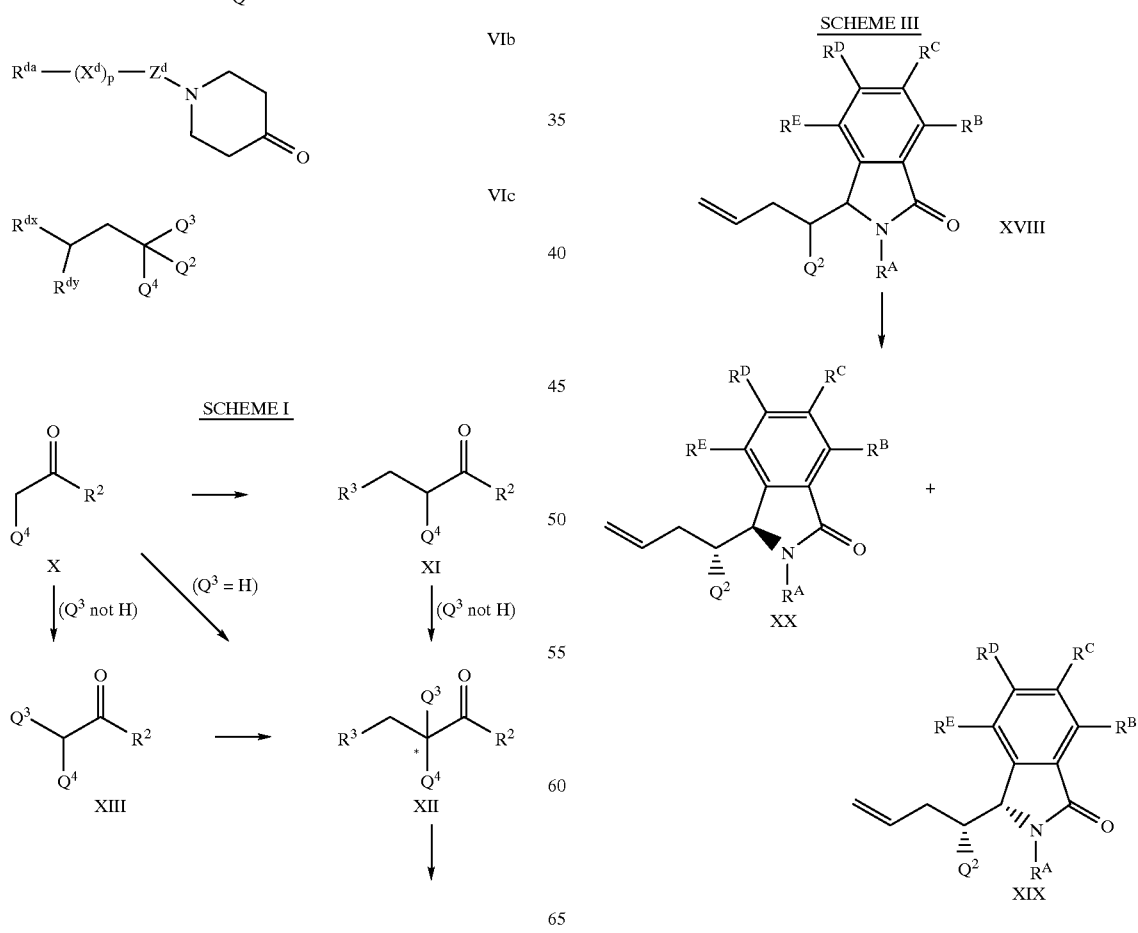

What is claimed is:

1. A compound of the following formula:

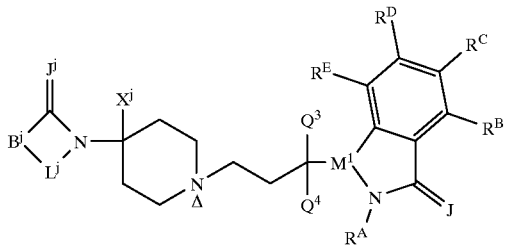

wherein:

X$^j$ is (1–6C)alkyl, —CH$_2$OR$^{ja}$, —CH$_2$SR$^{ja}$, —CH$_2$S(O)R$^{jg}$, —CH$_2$S(O)$_2$R$^{jg}$, —COR$^{ja}$, —COOR$^{ja}$, —C(=J$^{ja}$)NR$^{jb}$R$^{jc}$, —C(R$^{ja}$)(OR$^{jd}$)(OR$^{je}$), —CH$_2$N(R$^{ja}$)C(=J$^{ja}$)R$^{jf}$, —CH$_2$(R$^{ja}$)COOR$^{jg}$ or —CH$_2$N(R$^{ja}$)C(=J$^{ja}$)NR$^{jb}$R$^{jc}$;

B$^j$ is a direct bond and L$^j$ is a hydrocarbon chain in which the 1-position is bound to B$^j$ and L$^j$ is selected from trimethylene, tetramethylene, cis-1-butenylene and cis, cis-butadienylene; or B$^j$ is N(R$^{jh}$) and L$^j$ is a hydrocarbon chain selected from ethylene, trimethylene and cis-vinylene; or B$^j$ is N and L$^j$ is a hydrocarbon chain in which the 1-position is bound to B$^j$ and L$^j$ is cis,cis-prop-2-en-1-ylidin-3-yl;

J$^j$ and J$^{ja}$ are independently oxygen or sulfur;

R$^{ja}$, R$^{jf}$ and R$^{jh}$ are independently hydrogen or (1–6C)alkyl;

R$^{jb}$ and R$^{jc}$ are independently hydrogen or (1–6C)alkyl; or the radical NR$^{jb}$R$^{jc}$ is pyrrolidino, piperidino, morpholino, thiomorpholino (or its S-oxide) or piperazinyl (which piperazinyl may bear a (1–3C)alkyl substituent at the 4-position);

R$^{jd}$ and R$^{je}$ are independently (1–3C)alkyl or together form a divalent hydrocarbon chain selected from ethylene and trimethylene;

R$^{jg}$ is (1–6C)alkyl;

J is oxygen or sulfur;

M$^1$ is CR$^F$ or N;

R$^A$ is hydrogen or (1–3C)alkyl;

R$^B$, R$^C$, R$^D$, and R$^E$ are each hydrogen, or one or more of R$^B$, R$^C$, R$^D$, and R$^E$ is a substituent independently selected from halo, trifluoromethyl, hydroxy, (1–3C)alkoxy, (1–3C)alkyl, (1–3C)alkylthio, (1–3C)alkylsulfinyl and (1–3C)alkylsulfonyl, and the others of R$^B$, R$^C$, R$^D$, and R$^E$ are each hydrogen; or two adjacent R$^B$, R$^C$, R$^D$, and R$^E$ form a methylenedioxy substituent and the others of R$^B$, R$^C$, R$^D$, and R$^E$ are hydrogen;

R$^F$ is hydrogen, hydroxy, (1–3C)alkoxy or (1–3C)alkyl;

Q$^3$ is hydrogen or (1–3C)alkyl; and

Q$^4$ is phenyl which may bear one or two substituents independently selected from halo, trifluoromethyl, hydroxy, (1–3C)alkoxy, (1–3C)alkyl, methylenedioxy, (1–3C)alkoxycarbonyl and (1–3C)alkylthio; or Q$^4$ is thienyl, imidazolyl, benzo[b]thiophenyl or naphthyl any of which may bear a halo substituent; or Q$^4$ is biphenylyl; or Q$^4$ is carbon-linked indolyl which may bear a benzyl substituent at the 1-position;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen R$^1$ is (1–4C)alkyl or benzyl and the associated counterion A is a pharmaceutically acceptable anion.

2. The compound of claim 1 wherein Q$^4$ is phenyl which may bear one or two substituents independently selected from halo, trifluoromethyl, hydroxy, (1–3C)alkoxy, (1–3C) alkyl, and methylenedioxy; or Q$^4$ is thienyl, imidazolyl, benzo[b]thiophenyl or naphthyl any of which may bear a halo substituent; or Q$^4$ is biphenylyl; or Q$^4$ is carbon-linked indolyl which may bear a benzyl substituent at the 1-position.

3. The compound of claim 1 wherein Q$^4$ is 3,4-dichlorophenyl.

4. The compound of claim 1 wherein X$^j$ is methylaminocarbonyl.

5. The compound of claim 1 which is: 3-[1-(3,4-dichlorophenyl)-3-(4-methylaminocarbonyl)-4-(2-oxopiperidino)piperidino)propyl]-2-methyl-2,3-dihydro-6-methoxy-isoindol-1-one; 3-[1-(3,4-dichlorophenyl)-3-(4-(2-oxopiperidino)-4-(methylaminocarbonyl)piperidino)propyl]-2-methyl-2,3-dihydro-6-methoxy-isoindol-1-one; or 3-[1-(4-bromo-3-chlorophenyl)-3-(4-(2-oxopiperidino)-4-(methylaminocarbonyl)piperidino)propyl]-2-methyl-2,3-dihydro-6-methoxy-isoindol-1-one; or a pharmaceutically acceptable salt thereof.

6. The compound of claim 1 which is: (3R*)-3-[(1S*)-1-(4-bromo-3-chlorophenyl)-3-(4-(2-oxopiperidino)-4-(methylaminocarbonyl)piperidino)propyl]-2-methyl-2,3-dihydro-6-methoxy-isoindol-1-one; or a pharmaceutically acceptable salt thereof.

7. A pharmaceutical composition comprising a therapeutically effective amount of a compound of claim 1 and a pharmaceutically acceptable diluent or carrier.

8. A method of treating asthma in a human or other mammal in need thereof, comprising administering an effective amount of a compound of claim 1.

* * * * *